(12) United States Patent
Vaya et al.

(10) Patent No.: US 8,263,125 B2
(45) Date of Patent: *Sep. 11, 2012

(54) DOSAGE FORM FOR HIGH DOSE-HIGH SOLUBILITY ACTIVE INGREDIENTS THAT PROVIDES FOR IMMEDIATE RELEASE AND MODIFIED RELEASE OF THE ACTIVE INGREDIENTS

(75) Inventors: Navin Vaya, Gujarat (IN); Rajesh Singh Karan, Gujarat (IN); Sunil Sadanand Nadkarni, Gujarat (IN); Vinod Kumar Gupta, Gujarat (IN)

(73) Assignee: Torrent Pharmaceuticals Limited, Ahmedabad (IN)

( * ) Notice: Subject to any disclaimer, the term of this patent is extended or adjusted under 35 U.S.C. 154(b) by 0 days.

This patent is subject to a terminal disclaimer.

(21) Appl. No.: 11/134,633

(22) Filed: May 19, 2005

(65) Prior Publication Data
US 2006/0024365 A1 Feb. 2, 2006

Related U.S. Application Data

(63) Continuation-in-part of application No. 10/630,446, filed on Jul. 29, 2003, now Pat. No. 7,985,422.

(30) Foreign Application Priority Data

| Aug. 5, 2002 | (IN) | 697/MUM/2002 |
| Aug. 5, 2002 | (IN) | 699/MUM/2002 |
| Jan. 22, 2003 | (IN) | 80/MUM/2003 |
| Jan. 22, 2003 | (IN) | 82/MUM/2003 |

(51) Int. Cl.
*A61K 9/26* (2006.01)
*A61K 9/20* (2006.01)

(52) U.S. Cl. ......... 424/469; 424/464; 424/465; 424/468
(58) Field of Classification Search .................. None
See application file for complete search history.

(56) References Cited

U.S. PATENT DOCUMENTS

| 3,048,526 | A | * | 8/1962 | Boswell | 424/472 |
| 3,336,200 | A | | 8/1967 | Krause et al. | |
| 4,139,589 | A | * | 2/1979 | Beringer et al. | 264/250 |
| 4,503,031 | A | * | 3/1985 | Glassman | 424/467 |
| 4,996,061 | A | * | 2/1991 | Webb et al. | 424/475 |
| 5,445,829 | A | * | 8/1995 | Paradissis et al. | 424/480 |
| 5,738,874 | A | * | 4/1998 | Conte et al. | 424/472 |
| 5,840,332 | A | * | 11/1998 | Lerner et al. | 424/464 |
| 5,985,843 | A | | 11/1999 | Higo et al. | |
| 6,001,391 | A | | 12/1999 | Zeidler et al. | |
| 6,238,699 | B1 | | 5/2001 | Rubin | |
| 6,372,254 | B1 | * | 4/2002 | Ting et al. | 424/473 |
| 6,660,300 | B1 | * | 12/2003 | Timmins et al. | 424/469 |
| 2004/0156902 | A1 | * | 8/2004 | Lee et al. | 424/473 |

FOREIGN PATENT DOCUMENTS

WO WO/01/72286 10/2001

* cited by examiner

*Primary Examiner* — Anand Desai
*Assistant Examiner* — Melissa Mercier
(74) *Attorney, Agent, or Firm* — Hedman & Costigan, P.C.; James V. Costigan

(57) ABSTRACT

A dosage form comprising of a high dose, high solubility active ingredient as modified release and a low dose active ingredient as immediate release where the weight ratio of immediate release active ingredient and modified release active ingredient is from 1:10 to 1:15000 and the weight of modified release active ingredient per unit is from 500 mg to 1500 mg; a process for preparing the dosage form.

30 Claims, 10 Drawing Sheets

DOSAGE FORM FOR HIGH DOSE-HIGH SOLUBILITY ACTIVE INGREDIENTS THAT PROVIDES FOR IMMEDIATE RELEASE AND MODIFIED RELEASE OF THE ACTIVE INGREDIENTS

This application is a continuation-in-part of Ser. No. 10/630,446, filed Jul. 29, 2003 now U.S. Pat. No. 7,985,422.

FIELD OF INVENTION

This invention relates to a dosage form comprising of a high dose, high solubility active ingredient as modified release and a low dose active ingredient as immediate release where the weight ratio of immediate release active ingredient and modified release active ingredient is from 1:1 to 1:15000 and the weight of modified release high dose high solubility active ingredient per unit is from 500 mg to 1500 mg and the weight of immediate release active ingredient is up to 500 mg; a process for preparing the formulation. Low dose active ingredient in present invention can optionally be also in a form of modified release.

BACKGROUND OF THE INVENTION

Combining two active ingredients in one pharmaceutical unit to improve patient compliance is known in literature. It can be either in the form of two or more active ingredients in immediate release form or a combination of immediate release and modified release form. There are various techniques by which the combination of immediate release and modified release is formulated in single dosage form.

Several examples of formulations having combination of immediate release active ingredient and modified release active ingredient are described below.

Shoichi Higo and Kazuo Igusa describes in U.S. Pat. No. 5,985,843 various types of pharmaceutical formulations, which consists of a delayed release of sucralfate and an immediate release fraction of another active ingredient. The pharmaceutical dosage forms are a tablet formulation containing immediate release and delayed release granules; a two or three layer tablet; a tablet with delayed release core surrounded by immediate release shell; a delayed release tablet/granule coated with a film of immediate release active ingredient.

Similarly Jurgen Zeidler et. al describes in U.S. Pat. No. 6,001,391 a process for producing solid combination tablets, which have at least two phases. The one of the two phases is processed by melt extrusion technique and contains a water soluble or swellable binder.

A compressed V-shaped center scored double layer tablet is disclosed by George M. Krause et. al in U.S. Pat. No. 3,336,200, one layer of which contains immediate release Active Ingredient and the other layer contains sustained release Active Ingredient. The tablet is divisible in two equal halves.

Similarly Jacob A. Glassman described in U.S. Pat. No. 4,503,031 a super fast starting, slow release medicinal tablet, wherein the tablet is comprised of two layers of compressed matrix that are fused together by means of readily dissolvable adhesive substance.

Allan A. Rubin describes in U.S. Pat. No. 6,238,699 B1 a pharmaceutical dosage form of carbidopa and levodopa where both the Active Ingredients are present as immediate release and sustained release. The formulation is in the form of inlay tablet or bilayered tablet or a capsule containing pellets.

Block Jurgen et. al. describes in PCT application No. WO 01/72286 A1 a formulation of vitamin composition whereas a beadlet comprises a slow release core coated by a controlled release coating. The sustained release core is coated with an immediate release layer.

Richard Ting and Charles Hscao describes in U.S. Pat. No. 6,372,254 B1 a press coated, pulsatile active ingredient delivery system which comprises a core of immediate release, enveloped by an extended release compartment.

The need to use active ingredients with different and complementary mechanisms of action frequently arises in treatment of diabetes. There are several reasons to do this, namely, the disease itself is progressive, with deterioration of glycemic control over time; mono-therapeutic attempts to achieve and maintain glycemic control often fail in the long run; multiple defects in the disease and consequently primary drug failures (1,2,3).

Current guidelines for combination therapy advise the use of agents with differing and complementary mechanisms of action in order to maximize therapeutic activity and reduce toxicity. Earlier introduction of combination therapy is increasingly being recommended. The commonly combined active ingredients include biguanides (metformin)+sulphonylureas, biguanides+PPAR? agonists(thiazolidinediones), sulphonylureas+thiazolidinediones, non-sulfonylurea secretagogues (repaglinide)+biguanides etc. Fixed dose combinations of many of the above mentioned co-administer active ingredients have also been approved by the FDA. Most of these combinations are conventional formulations combined together into a single tablet. However, because of the disparity in the duration of action (half-life), these combinations are given twice or thrice a day.

To reduce this disparity in the duration of action, a novel strategy would be to combine a sustained release formulation of one active ingredient (shorter duration of action) with conventional formulation (long duration of action) of another active ingredient. This would make it possible to give the active ingredients in same dosing frequency.

This type of combination will give better compliance and a relative freedom from mealtime drug administration, thus, improving the quality of life. More importantly, because of prolonged duration of action, it shall produce a stricter control of blood glucose and consequently less diabetic complications.

The techniques described above do not work well when the difference in the dose of active ingredients are high for example where the weight ratio of active ingredients is from 1:1 to 1: 15000 and the dose of modified release active ingredient per unit is from 500 mg to 1500 mg. The techniques described in the prior art do not give good results when the active ingredient is highly soluble. The weight of the dosage form becomes very high, or complicated process for manufacturing is required, or accurate dosing of low dose active ingredient is difficult when the techniques reported in the prior art are utilized to make formulation with high dose, high solubility active ingredient in the form of modified release and low dose active ingredient into immediate release or modified release form where the weight ratio of low dose active ingredient and high dose, high solubility active ingredient is from 1:1 to 1:15000 and the weight of modified release active ingredient per unit is from 500 mg to 1500 mg and also it is inconvenient to swallow due to large size.

Accordingly a need exists for a dosage form providing combination of immediate release and modified release active ingredients and providing solution to problems associated with dosage forms described in prior art. Further, the dosage form should be simple and economical to produce.

Therefore an object of the present invention is a dosage form of combination of a high dose, high solubility active ingredient as modified release and a low dose active ingredient as immediate release where the weight ratio of immediate release active ingredient and modified release active ingredient is from 1:1 to 1:15000 and the weight of modified release active ingredient per unit is from 500 mg to 1500 mg.

Another object of the present invention is a dosage form, which is suitable for swallowing for humans containing two active ingredients one of which is in modified release form and other in immediate release form.

Accordingly, an object of the present invention to provide a dosage form, which uses dual retard technique to control the release of the high dose, high solubility active ingredient and significantly reduce the amount of release controlling agents which are otherwise required in very high quantity and make the dosage form very bulky and therefore pose difficulty in swallowing.

A further object of the present invention is to provide a dosage form, containing one active ingredient in an immediate release form and another active ingredient as modified release and the release or disintegration of the immediate release active ingredient is not hindered by the modified release ingredient.

Another object of the present invention is to provide a dosage form, which effectively avoids the problem of separation of layers of multilayered tablets.

A further object of the present invention is a formulation, which gives accurate dosing and is prepared by conventional and simple processes.

A further object of the present invention is to provide a dosage form, which can be given twice a day or more preferably can be given once a day.

A further object of the present invention is to provide a dosage form, wherein low dose active ingredient can optionally be also in a form of modified release.

SUMMARY OF THE INVENTION

The above objects are realized by a dosage form, which is comprised of an inner portion and an outer portion. The inner portion is surrounded by the outer portion in such a manner that only one surface of the inner portion is exposed. The inner portion contains a low dose active ingredient in immediate release form and the outer portion contains a high dose, high solubility active ingredient as modified release. The weight of the immediate release low dose active ingredient and high dose, high solubility modified release active ingredient is from 1:1 to 1:15000 and the weight of modified release active ingredient per unit is from 500 mg to 1500 mg. Low dose active ingredient in present invention can optionally be also in a form of modified release.

The present invention also provides solid oral dosage form comprising a composition according to the invention.

The present invention also teaches the use of dual retard technique to effectively control the release rate of modified release active ingredient by using small quantity of release controlling agents. This dual retard technique thus sufficiently reduces the size of the dosage form, which is convenient for swallowing.

The present invention further teaches the use of hydrophobic release controlling agents, which do not hinder the release of the low dose active ingredient.

The present invention further provides the dosage form that effectively prevents the problem of separation of the layers of the multilayered tablets.

The present invention also provides a novel process for preparing the novel formulations of the invention.

The present invention further provides a method of treating an animal, particularly a human in need of treatment utilizing the active agents, comprising administering a therapeutically effective amount of composition or solid oral dosage form according to the invention to provide administration of two active ingredients one in immediate release and other in modified release form.

DETAILED DESCRIPTION OF THE INVENTION

This invention relates to a novel dosage form of combination of high dose high solubility active ingredient, as modified release and low dose active ingredient as immediate release, suitable for swallowing comprising dual retard technique to control the release of the high dose high solubility active ingredient, with sufficient reduction in the amount of release controlling agent, without interfering the release of each other. Low dose active ingredient in present invention can optionally be also in a form of modified release.

The term "modified release" as used herein in relation to the composition according to the invention or a rate controlling polymer or used in any other context means release, which is not immediate release and is taken to encompass controlled release, sustained release, prolonged release, timed release, retarded release, extended release and delayed release. The term "modified release dosage form" as used herein can be described as dosage forms whose drug-release characteristics of time course and/or location are chosen to accomplish therapeutic or convenience objectives not offered by conventional dosage forms such as a solution or an immediate release dosage form. Modified release solid oral dosage forms include both delayed and extended release drug products (as per US FDA guideline for 'SUPAC-MR: Modified Release Solid Oral Dosage Forms').

The term "immediate release" as used herein in relation to composition according to the invention or used in any other context means release which is not modified release and releases more than 70% of the active ingredient within 60 minutes. The term "immediate release dosage form" as used herein can be described as dosage form which allows the drug to dissolve in the gastrointestinal contents, with no intention of delaying or prolonging the dissolution or absorption of the drug (as per US FDA guideline for 'SUPAC-MR: Modified Release Solid Oral Dosage Forms').

The term "dosage form" denotes any form of the formulation that contains an amount sufficient to achieve a therapeutic effect with a single administration.

The term "active ingredient" refers to an agent, active ingredient compound or other substance, or compositions and mixture thereof that provide some pharmacological, often beneficial, effect. Reference to a specific active ingredient shall include where appropriate the active ingredient and it's pharmaceutically acceptable salts.

The term "high dose" as used herein refers to the weight of active ingredient in unit dosage form according to the invention is from 500 mg to 1500 mg.

The term "low dose" as used herein refers to the weight of the active ingredient in unit dosage form according to the invention is less than or equal to 50 mg or may comprise up to but not including 500 mg or from more than 50 mg up to but no including 500 mg, preferably from 60 mg up to 400 mg or more preferable from 75 mg to 350 mg. The term "high solubility" as used herein in relation to high dose active ingredient means that from less than 1 part to 300 parts of water or less than 1 part to 30 parts of water will be required to dissolve 1 part of active ingredient.

The invention provides a novel dosage form of high dose, high solubility active ingredient as modified release and a low dose active ingredient as immediate release where the weight ratio of immediate release active ingredient and modified release active ingredient is from 1:10 to 1:15000 or 1:1 to 1:15000 and the weight of modified release antidiabetic active ingredient per unit is from 500 mg to 1500 mg; a process for preparing the dosage form.

The dosage form comprises of two parts (i) inner portion as an immediate release and (ii) outer portion as modified release. The two parts are compressed together in such a way that one surface of the inner portion remains exposed and the remaining surfaces are covered by the outer portion.

(i) Inner portion—Inner portion comprises of a low dose active ingredient and includes one or more commonly used excipients in oral immediate release pharmaceutical formulations. Low dose active ingredient in present invention can be either as an immediate release form or optionally as a modified release form.

The low dose active ingredient can be present in the form of a free base or in the form of pharmaceutically acceptable salts. Pharmaceutically acceptable salts forming part of this invention are intended to define but not limited to salts of the carboxylic acid moiety such as alkali metal salts like Li, Na and K salts; alkaline earth metal salts like Ca and Mg salts; salts of organic bases such as lysine, arginine, guanidine, diethanolamine, choline, and the like; ammonium or substituted ammonium salts and aluminium salts. Salts may be acid addition salts which defines but not limited to sulfates, nitrates, phosphates, perchlorates, borates, hydrohalides, acetates, tartrates, maleates, citrates, succinates, palmoates, methanesulfonates, benzoates, salicylates, hydroxynaphthoates, benzensulfonates, ascorbates, glycerophosphates, ketoglutarates and the like.

Further, the low dose active ingredient, where applicable, may be present either in the form of one substantially optically pure enantiomer or as a mixture of enantiomers or polymorphs thereof.

In the dosage form of the present invention, the inner portion may optionally contain more than one low dose active ingredient.

In the dosage form of the present invention, the inner portion may optionally contain more than one low dose antidiabetic active ingredient.

The low dose active ingredient is in the form of immediate release and has dose of 500 mg or less.

The low dose active ingredient comprises of the following therapeutic classes but not limited to adrenergic agent; adrenocortical steroid; adrenocortical suppressant; aldosterone antagonist; amino acid; anabolic; analeptic; analgesic; anesthetic; anorectic; anti-acne agent; anti-adrenergic; anti-allergic; anti-amebic; anti-anemic; anti-anginal; anti-arthritic; anti-asthmatic; anti-atherosclerotic; antibacterial; anticholinergic; anticoagulant; anticonvulsant; antidepressant; antidiabetic; antidiarrheal; antidiuretic; anti-emetic; anti-epileptic; antifibrinolytic; antifungal; antihemorrhagic; antihistamine; antihyperlipidemia; antihypertensive; antihypotensive; anti-infective; anti-inflammatory; antimicrobial; antimigraine; antimitotic; antimycotic, antinauseant, antineoplastic, antineutropenic, antiparasitic; antiproliferative; antipsychotic; antirheumatic; antiseborrheic; antisecretory; antispasmodic; antithrombotic; anti-ulcerative; antiviral; appetite suppressant; blood glucose regulator; bone resorption inhibitor; bronchodilator; cardiovascular agent; cholinergic; depressant; diagnostic aid; diuretic; dopaminergic agent; estrogen receptor agonist; fibrinolytic; fluorescent agent; free oxygen radical scavenger; gastric acid supressant; gastrointestinal motility effector; glucocorticoid; hair growth stimulant; hemostatic; histamine H2 receptor antagonists; hormone; hypocholesterolemic; hypoglycemic; hypolipidemic; hypotensive; imaging agent; immunizing agent; immunomodulator; immunoregulator; immunostimulant; immunosuppressant; keratolytic; LHRH agonist; mood regulator; mucolytic; mydriatic; nasal decongestant; neuromuscular blocking agent; neuroprotective; NMDA antagonist; non-hormonal sterol derivative; plasminogen activator; platelet activating factor antagonist; platelet aggregation inhibitor; psychotropic; radioactive agent; scabicide; sclerosing agent; sedative; sedative-hypnotic; selective adenosine A1 antagonist; serotonin antagonist; serotonin inhibitor; serotonin receptor antagonist; steroid; thyroid hormone; thyroid inhibitor; thyromimetic; tranquilizer; amyotrophic lateral sclerosis agent; cerebral ischemia agent; Paget's disease agent; unstable angina agent; vasoconstrictor; vasodilator; wound healing agent; xanthine oxidase inhibitor.

Examples of low dose active ingredient comprise but are not limited to 16-alpha fluorocstradiol, 16-alpha-gitoxin, 16-epiestriol, 17 alpha dihydroequilenin, 17 alpha estradiol, 17 beta estradiol, 17 hydroxy progesterone, lalpha-hydroxyvitamin D2,1-dodecpyrrolidinone, 20-epi-1,25 dihydroxyvitamin D3, 22-oxacalcitriol, 2CVV, 2'-nor-cGMP, 3-isobutyl GABA, 5-ethynyluracil, 6-FUDCA, 7-methoxytacrine, Abamectin, abanoquil, abecarnil, abiraterone, Ablukast, Ablukast Sodium, Acadesine, acamprosate, Acarbose, Acebutolol, Acecainide Hydrochloride, Aceclidine, aceclofenae, Acedapsone, Aceglutamide Aluminum, Acemannan, Acetaminophen, Acetazolamide, Acetohexamide, Acetohydroxamic Acid, acetomepregenol, Acetophenazine Maleate, Acetosulfone Sodium, Acetylcholine Chloride, Acetylcysteine, acetyl-L-carnitine, acetylmethadol, Acifran, acipimox, acitemate, Acitretin, Acivicin, Aclarubicin, aclatonium, Acodazole Hydrochloride, aconiazide, Acrisorcin, Acrivastine, Acronine, Actisomide, Actodigin, Acyclovir, acylfulvene, adafenoxate, adapalene, Adapalene, adatanserin, Adatanserin Hydrochloride, adecypenol, adecypenol, Adefovir, adelmidrol, ademetionine, Adenosine, Adinazolam, Adipheinine Hydrochloride, adiposin, Adozelesin, adrafinil, Adrenalone, airbutamine, alacepril, Alamecin, Alanine, Alaproclate, alaptide, Albendazole, albolabrin, Albuterol, Albutoin, Alclofenae, Alclometasone Dipropionate, Alcloxa, aldecalmycin, Aldesleukin, Aldioxa, Alendronate Sodium, alendronic acid, alentemol, Alentemol Hydrobromide, Aletamine Hydrochloride, Aleuronium Chloride, Alexidine, alfacalcidol, Alfentanil Hydrochloride, alfuzosin, Algestone Acetonide, alglucerase, Aliflurane, alinastine, Alipamide, Allantoin, Allobarbital, Allopurinol, ALL-TK antagonists, Alonimid, alosetron, Alosetron Hydrochloride, Alovudine, Alpertine, Alpha Amylase, alpha idosone, Alpidem, Alprazolam, Alprenolol Hydrochloride, Alprenoxime Hydrochloride, Alprostadil, Alrestatin Sodium, Altanserin Tartrate, Alteplase, Althiazide, Altretamine, altromycin B, Alverinc Citrate, Alvircept Sudotox, Amadinone Acetate, Amantadine Hydrochloride, ambamustine, Ambomycin, Ambruticin, Ambuphylline, Ambuside, Amcinafal, Amcinonide, Amdinocillin, Amdinocillin Pivoxil, Amedalin Hydrochloride, amelometasone, Ameltolide, Amesergide, Ametantrone Acetate, amezinium metilsulfate, amfebutamone, Amfenac Sodium, Amflutizole, Amicycline, Amidephrine Mesylate, amidox, Amifloxacin, amifostine, Amikacin, Amiloride Hydrochloride, Aminacrine Hydrochloride, Aminobenzoate Potassium, Aminobenzoate Sodium, Aminocaproic Acid, Aminoglutethimide, Aminohippurate Sodium, aminolevulinic acid, Aminophylline, A minorex, Aminosalicylate sodium, Aminosalicylic acid, Amiodarone, Amiprilose Hydrochloride, Amiquinsin Hydrochloride, amisulpride, Amitraz, Amitriptyline Hydrochloride, Amlexanox, amlodipine, Amobarbital Sodium, Amodiaquine, Amodiaquine Hydrochloride, Amorolfine, Amoxapine, Amoxicillin, Amphecloral, Amphetamine Sulfate, Amphomycin, Amphotericin B, Ampicillin, ampiroxicam, Ampyzine Sulfate, Amquinate, Amrinone, amrinone, amrubicin, Amsacrine, amylin, amythiamicin, Anagestone Acetate, anagrelide, Anakinra, ananain, anaritide, Anaritide Acetate, Anastrozole, Anazolene Sodium, Ancrod, andrographolide, Androstenedione, angiogenesis inhibitors, Angiotensin Amide, Anidoxime, Anileridine, Anilopam Hydrochloride, Aniracetam, Anirolac, Anisotropine Methylbromide, Anistreplase, Anitrazafen, anordrin, antagonist D, antagonist G, antarelix, Antazoline Phosphate, Anthelmycin, Anthralin, Anthramycin, antiandrogen, Acedapsone, Felbamate, antiestrogen, antineoplaston, Antipyrine, antisense oligonucleotides, apadoline, apafant, Apalcillin Sodium, apaxifylline, Apazone, aphidicolin glycinate, Apixifylline, Apomorphine Hydrochloride, apraclonidine, Apraclonidine Hydrochloride, Apramycin, Aprindine, Aprindine Hydrochloride, aprosulate sodium, Aprotinin, Aptazapine Maleate, aptiganel, apurinic acid, apurinic acid, aranidipine, Aranotin, Arbaprostil, arbekicin, arbidol, Arbutamine Hydrochloride, Arclofenin, Ardeparin Sodium, argatroban, Arginine, Argipressin Tannate, Arildone, aripiprazol, arotinolol, Arpinocid, Arteflene, Artilide Fumarate, asimadoline, aspalatone, Asparaginase, Asparic Acid, Aspartocin, asperfuran, Aspirin, aspoxicillin, Asprelin, Astemizole, Astromicin Sulfate, asulacrine, atamestane, Atenolol, atevirdine, Atipamezole, Atiprosin Maleate, Atolide, Atorvastatin Calcium, Atosiban, Atovaquone, atpenin B, Atracurium Besylate, atrimustine, atrinositol, Atropine, Auranofin, aureobasidin A, Aurothioglucose, Avilamycin, Avoparcin, Avridine, Axid, axinastatin 1, axinastatin 2, axinastatin 3, Azabon, Azacitidinie, Azaclorzine Hydrochloride, Azaconazole, azadirachtine, Azalanstat Dihydrochloride, Azaloxan Fumarate, Azanator Maleate, Azanidazole, Azaperone, Azaribine, Azaserine, azasetron, Azatadine Maleate, Azathioprine, Azathioprine Sodium, azatoxin, azatyrosine, azelaic acid, azelastine, azelnidipine, Azepindole, Azetepa, azimilide, Azithromycin, Azlocillin, Azolimine, Azosemide, Azotomycin, Aztreonam, Azumolene Sodium, Bacampicillin Hydrochloride, baccatin III, Bacitracin, Baclofen, bacoside A, bacoside B, bactobolamine, balanol, balazipone, balhimycin, balofloxacin, balsalazide, Bambermycins, bambuterol, Bamethan Sulfate, Bamifylline Hydrochloride, Bamidazole, baohuoside 1, Barmastine, barnidipine, Basifungin, Batanopride Hydrochloride, batebulast, Batelapine Maleate, Batimastat, beauvericin, Becanthone Hydrochloride, becaplermin, becliconazole, Beclomethasone Dipropionate, befloxatone, Beinserazide, Belfosdil, Belladonna, Beloxamide, Bemesetron, Bemitradine, Bemoradan, Benapryzine Hydrochloride, Benazepril Hydrochloride, Benazeprilat, Bendacalol Mesylate, Bendazac, Bendroflumethiazide, benflumetol, benidipine, Benorterone, Benoxaprofen, Benoxaprofen, Benoxinate Hydrochloride, Benperidol, Bentazepam, Bentiromide, Benurestat, Benzbromarone, Benzethonium Chloride, Benzetimide Hydrochloride, Benzilonium Bromide, Benzindopyrine Hydrochloride, benzisoxazole, Benzocaine, benzochlorins, Benzoctamine Hydrochloride, Benzodepa, benzoidazoxan, Benzonatate, Benzoyl Peroxide, Benzoylpas Calcium, benzoylstaurosporine, Benzquinamide, Benzthiazide, benztropine, Benztropine Mesylate, Benzydamine Hydrochloride, Benzylpenicilloyl Polylysine, bepridil, Bepridil Hydrochloride, Beractant, Beraprost, Berefrine, berlafenone, bertosamil, Berythromycin, besipirdine, beta-alethine, betaclamycin B, Betamethasone, betamipron, betaxolol, Betaxolol Hydrochloride, Bethanechol Chloride, Bethanidine Sulfate, betulinic acid, bevantolol, Bevantolol Hydrochloride, Bezafibrate, bFGF inhibitor, Bialamicol Hydrochloride, Biapenem, Bicalutamide, Bicifadine Hydrochloride, Biclodil Hydrochloride, Bidisomide, bifemelane, Bifonazole, bimakalim, bimithil, Bindarit, Biniramycin, binospirone, bioxalomycin alpha2, Bipenamol Hydrochloride, Biperiden, Biphenamine Hydrochloride, biriperone, bisantrene, bisaramil, bisaziridinylspermine, bis-benzimidazole A, bis-benzimidazole B, bisnafide, Bisobrin Lactate, Bisoprolol, Bispyrithione Magsulfex, bistramide D, bistramide K, bistratene A, Bithionolate Sodium, Bitolterol Mesylate, Bivalirudin, Bizelesin, Bleomycin Sulfate, Bolandiol Dipropionate, Bolasterone, Boldenone Undecylenate, boldine, Bolenol, Bolmantalate, bopindolol, Bosentan, Boxidine, brefeldin, breflate, Brequinar Sodium, Bretazenil, Bretylium Tosylate, Brifentanil Hydrochloride, brimonidine, Brinolase, Brocresine, Brocrinat, Brofoxine, Bromadoline Maleate, Bromazepam, Bromchlorenone, Bromelains, bromfenac, Brominidione, Bromocriptine, Bromodiphenhydramine Hydrochloride, Bromoxamide, Bromperidol, Bromperidol Decanoate, Brompheniramine Maleate, Broperamole, Bropirimine, Brotizolam, Bucainide Maleate, bucindolol, Buclizine Hydrochloride, Bucromarone, Budesonide, budipine, budotitane, Buformin, Bumetamide, Bunaprolast, bunazosin, Bunolol Hydrochloride, Bupicomide, Bupivacaine Hydrochloride, Buprenorphine Hydrochloride, Bupropion Hydrochloride, Buramate, Buserelin Acetate, Buspirone Hydrochloride, Busulfan, Butabarbital, Butacetin, Butaclamol Hydrochloride, Butalbital, Butamben, Butamirate Citrate, Butaperazine, Butaprost, Butedronate Tetrasodium, butenafine, Buterizine, buthionine sulfoximine, Butikacin, Butilfenin, Butirosin Sulfate, Butixirate, butixocort propionate, Butoconazole Nitrate, Butonate, Butopamine, Butoprozine Hydrochloride, Butorphanol, Butoxamine Hydrochloride, Butriptyline Hydrochloride, Cactinomycin, Cadexomer Iodine, Caffeine, calanolide A, Calcifediol, Calcipotriene, calcipotriol, Calcitonin, Calcitriol, Calcium Undecylenate, calphostin C, Calusterone, Cambendazole, camonagrel, camptothecin derivatives, canarypox IL-2, candesartan, Candicidin, candoxatril, candoxatrilat, Caniglibose, Canrenoate Potassium, Canrenone, capecitabine, Capobenate Sodium, Capobenic Acid, Capreomycin Sulfate, capromab, capsaicin, Captopril, Capuride, Caracemide, Carbachol, Carbadox, Carbamazepine, Carbamide Peroxide, Carbantel Lauryl Sulfate, Carbaspirin Calcium, Carbazeran, carbazomycin C, Carbenicillin Potassium, Carbenoxolone Sodium, Carbetimer, carbetocin, Carbidopa, Carbidopa-Levodopa, Carbinoxamine Maleate, Carbiphene Hydrochloride, Carbocloral, Carbocysteine, Carbol-Fuchsin, Carboplatin, Carboprost, carbovir, carboxamide-amino-triazo-le, carboxyamidotriazole, carboxymethylated beta-1,3-glucan, Carbuterol Hydrochloride, CaRest M3, Carfentanil Citrate, Carisoprodol, Carmantadine, Carmustine, CARN 700, Camidazole, Caroxazone, carperitide, Carphenazine Maleate, Carprofen, Carsatrin Succinate, Cartazolate, carteolol, Carteolol Hydrochloride, cartilage derived inhibitor, Carubicin Hydrochloride, Carumonam Sodium, carvedilol, carvotroline, Carvotroline Hydrochloride, carzelesin, casein kinase inhibitors (ICOS), castanospermine, caurumonam, cebaracetam, cecropin B, Cedefingol, Cefaclor, Cefadroxil, Cefamandole, Cefaparole, Cefatrizine, Cefazaflur Sodium, Cefazolin, Cefbuperazone, cefcapene pivoxil, cefdaloxime pentexil tosilate, Cefdinir, cefditoren pivoxil, Cefepime, cefetamet, Cefetecol, cefixime, cefluprenam, Cefinenoxime Hydrochloride, Cefinetazole, cefminlox, cefodizime, Cefonicid Sodium, Cefoperazone Sodium, Ceforamide, cefoselis, Cefotaxime Sodium, Cefotetan, cefotiam, Cefoxitin, cefozopran, cefpimizole, Cefpiramide, cefpirome, cefpodoxime proxetil, cefprozil, Cefroxadine, cefsulodin, Ceftazidime, cefteram, ceftibuten, Ceftizoxime Sodium, ceftriaxone, Cefuroxime, celastrol, celikalim, celiprolol, cepacidiine A, Cephacetrile Sodium, Cephalexin, Cephaloglycin, Cephaloridine, Cephalothin Sodium, Cephapirin Sodium, Cephradine, cericlamine, cerivastatin, Ceronapril, certoparin sodium, Ceruletide, Cetaben Sodium, Cetalkonium Chloride, Cetamolol Hydrochloride, cetiedil, cetirizine, Cetophenicol, Cetraxate Hydrochloride, cetrorelix, Cetylpyridinium Chloride, Chenodiol, Chlophedianol Hydrochloride, Chloral Betaine, Chlorambucil, Chloramphenicol, Chlordantoin, Chlordiazepoxide, Chlorhexidine Gluconate, chlorins, Chlormadinone Acetate, chloroorienticin A, Chloroprocaine Hydrochloride, Chloropropamide, Chloroquine, chloroquinoxaline sulfonamide, Chlorothiazide, Chlorotrianisene, Chloroxine, Chloroxylenol, Chlorphenesin Carbamate, Chlorpheniramine Maleate, Chlorpromazine, Chlorpropamide, Chlorprothixene, Chlortetracycline Bisulfate, Chlorthalidone, Chlorzoxazone, Cholestyramine Resin, Chromonar Hydrochloride, cibenzoline, cicaprost, Ciclafrine Hydrochloride, Ciclazindol, ciclesonide, cicletanine, Ciclopirox, Cicloprofen, cicloprolol, Cidofovir, Cidoxepin Hydrochloride, Cifenline, Ciglitazone, Ciladopa Hydrochloride, cilansetron, Cilastatin Sodium, Cilazapril, cilnidipine, Cilobamine Mesylate, cilobradine, Cilofungin, cilostazol, Cimaterol, Cimetidine, cimetropium bromide, Cinalukast, Cinanserin Hydrochloride, Cinepazet Maleate, Cinflumide, Cingestol, cinitapride, Cinnamedrine, Cinnarizine, cinolazepam, Cinoxacin, Cinperene, Cinromide, Cintazone, Cintriamide, Cioteronel, Cipamfylline, Ciprefadol Succinate, Ciprocinonide, Ciprofibrate, Ciprofloxacin, ciprostene, Ciramadol, Cirolemycin, cisapride, cisatracurium besilate, Cisconazole, Cisplatin, cisporphyrin, cistinexine, citalopram, Citenamide, citicoline, citreamicin alpha, cladribine, Clamoxyquin Hydrochloride, Clarithromycin, clausenamide, Clavulanate Potassium, Clazolam, Clazolimine, clebopride, Clemastine, Clentiazem Maleate, Clidinium Bromide, clinafloxacin, Clindamycin, Clioquinol, Clioxamide, Cliprofen, clobazam, Clobetasol Propionate, Clobetasone Butyrate, Clocortolone Acetate, Clodanolene, Clodazon Hydrochloride, clodronic acid, Clofazimine, Clofibrate, Clofilium Phosphate, Clogestone Acetate, Clomacran Phosphate, Clomegestone Acetate, Clometherone, clomethiazole, clomifene analogues, Clominorex, Clomiphene, Clomipramine Hydrochloride, Clonazepam, Clonidine, Clonitrate, Clonixeril, Clonixin, Clopamide, Clopenthixol, Cloperidone Hydrochloride, clopidogrel, Clopimozide, Clopipazan Mesylate, Clopirac, Cloprednol, Cloprostenol Sodium, Clorazepate Dipotassium, Clorethate, Clorexolone, Cloroperone Hydrochloride, Clorprenaline Hydrochloride, Clorsulon, Clortermine Hydrochloride, Closantel, Closiramine Aceturate, Clothiapine, Clothixamide Maleate Cloticasone Propionate, Clotrimazole, Cloxacillin Benzathine, Cloxyquin, Clozapine, Cocaine, Coccidioidin, Codeine, Codoxime, Colchicine, colestimide, Colestipol Hydrochloride, Colestolone, Colforsin, Colfosceril Palmitate, Colistimethate Sodium, Colistin Sulfate, collismycin A, collismycin B, Colterol Mesylate, combretastatin A4, combretastatin analogue, complestatin, conagenin, Conorphone Hydrochloride, contignasterol, contortrostatin, Cormethasone Acetate, Corticorelin Ovine Triflutate, Corticotropin, Cortisone Acetate, Cortivazol, Cortodoxone, cosalane, costatolide, Cosyntropin, cotinine, Coumadin, Coumermycin, crambescidin 816, Crilvastatin, crisnatol, Cromitrile Sodium, Cromolyn Sodium, Crotamiton, cryptophycin 8, cucumariosid, Cuprimyxin, curacin A, curdlan sulfate, curiosin, Cyclacillin, Cyclazocine, cyclazosin, cyclic HPMPC, Cyclindole, Cycliramine Maleate, Cyclizine, Cyclobendazole, cyclobenzaprine, cyclobut A, cyclobut G, cyclocapron, Cycloguanil Pamoate, Cycloheximide, cyclopentanthraquinones, Cyclopenthiazide, Cyclopentolate Hydrochloride, Cyclophenazine Hydrochloride, Cyclophosphamide, cycloplatam, Cyclopropane, Cycloserine, cyclosin, Cyclosporine, cyclothialidine, Cyclothiazide, cyclothiazomycin, Cyheptamide, cypemycin, Cypenamine Hydrochloride, Cyprazepam, Cyproheptadine Hydrochloride, Cyprolidol Hydrochloride, cyproterone, Cyproximide, Cysteamine, Cysteine Hydrochloride, Cystine, Cytarabine, Cytarabine Hydrochloride, cytarabine ocfosfate, cytochalasin B, cytolytic factor, cytostatin, Dacarbazine, dacliximab, dactimicin, Dactinomycin, daidzein, Daledalin Tosylate, dalfopristin, Dalteparin Sodium, Daltroban, Dalvastatin, danaparoid, Danazol, Dantrolene, daphlnodorin A, dapiprazole, dapitant, Dapoxetine Hydrochloride, Dapsone, Daptomycin, Darglitazone Sodium, darifenacin, darlucin A, Darodipine, darsidomine, Daunorubicin Hydrochloride, Dazadrol Maleate, Dazepinil Hydrochloride, Dazmegrel, Dazopride Fumarate, Dazoxiben Hydrochloride, Debrisoquin Sulfate, Decitabine, deferiprone, deflazacort, Dehydrocholic Acid, dehydrodidemnin B, Dehydroepiandrosterone, delapril, Delapril Hydrochloride, Delavirdine Mesylate, delequamine, delfaprazine, Delmadinone Acetate, delmopinol, delphinidin, Demecarium Bromide, Demeclocycline, Demecycline, Demoxepam, Denofungin, deoxypyridinoline, Depakote, deprodone, Deprostil, depsidomycin, deramciclane, dermatan sulfate, Desciclovir, Descinolone Acetonide, Desflurane, Desipramine Hydrochloride, desirudin, Deslanoside, deslorelin, desmopressin, desogestrel, Desonide, Desoximetasone, desoxoamiodarone, Desoxycorticosterone Acetate, detajmium bitartrate, Deterenol Hydrochloride, Detirelix Acetate, Devazepide, Dexamethasone, Dexamisole, Dexbrompheniramine Maleate, Dexchlorpheniramine Maleate, Dexclamol Hydrochloride, Dexetimide, Dexfenfluramine Hydrochloride, dexifosfamide, Deximafen, Dexivacaine, dexketoprofen, dexloxiglumide, Dexmedetomidine, Dexormaplatin, Dexoxadrol Hydrochloride, Dexpanthenol, Dexpemedolac, Dexpropranolol Hydrochloride, Dexrazoxane, dexsotalol, dextrin 2-sulphate, Dextroamphetamine, Dextromethorphan, Dextrorphan Hydrochloride, Dextrothyroxine Sodium, dexverapamil, Dezaguanine, dezinamide, dezocine, Diacetolol Hydrochloride, Diamocaine Cyclamate, Diapamide, Diatrizoate Meglumine, Diatrizoic Acid, Diaveridine, Diazepam, Diaziquone, Diazoxide, Dibenzepin Hydrochloride, Dibenzothiophene, Dibucaine, Dichlorvos, Dichloralphenazone, Dichlorphenamide, Dicirenone, Diclofenac Sodium, Dicloxacillin, dicranin, Dicumarol, Dicyclomine Hydrochloride, Didanosine, didemnin B, didox, Dienestrol, dienogest, Diethylcarbamazine Citrate, diethylhomospermine, diethylnorspermine, Diethylpropion Hydrochloride, Diethylstilbestrol, Difenoximide Hydrochloride, Difenoxin, Diflorasone Diacetate, Difloxacin Hydrochloride, Difluanine Hydrochloride, Diflucortolone, Diflumidone Sodium, Diflunisal, Difluprednate, Diftalone, Digitalis, Digitoxin, Digoxin, Dihexyverine Hydrochloride, dihydrexidine, dihydro-5-azacytidine, Dihydrocodeine Bitartrate, Dihydroergotamine Mesylate, Dihydroestosterone, Dihydrostreptomycin Sulfate, Dihydrotachysterol, dihydrotaxol, 9-, Dilantin, Dilevalol Hydrochloride, Diltiazem Hydrochloride, Dimefadane, Dimefline Hydrochloride, Dimenhydrinate, Dimercaprol, Dimethadione, Dimethindene Maleate, Dimethisterone, dimethyl prostaglandin Al, Dimethyl Sulfoxide, dimethylhomospermine, dimiracetam, Dimoxamine Hydrochloride, Dinoprost, Dinoprostone, Dioxadrol Hydrochloride, dioxamycin, Diphenhydramine Citrate, Diphenidol, Diphenoxylate Hydrochloride, diphenyl spiromustine, Dipivefin Hydrochloride, Dipivefrin, dipliencyprone, diprafenone, dipropylnorspermine, Dipyridamole, Dipyrithione, Dipyrone, dirithromycin, discodermolide, Disobutamide, Disofenin, Disopyramide, Disoxaril, disulfiram, Ditekiren, Divalproex Sodium, Dizocilpine Maleate, Dobutamine, docarpamine, Docebenone, Docetaxel, Doconazole, docosanol, dofetilide, dolasetron, Ebastine, ebiratide, ebrotidine, ebselen, ecabapide, ecabet, ecadotril, ecdisteron, echicetin, echistatin, Echothiophate Iodide, Eclanamine Maleate, Eclazolast, ecomustine, Econazole, ecteinascidin 722, edaravone, Edatrexate, edelfosine, Edifolone Acetate, edobacomab, Edoxudine, edrecolomab, Edrophonium Chloride, edroxyprogesteone Acetate, efegatran, eflornithine, efonidipine, egualcen, Elantrine, eleatonin, elemene, eletriptan, elgodipine, eliprodil, Elsamitrucin, eltenae, Elucaine, emalkalim, emedastine, Emetine Hydrochloride, emiglitate, Emilium Tosylate, emitefur, emoctakin, Enadoline Hydrochloride, enalapril, Enalaprilat, Enalkiren, enazadrem, Encyprate, Endralazine Mesylate, Endrysone, Enflurane, englitazone, Enilconazole, Enisoprost, Enlimomab, Enoplatin, Enofelast, Enolicam Sodium, Enoxacin, enoxacin, enoxaparin sodium, Enoxaparin Sodium, Enoximone, Enpiroline Phosphate, Enprofylline, Enpromate, entacapone, enterostatin, Enviradene, Enviroxime, Ephedrine, Epicillin, Epimestrol, Epinephrine, Epinephryl Borate, Epipropidine, Epirizole, epirubicin, Epitetracycline Hydrochloride, Epithiazide, Epoetin Alfa, Epoetin Beta, Epoprostenol, Epoprostenol Sodium, epoxymexrenone, episteride, Eprosartan, eptastigmine, equilenin, Equilin, Erbulozole, erdosteine, Ergoloid Mesylates, Ergonovine Maleate, Ergotamine Tartrate, ersentilide, Ersofermin, erythritol, Erythrityl Tetranitrate, Erythromycin, Esmolol Hydrochloride, Esorubicin Hydrochloride, Esproquin Hydrochloride, Estazolam, Estradiol, Estramustine, estramustine analogue, Estrazinol Hydrobromide, Estriol, Estrofurate, estrogen agonists, estrogen antagonists, Estrogens, Conjugated Estrogens, Esterified Estrone, Estropipate, esuprone, Etafedrine Hydrochloride, Etanidazole, etanterol, Etarotene, Etazolate Hydrochloride, Eterobarb, ethacizin, Ethacrynate Sodium, Ethacrynic Acid, Ethambutol Hydrochloride, Ethamivan, Ethanolamine Oleate, Ethehlorvynol, Ether, Ethinyl estradiol, Ethiodized Oil, Ethionamide, Ethonam Nitrate, Ethopropazine Hydrochloride, Ethosuximide, Ethotoin, Ethoxazene Hydrochloride, Ethybenztropine, Ethyl Chloride, Ethyl Dibunate, Ethylestrenol, Ethyndiol, Ethynerone, Ethynodiol Diacetate, Etibendazole, Etidocaine, Etidronate Disodium, Etidronic Acid, Etifenin, Etintidine Hydrochloride, etizolam, Etodolac, Etofenamate, Etoformin Hydrochloride, Etomidate, Etonogestrel, Etoperidone Hydrochloride, Etoposide, Etoprine, Etoxadrol Hydrochloride, Etozolin, etrabamine, Etretinate, Etryptamine Acetate, Eucatropine Hydrochloride, Eugenol, Euprocin Hydrochloride, eveminomicin, Exametazime, examorelin, Exaprolol Hydrochloride, exemestane, fadrozole, faeriefungin, Famciclovir, Famotidine, Fampridine, fantofarone, Fantridone Hydrochloride, faropenem, fasidotril, fasudil, fazarabine, fedotozine, felbamate, Felbinac, Felodipine, Felypressin, Fenalamide, Fenamole, Fenbendazole, Fenbufen, Fencibutirol, Fenclofenac, Fenclonine, Fenclorac, Fendosal, Fenestrel, Fenethylline Hydrochloride, Fenfluramine Hydrochloride, Fengabine, Fenimide, Fenisorex, Fenmetozole Hydrochloride, Fenmetramide, Fenobam, Fenoctimine Sulfate, fenofibrate, fenoldopam, Fenoprofen, Fenoterol, Fenpipalone, Fenprinast Hydrochloride, Fenprostalene, Fenquizone, fenretinide, fenspiride, Fentanyl Citrate, Fentiazac, Fenticlor, fenticonazole, Fenyripol Hydrochloride, fepradinol, ferpifosate sodium, ferristene, ferrixan, Ferrous Sulfate, Dried, Ferumoxides, ferumoxsil, Fetoxylate Hydrochloride, fexofenadine, Fezolamine Fumarate, Fiacitabine, Fialuridine, Fibrinogen 1 125, filgrastim, Filipin, finasteride, Flavodilol Maleate, flavopiridol, Flavoxate Hydrochloride, Flazalone, flecainide, flerobuterol, Fleroxacin, flesinoxan, Flestolol Sulfate, Fletazepam, flezelastine, flobufen, Floctafenine, flomoxef, Flordipine, florfenicol, florifenine, flosatidil, Flosequinan, Floxacillin, Floxuridine, fluasterone, Fluazacort, Flubanilate Hydrochloride, Flubendazole, Flucindole, Flucloronide, Fluconazole, Flucytosine, Fludalanine, Fludarabine Phosphate, Fludazonium Chloride, Fludeoxyglucose F 18, Fludorex, Fludrocortisone Acetate, Flufenamic Acid, Flufenisal, Flumazenil, flumecinol, Flumequine, Flumeridone, Flumethasone, Flumetramide, Flumezapine, Fluminorex, Flumizole, Flumoxonide, flunarizine, Flunidazole, Flunisolide, Flunitrazepam, Flunixin, fluocalcitriol, Fluocinolone Acetonide, Fluocinonide, Fluocortin Butyl, Fluocortolone, Fluorescein, fluorodaunorunicin hydrochloride, Fluorodopa F 18, Fluorometholone, Fluorouracil, Fluotracen Hydrochloride, Fluoxetine, Fluoxymesterone, fluparoxan, Fluperamide, Fluperolone Acetate, Fluphenazine Decanoate, flupirtine, Fluprednisolone, Fluproquazone, Fluprostenol Sodium, Fluquazone, Fluradoline Hydrochloride, Flurandrenolide, Flurazepam Hydrochloride, Flurbiprofen, Fluretofen, flurithromycin, Flurocitabine, Flurofamide, Flurogestone Acetate, Flurothyl, Fluroxene, Fluspiperone, Fluspirilene, Fluticasone Propionate, flutrimazole, Flutroline, fluvastatin, Fluvastatin Sodium, fluvoxamine, Fluzinamide, Folic Acid, Follicle regulatory protein, Folliculostatin, Fomepizole, Fonazine Mesylate, forasartan, forfenimex, forfenirmex, formestane, Formocortal, formoterol, Fosarilate, Fosazepam, Foscarnet Sodium, fosfomycin, Fosfonet Sodium, fosinopril, Fosinoprilat, fosphenyloin, Fosquidone, Fostedil, fostriecin, fotemustine, Fuchsin, Basic, Fumoxicillin, Fungimycin, Furaprofen, Furazolidone, Furazolium Chloride, Furegrelate Sodium, Furobufen, Furodazole, Furosemide, Fusidate Sodium, Fusidic Acid, gabapentin, Gadobenate Dimeglumine, gadobenic acid, gadobutrol, Gadodiamide, gadolinium texaphyrin, Gadopentetate Dimegiumine, gadoteric acid, Gadoteridol, Gadoversetamide, galantamine, galdansetron, Galdansetron Hydrochloride, Gallamine Triethiodide, gallium nitrate, gallopamil, galocitabine, Gamfexine, gamolenic acid, Ganciclovir, ganirelix, gelatinase inhibitors, Gemcadiol, Gemcitabine, Gemeprost, Gemfibrozil, Gentamicin Sulfate, Gentian Violet, gepirone, Gestaclone, Gestodene, Gestonorone Caproate, Gestrinone, Gevotroline Hydrochloride, girisopam, glaspimod, glaucocalyxin A, Glemanserin, Gliamilide, Glibornuride, Glicetanile Sodium, Gliflumide, Glimepiride, Glipizide, Gloximonam, Glucagon, glutapyrone, glutathione inhibitors, Glutethimide, Glyburide, glycopine, glycopril, Glycopyrrolate, Glyhexamide, Glymidine Sodium, Glyoctamide, Glyparamide, Gold Au 198, Gonadoctrinins, Gonadorelin, Gonadotropins, Goserelin, Gramicidin, Granisetron, grepafloxacin, Griseofulvin, Guaiapate, Guaithylline, Guanabenz, Guanabenz Acetate, Guanadrel Sulfate, Guancydine, Guanethidine Monosulfate, Guanfacine Hydrochloride, Guanisoquin Sulfate, Guanoclor Sulfate, Guanoctine Hydrochloride, Guanoxabenz, Guanoxan Sulfate, Guanoxyfen Sulfate, Gusperimus Trihydrochloride, Halazepam, Halcinonide, halichondrin B, Halobetasol Propionate, halofantrine, Halofantrine Hydrochloride, Halofenate, Halofuginone Hydrobromide, halomon, Halopemide, Haloperidol, halopredone, Haloprogesterone, Haloprogin, Halothane, Halquinols, Hamycin, Han memopausal gonadotropins, hatomamicin, hatomarubigin A, hatomarubigin B, hatomarubigin C, hatomarubigin D, Heparin Sodium, hepsulfam, heregulin, Hetacillin, Heteronium Bromide, Hexachlorophene: Hydrogen Peroxide, Hexafluorenium Bromide, hexamethylene bisacetamide, Hexedine, Hexobendine, Hexoprenaline Sulfate, Hexylresorcinol, Histamine Phosphate, Histidine, Histoplasmin, Histrelin, Homatropine Hydrobromide, Hoquizil Hydrochloride, Human chorionic gonadotropin, Hycanthone, Hydralazine Hydrochloride, Hydralazine Polistirex, Hydrochlorothiazide, Hydrocodone Bitartrate, Hydrocortisone, Hydroflumethiazide, Hydromorphone Hydrochloride, Hydroxyamphetamine Hydrobromide, Hydroxychloroquine Sulfate, Hydroxyphenamate, Hydroxyprogesterone Caproate, Hydroxyurea, Hydroxyzine Hydrochloride, Hymecromone, Hyoscyamine, hypericin, Ibafloxacin, ibandronic acid, ibogaine, Ibopamine, ibudilast, Ibufenac, Ibuprofen, Ibutilide Fumarate, Icatibant Acetate, Ichthammol, Icotidine, idarubicin, idoxifene, Idoxuridine, idramantone, Iemefloxacin, Iesopitron, Ifetroban, Ifosfamide, Ilepeimide, illimaquinone, ilmofosine, ilomastat, Ilonidap, iloperidone, iloprost, Imafen Hydrochloride, Imazodan Hydrochloride, imidapril, imidazenil, imidazoacridones, Imidecyl Iodine, Imidocarb Hydrochloride, Imidoline Hydrochloride, Imidurea, Imiloxan Hydrochloride, Imipenem, Imipramine Hydrochloride, imiquimod, immunostimulant peptides, Impromidine Hydrochloride, Indacrinone, Indapamide, Indecainide Hydrochloride, Indeloxazine Hydrochloride, Indigotindisulfonate Sodium, indinavir, Indocyanine Green, Indolapril Hydrochloride, Indolidan, indometacin, Indomethacin Sodium, Indoprofen, indoramin, Indorenate Hydrochloride, Indoxole, Indriline Hydrochloride, inocoterone, inogatran, inolimomab, Inositol Niacinate, Insulin, interferons, interleukins, Intrazole, Intriptyline Hydrochloride, iobenguane, Iobenzamic Acid, iobitridol, Iocarmate Meglumine, Iocarmic Acid, Iocetamic Acid, Iodamide, Iodine, Iodipamide Meglumine, Iodixanol, iodoamiloride, Iodoantipyrine I 131, Iodocholesterol I 131, iododoxorubicin, Iodohippurate Sodium I 131, Iodopyracet I 125, Iodoquinol, Iodoxamate Meglumine, Iodoxamie Acid, Ioglicic Acid, Iofetamine Hydrochloride I 123, iofratol, Ioglucol, Ioglucomide, Ioglycamic Acid, Iogulamide, Iohexol, iomeprol, Iomethin I 125, Iopamidol, Iopanoic Acid, iopentol, Iophendylate, Ioprocemic Acid, iopromide, Iopronic Acid, Iopydol, Iopydone, iopyrol, Iosefamic Acid, Ioseric Acid, Iosulamide Meglumine, Iosumetic Acid, Iotasul, Iotetric Acid, Iothalamate Sodium, Iothalamic Acid, iotriside, Iotrolan, Iotroxic Acid, Iotyrosine I 131, Ioversol, Ioxagiate Sodium, Ioxaglate Meglumine, Ioxaglic Acid, ioxilan, Ioxotrizoic Acid, ipazilide, ipenoxazone, ipidacrine, Ipodate Calcium, ipomeanol, 4-, Ipratropium Bromide, ipriflavone, Iprindole, Iprofenin, Ipronidazole, Iproplatin, Iproxamine Hydrochloride, ipsapirone, irbesartan, irinotecan, irloxacin, iroplact, irsogladine, Irtemazole, isalsteine, Isamoxole, isbogrel, Isepamicin, isobengazole, Isobutamben, Isocarboxazid, Isoconazole, Isoetharine, isofloxythepin, Isoflupredone Acetate, Isoflurane, Isoflurophate, isohomohalicondrin B, Isoleucine, Isomazole Hydrochloride, Isomylamine Hydrochloride, Isoniazid, Isopropamide Iodide, Isopropyl Alcohol, isopropyl unoprostone, Isoproterenol Hydrochloride, Isosorbide, Isosorbide Mononitrate, Isotiquimide, Isotretinoin, Isoxepac, Isoxicam, Isoxsuprine Hydrochloride, isradipine, itameline, itasetron, Itazigrel, itopride, Itraconazole, Ivermectin, jasplakinolide, Josamycin, kahalalide F, Kalafungin, Kanamycin Sulfate, Ketamine Hydrochloride, Ketanserin, Ketazocine, Ketazolam, Kethoxal, Ketipramine Fumarate, Ketoconazole, Ketoprofen, Ketorfanol, ketorolac, Ketotifen Fumarate, Kitasamycin, Labetalol Hydrochloride, Lacidipine, lacidipine, lactitol, lactivicin, laennec, lafutidine, lamellarin-N triacetate, lamifiban, Lamivudine, Lamotrigine, lanoconazole, Lanoxin, lanperisone, lanreotide, Lansoprazole, latanoprost, lateritin, laurocapram, Lauryl Isoquinolinium Bromide, Lavoltidine Succinate, lazabemide, Lecimibide, leinamycin, lemildipine, leminoprazole, lenercept, Leniquinsin, lenograstim, Lenperone, lentinan sulfate, leptin, leptolstatin, lercanidipine, Lergotrile, lerisetron, Letimide Hydrochloride, letrazuril, letrozole, Leucine, leucomyzin, Leuprolide Acetate, leuprolide+estrogen+progesterone, leuprorelin, Levamfetamine Succinate, levamisole, Levdobutamine Lactobionate, Leveromakalim, levetiracetam, Leveycloserine, levobetaxolol, levobunolol, levobupivacaine, levocabastine, levocarnitine, Levodopa, levodropropizine, levofloxacin, Levofuraltadone, Levoleucovorin Calcium, Levomethadyl Acetate, Levomethadyl Acetate Hydrochloride, levomoprolol, Levonantradol Hydrochloride, Levonordefrin, Levonorgestrel, Levopropoxyphene Napsylate, Levopropylcillin Potassium, levormeloxifene, Levorphanol Tartrate, levosimendan, levosulpiride, Levothyroxine Sodium, Levoxadrol Hydrochloride, Lexipafant, Lexithromycin, liarozole, Libenzapril, Lidamidine Hydrochloride, Lidocaine, Lidofenin, Lidoflazine, Lifarizine, Lifibrate, Lifibrol, Linarotene, Lincomycin, linear polyamine analogue, Linogliride, Linopirdine, linotroban, linsidomine, lintitript, lintopride, Liothyronine I 125, liothyronine sodium, Liotrix, lirexapride, lisinopril, lissoclinamide 7, Lixazinone Sulfate, lobaplatin, Lobenzarit Sodium, Lobucavir, Lodelaben, Iodoxamide, Lofemizole Hydrochloride, Lofentanil Oxalate, Lofepramine Hydrochloride, Lofexidine Hydrochloride, lombricine, Lomefloxacin, lomerizine, Lometraline Hydrochloride, lometrexol, Lomofungin, Lomoxicam, Lomustine, Lonapalene, lonazolac, lonidamine, Loperamide Hydrochloride, loracarbef, Lorajmine Hydrochloride, loratadine, Lorazepam, Lorbamate, Lorcainide Hydrochloride, Loreclezole, Loreinadol, lorglumide, Lormetazepam, Lornoxicam, lornoxicam, Lortalamine, Lorzafone, losartan, losigamone, losoxantrone, Losulazine Hydrochloride, loteprednol, lovastatin, loviride, Loxapine, Loxoribine, lubeluzole, Lucanthone Hydrochloride, Lufironil, Lurosetron Mesylate, lurtotecan, luteinizing hormone, lutetium, Lutrelin Acetate, luzindole, Lyapolate Sodium, Lycetamine, lydicamycin, Lydimycin, Lynestrenol, Lypressin, Lysine, lysofylline, lysostaphin, lytic peptides, Maduramicin, Mafenide, magainin 2 amide, Magnesium Salicylate, Magnesium Sulfate, magnolol, maitansine, Malethamer, mallotochromene, mallotojaponin, Malotilate, malotilate, mangafodipir, manidipine, maniwamycin A, Mannitol, mannostatin A, manumycin E, manumycin F, mapinastine, Maprotiline, marimastat, Martek 8708, Martek 92211, Masoprocol, maspin, massetolide, matrylysin inhibitors, Maytansine, Mazapertine Succiniate, Mazindol, Mebendazole, Mebeverine Hydrochloride, Mebrofenin, Mebutamate, Mecamylamine Hydrochloride, Mechlorethamine Hydrochloride, Meclocycline, Meclofenamate Sodium, Mecloqualone, Meclorisone Dibutyrate, Medazepam Hydrochloride, Medorinone, Medrogestone, Medroxalol, Medroxyprogesterone, Medrysone, Meelizine Hydrochloride, Mefenamic Acid, Mefenidil, Mefenorex Hydrochloride, Mefexamide, Mefloquine Hydrochloride, Mefruside, Megalomicin Potassium Phosphate, Megestrol Acetate, Meglumine, Meglutol, Melengestrol Acetate, Melitracen Hydrochloride, Melphalan, Memotine Hydrochloride, Menabitan Hydrochloride, Menoctone, menogaril, Menotropins, Meobentine Sulfate, Mepartricin, Mepenzolate Bromide, Meperidine Hydrochloride, Mephentermine Sulfate, Mephenyloin, Mephobarbital, Mepivacaine Hydrochloride, Meprobamate, Meptazinol Hydrochloride, Mequidox, Meralein Sodium, merbarone, Mercaptopurine, Mercufenol Chloride, Mercury, Ammoniated, Merisoprol Hg 197, Meropenem, Mesalamine, Meseclazone, Mesoridazine, Mesterolone, Mestranol, Mesuprine Hydrochloride, Metalol Hydrochloride, Metaproterenol Polistirex, Metaraminol Bitartrate, Metaxalone, Meteneprost, meterelin, Metformin, Methacholine Chloride, Methacycline, Methadone Hydrochloride, Methadyl Acetate, Methalthiazide, Methamphetamine Hydrochloride, Methaqualone, Methazolamide, Methdilazine, Methenamine, Methenolone Acetate, Methetoin, Methicillin Sodium, Methimazole, methioninase, Methionine, Methisazone, Methixene Hydrochloride, Methocarbamol, Methohexital Sodium, Methopholine, Methotrexate, Methotrimeprazine, methoxatone, Methoxyflurane, Methsuximide, Methyclothiazide, Methyl Palmoxirate, Methylatropine Nitrate, Methylbenzethonium Chloride, Methyldopa, Methyldopate Hydrochloride, Methylene Blue, Methylergonovine Maleate, methylhistamine, R-alpha, methylinosine monophosphate, Methylphenidate Hydrochloride, Methylprednisolone, Methyltestosterone, Methynodiol Diacelate, Methysergide, Methysergide Maleate, Metiamide, Metiapine, Metioprim, metipamide, Metipranolol, Metizoline Hydrochloride, Metkephamid Acetate, metoclopramide, Metocurine Iodide, Metogest, Metolazone, Metopimazine, Metoprine, Metoprolol, Metoquizine, metrifonate, Metrizamide, Metrizoate Sodium, Metronidazole, Meturedepa, Metyrapone, Metyrosine, Mexiletine Hydrochloride, Mexrenoate Potassium, Mezlocillin, mfonelic Acid, Mianserin Hydrochloride, mibefradil, Mibefradil Dihydrochloride, Mibolerone, michellamine B, Miconazole, microcolin A, Midaflur, Midazolam Hydrochloride, midodrine, mifepristone, Mifobate, miglitol, milacemide, milameline, mildronate, Milenperone, Milipertine, milnacipran, Milrinone, miltefosine, Mimbane Hydrochloride, minaprine, Minaxolone, Minocromil, Minocycline, Minoxidil, Mioflazine Hydrochloride, miokamycin, mipragoside, mirfentanil, mirimostim, Mirincamycin Hydrochloride, Mirisetron Maleate, Mirtazapine, mismatched double stranded RNA, Misonidazole, Misoprostol, Mitindomide, Mitocarcin, Mitocromin, Mitogillin, mitoguazone, mitolactol, Mitomalcin, Mitomycin, mitonafide, Mitosper, Mitotane, mitoxantrone, mivacurium chloride, mivazerol, mixanpril, Mixidine, mizolastine, mizoribine, Moclobemide, modafinil, Modaline Sulfate, Modecainide, moexipril, mofarotene, Mofegiline Hydrochloride, mofezolac, molgramostim, Molinazone, Molindone Hydrochloride, Molsidomine, mometasone, Monatepil Maleate, Monensin, Monoctanoin, Montelukast Sodium, montirelin, mopidamol, moracizine, Morantel Tartrate, Moricizine, Morniflumate, Morphine Sulfate, Morrhuate Sodium, mosapramine, mosapride, motilide, Motretinide, Moxalactam Disodium, Moxazocine, moxiraprine, Moxnidazole, moxonidine, Mumps Skin Test Antigen, mustard anticancer agent, Muzolimine, mycaperoxide B, Mycophenolic Acid, myriaporone, Nabazenil, Nabilone, Nabitan Hydrochloride, Naboctate Hydrochloride, Nabumetone, N-acetyldinaline, Nadide, nadifloxacin, Nadolol, nadroparin calcium, nafadotride, nafamostat, nafarelin, Nafcillin Sodium, Nafenopin, Naf imidone Hydrochloride, Naflocort, Nafomine Malate, Nafoxidine Hydrochloride, Nafronyl Oxalate, Naftifine Hydrochloride, naftopidil, naglivan, nagrestip, Nalbuphine Hydrochloride, Nalidixate Sodium, Nalidixic Acid, nalmefene, Nalmexone Hydrochloride, naloxone+pentazocine, Naltrexone, Namoxyrate, Nandrolone Phenpropionate, Nantradol Hydrochloride, Napactadine Hydrochloride, napadisilate, Napamezole Hydrochloride, napaviin, Naphazoline Hydrochloride, naphterpin, Naproxen, Naproxol, napsagatran, Naranol Hydrochloride, Narasin, naratriptan, nartograstim, nasaruplase, Natamycin, nateplase, Naxagolide Hydrochloride, Nebivolol, Nebramycin, nedaplatin, Nedocromil, Nefazodone Hydrochloride, Neflumozide Hydrochloride, Nefopam Hydrochloride, Nelezaprine Maleate, Nemazoline Hydrochloride, nemorubicin, Neomycin Palmitate, Neostigmine Bromide, neridronic acid, Netilmicin Sulfate, neutral endopeptidase, Neutramycin, Nevirapine, Nexeridine Hydrochloride, Niacin, Nibroxane, Nicardipine Hydrochloride, Nicergoline, Niclosamide, Nicorandil, Nicotinyl Alcohol, Nifedipine, Nifirmerone, Nifluridide, Nifuradene, Nifuraldezone, Nifuratel, Nifuratrone, Nifurdazil, Nifurimide, Nifurpirinol, Nifurquinazol, Nifurthiazole, nilutamide, Nilvadipine, Nimazone, Nimodipine, niperotidine, niravoline, Niridazole, nisamycin, Nisbuterol Mesylate, nisin, Nisobamate, Nisoldipine, Nisoxetine, Nisterime Acetate, Nitarsone, nitazoxamide, nitecapone, Nitrafudam Hydrochloride, Nitralamine Hydrochloride, Nitramisole Hydrochloride, Nitrazepam, Nitrendipine, Nitrocycline, Nitrodan, Nitrofurantoin, Nitrofurazone, Nitroglycerin, Nitromersol, Nitromide, Nitromifene Citrate, Nitrous Oxide, nitroxide antioxidant, nitrullyn, Nivazol, Nivimedone Sodium, Nizatidine, Noberastine, Nocodazole, Nogalamycin, Nolinium Bromide, Nomifensine Maleate, Noracymethadol Hydrochloride, Norbolethone, Norepinephrine Bitartrate, Norethindrone, Norethynodrel, Norfloxacin, Norflurane, Norgestimate, Norgestomet, Norgestrel, Nortriptyline Hydrochloride, Noscapine, Novobiocin Sodium, N-substituted benzaimides, Nufenoxole, Nylestriol, Nystatin, O6-benzylguanine, Obidoxime Chloride, Ocaperidone, Ocfentanil Hydrochloride, Ocinaplon, Octanoic Acid, Octazamide, Octenidine Hydrochloride, Octodrine, Octreotide, Octriptyline Phosphate, Ofloxacin, Oformine, okicenone, Olanzapine, oligonucleotides, olopatadine, olprinone, olsalazine, Olsalazine Sodium, Olvanil, omeprazole, onapristone, ondansetron, Ontazolast, Oocyte maturation inhibitor, Opipramol Hydrochloride, oracin, Orconazole Nitrate, Orgotein, Orlislat, Ormaplatin, Ormetoprim, Ornidazole, Orpanoxin, Orphenadrine Citrate, osaterone, otenzepad, Oxacillin Sodium, Oxagrelate, oxaliplatin, Oxamarin Hydrochloride, oxamisole, Oxamniquine, oxandrolone, Oxantel Pamoate, Oxaprotiline Hydrochloride, Oxaprozin, Oxarbazole, Oxatomide, oxaunomycin, Oxazepam, oxcarbazepine, Oxendolone, Oxethazaine, Oxetorone Fumarate, Oxfendazole, Oxfenicine, Oxibendazole, oxiconazole, Oxidopamine, Oxidronic Acid, Oxifungin Hydrochloride, Oxilorphan, Oximonam, Oximonam Sodium, Oxiperomide, oxiracetam, Oxiramide, Oxisuran, Oxmetidine Hydrochloride, oxodipine, Oxogestone Phenpropionate, Oxolinic Acid, Oxprenolol Hydrochloride, Oxtriphylline, Oxybutynin Chloride, Oxychlorosene, Oxycodone, Oxymetazoline Hydrochloride, Oxymetholone, Oxymorphone Hydrochloride, Oxypertine, Oxyphenbutazone, Oxypurinol, Oxytetracycline, Oxytocin, ozagrel, Ozolinone, Paclitaxel, palauamine, Paldimycin, palinavir, palmitoylrhizoxin, Palmoxirate Sodium, pamaqueside, Pamatolol Sulfate, pamicogrel, Pamidronate Disodium, pamidronic acid, Panadiplon, panamesine, panaxytriol, Pancopride, Pancuronium Bromide, panipenem, pannorin, panomifene, pantethine, pantoprazole, Papaverine Hydrochloride, parabactin, Parachlorophenol, Paraldehyde, Paramethasone Acetate, Paranyline Hydrochloride, Parapenzolate Bromide, Pararosaniline Pamoate, Parbendazole, Parconazole Hydrochloride, Paregoric, Pareptide Sulfate, Pargyline Hydrochloride, parnaparin sodium, Paromomycin Sulfate, Paroxetine, parthenolide, Partricin, Paulomycin, pazelliptine, Pazinaclone, Pazoxide, pazufloxacin, pefloxacin, pegaspargase, Pegorgotein, Pelanserin Hydrochloride, peldesine, Peliomycin, Pelretin, Pelrinone Hydrochloride, Pemedolac, Pemerid Nitrate, pemirolast, Pemoline, Penamecillin, Penbutolol Sulfate, Penciclovir, Penfluridol, Penicillin G Benzathine, Penicillin G Potassium, Penicillin G Procaine, Penicillin G Sodium, Penicillin V, Penicillin V Benzathine, Penicillin V Hydrabamine, Penicillin V Potassium, Pentabamate, Pentaerythritol Tetranitrate, pentafuside, pentamidine, pentamorphone, Pentamustine, Pentapiperium Methylsulfate, Pentazocine, Pentetic Acid, Pentiapine Maleate, pentigetide, Pentisomicin, Pentizidone Sodium, Pentobarbital, Pentomone, Pentopril, pentosan, pentostatin, Pentoxifylline, Pentrinitrol, pentrozole, Peplomycin Sulfate, Pepstatin, perflubron, perfofamide, Perfosfamide, pergolide, Perhexiline Maleate, perillyl alcohol, Perindopril, perindoprilat, Perlapine, Permethrin, perospirone, Perphenazine, Phenacemide, phenaridine, phenazinomycin, Phenazopyridine Hydrochloride, Phenbutazone Sodium Glycerate, Phencarbamide, Phencyclidine Hydrochloride, Phendimetrazine Tartrate, Phenelzine Sulfate, Phenmetrazine Hydrochloride, Phenobarbital, Phenoxybenzamine Hydrochloride, Phenprocoumon, phenserine, phensuccinal, Phensuximide, Phentermine, Phentermine Hydrochloride, phentolamine mesilate, Phentoxifylline, Phenyl Aminosalicylate, phenylacetate, Phenylalanine, phenylalanyl ketoconazole, Phenylbutazone, Phenylephrine Hydrochloride, Phenylpropanolamine Hydrochloride, Phenylpropanolamine Polistirex, Phenyramidol Hydrochloride, Phenyloin, phosphatase inhibitors, Physostigmine, picenadol, picibanil, Picotrin Diolamine, picroliv, picumeterol, pidotimod, Pifamine, Pilocarpine, pilsicainide, pimagedine, Pimetine Hydrochloride, pimilprost, Pimobendan, Pimozide, Pinacidil, Pinadoline, Pindolol, pinnenol, pinocebrin, Pinoxepin Hydrochloride, pioglitazone, Pipamperone, Pipazethate, pipecuronium bromide, Piperacetazine, Piperacillin Sodium, Piperamide Maleate, piperazine, Pipobroman, Piposulfan, Pipotiazine Palmitate, Pipoxolan Hydrochloride, Piprozolin, Piquindone Hydrochloride, Piquizil Hydrochloride, Piracetam, Pirandamine Hydrochloride, pirarubicin, Pirazmonam Sodium, Pirazolac, Pirbenicillin Sodium, Pirbuterol Acetate, Pirenperone, Pirenzepine Hydrochloride, piretamide, Pirfenidone, Piridicillin Sodium, Piridronate Sodium, Piriprost, piritrexim, Pirlimycin Hydrochloride, pirlindole, pirmagrel, Pirmenol Hydrochloride, Pirnabine, Piroctone, Pirodavir, pirodomast, Pirogliride Tartrate, Pirolate, Pirolazamide, Piroxantrone Hydrochloride, Piroxicam, Piroximone, Pirprofen, Pirquinozol, Pirsidomine, Prenylamine, Pituitary, Posterior, Pivampicillin Hydrochloride, Pivopril, Pizotyline, placetin A, platinum compounds, platinum-triamine complex, Plicamycin, Plomestane, Pobilukast Edamine, Podofilox, Poisonoak Extract, Poldine Methylsulfate, Poliglusam, Polignate Sodium, Polymyxin B Sulfate, Polythiazide, Ponalrestat, Porfimer Sodium, Porfiromycin, Potassium Chloride, Potassium Iodide, Potassium Permanganate, Povidone-Iodine, Practolol, Pralidoxime Chloride, Pramiracetam Hydrochloride, Pramoxine Hydrochloride, Pranolium Chloride, Pravadoline Maleate, Pravastatin (Pravachol), Prazepam, Prazosin, Prazosin Hydrochloride, Prednazate, Prednicarbate, Prednimustine, Prednisolone, Prednisone, Prednival, Pregnenolone Succiniate, Prenalterol Hydrochloride, Pridefine Hydrochloride, Prifelone, Prilocalne Hydrochloride, Prilosec, Primaquine Phosphate, Primidolol, Primidone, Prinivil, Prinomide Tromethamine, Prinoxodan, Prizidilol Hydrochloride, Proadifen Hydrochloride, Probenecid, Probicromil Calcium, Probucol, Procainamide Hydrochloride, Procaine Hydrochloride, Procarbazine Hydrochloride, Procaterol Hydrochloride, Prochlorperazine, Procinonide, Proclonol, Procyclidine Hydrochloride, Prodilidine Hydrochloride, Prodolic Acid, Profadol Hydrochloride, Progabide, Progesterone, Proglumide, Proinsulin Human, Proline, Prolintane Hydrochloride, Promazine Hydrochloride, Promethazine Hydrochloride, Propafenone Hydrochloride, propagermanium, Propanidid, Propantheline Bromide, Proparacaine Hydrochloride, Propatyl Nitrate, propentofylline, Propenzolate Hydrochloride, Propikacin, Propiomazine, Propionic Acid, propionylcarnitine, L-, propiram, propiram+paracetamol, propiverine, Propofol, Propoxycaine Hydrochloride, Propoxyphene Hydrochloride, Propranolol Hydrochloride, Propulsid, propyl bis-acridone, Propylhexedrine, Propyliodone, Propylthiouracil, Proquazone, Prorenoate Potassium, Proroxan Hydrochloride, Proscillaridin, Prostalene, prostratin, Protamine Sulfate, protegrin, Protirelin, protosufloxacin, Protriptyline Hydrochloride, Proxazole, Proxazole Citrate, Proxicromil, Proxorphan Tartrate, prulifloxacin, Pseudoephedrine Hydrochloride, Puromycin, purpurins, Pyrabrom, Pyrantel Pamoate, Pyrazinamide, Pyrazofurin, pyrazoloacridine, Pyridostigmine Bromide, Pyrilamine Maleate, Pyrimethamine, Pyrinoline, Pyrithione Sodium, Pyrithione Zinc, Pyrovalerone Hydrochloride, Pyroxamine Maleate, Pyrrocaine, Pyrroliphene Hydrochloride, Pyrrolnitrin, Pyrvinium Pamoate, Quadazocine Mesylate, Quazepam, Quazinone, Quazodine, Quazolast, quetiapine, quiflapon, quinagolide, Quinaldine Blue, quinapril, Quinaprilat, Quinazosin Hydrochloride, Quinbolone, Quinctolate, Quindecamine Acetate, Quindonium Bromide, Quinelorane Hydrochloride, Quinestrol, Quinfamide, Quingestanol Acetate, Quingestrone, Quinidine Gluconate, Quinielorane Hydrochloride, Quinine Sulfate, Quinpirole Hydrochloride, Quinterenol Sulfate, Quinuclium Bromide, Quinupristin, Quipazine Maleate, Rabeprazole Sodium, Racephenicol, Racepinephrine, raf antagonists, Rafoxamide, Ralitoline, raloxifene, raltitrexed, ramatroban, Ramipril, Ramoplanin, ramosetron, ranelic acid, Ranimycin, Ranitidine, ranolazine, Rauwolfia Serpentina, recainam, Recainam Hydrochloride, Reclazepam, regavirumab, Regramostim, Relaxin, Relomycin, Remacemide Hydrochloride, Remifentanil Hydrochloride, Remiprostol, Remoxipride, Repirinast, Repromicin, Reproterol Hydrochloride, Reserpine, resinferatoxin, Resorcinol, retelliptine demethylated, reticulon, reviparin sodium, revizinone, rhenium Re 186 etidronate, rhizoxin, Ribaminol, Ribavirin, Riboprine, ribozymes, ricasetron, Ridogrel, Rifabutin, Rifametane, Rifamexil, Rifamide, Rifampin, Rifapentine, Rifaximin, RII retinamide, rilopirox, Riluzole, rimantadine, Rimcazole Hydrochloride, Rimexolone, Rimiterol Hydrobromide, rimoprogin, riodipine, Rioprostil, Ripazepam, ripisartan, Risedronate Sodium, risedronic acid, Risocaine, Risotilide Hydrochloride, rispenzepine, Risperdal, Risperidone, Ritanserin, ritipenem, Ritodrine, Ritolukast, ritonavir, rizatriptan benzoate, Rocastine Hydrochloride, Rocuronium Bromide, Rodocaine, Roflurane, Rogletimide, rohitukine, rokitamycin, Roletamicide, Rolgamidine, Rolicyprine, Rolipram, Rolitetracycline, Rolodine, Romazarit, romurtide, Ronidazole, ropinirole, Ropitoin Hydrochloride, ropivacaine, Ropizine, roquinimex, Rosaramicin, Rosoxacin, Rotoxamine, roxaitidine, Roxarsone, roxindole, roxithromycin, rubiginone B1, ruboxyl, rufloxacin, rupatidine, Rutamycin, ruzadolane, Sabeluzole, safingol, safironil, saintopin, salbutamol, R-Salcolex, Salethamide Maleate, Salicyl Alcohol, Salicylamide, Salicylate Meglumine, Salicylic Acid, Salmeterol, Salnacediin, Salsalate, sameridine, sampatrilat, Sancycline, sanfetrinem, Sanguinarium Chloride, Saperconazole, saprisartan, sapropterin, saquinavir, Sarafloxacin Hydrochloride, Saralasin Acetate, SarCNU, sarcophytol A, sargramostim, Sarmoxicillin, Sarpicillin, sarpogrelate, saruplase, saterinone, satigrel, satumomab pendetide, Schick Test Control, Scopafungin, Scopolamine Hydrobromide, Scrazaipine Hydrochloride, Sdi 1 mimetics, Secalciferol, Secobarbital, Seelzone, Seglitide Acetate, selegiline, Selegiline Hydrochloride, Selenium Sulfide, Selenomethionine Se 75, Selfotel, sematilide, semduramicin, semotiadil, semustine, sense oligonucleotides, Sepazonium Chloride, Seperidol Hydrochloride, Seprilose, Seproxetine Hydrochloride, Seractide Acetate, Sergolexole Maleate, Serine, Sermetacin, Sermorelin Acetate, sertaconazole, sertindole, sertraline, setiptiline, Setoperone, sevirumab, sevoflurane, sezolamide, Sibopirdine, Sibutramine Hydrochloride, signal transduction inhibitors, Silandrone, silipide, silteplase, Silver Nitrate, simendan, Simtrazene, Simvastatin, Sincalide, Sinefungin, sinitrodil, sinnabidol, sipatrigine, sirolimus, Sisomicin, Sitogluside, sizofiran, sobuzoxane, Sodium Amylosulfate, Sodium Iodide I 123, Sodium Nitroprusside, Sodium Oxybate, sodium phenylacetate, Sodium Salicylate, solverol, Solypertine Tartrate, Somalapor, Somantadine Hydrochloride, somatomedin B, somatomedin C, somatrem, somatropin, Somenopor, Somidobove, sonermin, Sorbinil, Sorivudine, sotalol, Soterenol Hydrochloride, Sparfloxacin, Sparfosate Sodium, sparfosic acid, Sparsomycin, Sparteine Sulfate, Spectinomycin Hydrochloride, spicamycin D, Spiperone, Spiradoline Mesylate, Spiramycin, Spirapril Hydrochloride, Spiraprilat, Spirogermanium Hydrochloride, Spiromustine, Spironolactone, Spiroplatin, Spiroxasone, splenopentin, spongistatin 1, Sprodiamide, squalamine, Stallimycin Hydrochloride, Stannous Pyrophosphate, Stannous Sulfur Colloid, Stanozolol, Statolon, staurosporine, stavudine, Steffimycin, Stenbolone Acetate, stepronin, Stilbazium Iodide, Stilonium Iodide, stipiamide, Stiripentol, stobadine, Streptomycin Sulfate, Streptonicozid, Streptonigrin, Streptozocin, stromelysin inhibitors, Strontium Chloride Sr 89, succibun, Succimer, Succinylcholine Chloride, Sucralfate, Sucrosofate Potassium, Sudoxicam, Sufentanil, Sufotidine, Sulazepam, Sulbactam Pivoxil, Sulconazole Nitrate, Sulfabenz, Sulfabenzamide, Sulfacetamide, Sulfacytine, Sulfadiazine, Sulfadoxine, Sulfalene, Sulfamerazine, Sulfameter, Sulfamethazine, Sulfamethizole, Sulfamethoxazole, Sulfamonomethoxine, Sulfamoxole, Sulfanilate Zinc, Sulfanitran, sulfasalazine, Sulfasomizole, Sulfazamet, Sulfinalol Hydrochloride, sulfinosine, Sulfinpyrazone, Sulfisoxazole, Sulfomyxin, Sulfonterol Hydrochloride, sulfoxamine, Sulinldac, Sulmarin, Sulnidazole, Suloctidil, Sulofenur, sulopenem, Suloxifen Oxalate, Sulpiride, Sulprostone, sultamicillin, Sulthiame, sultopride, sulukast, Sumarotene, sumatriptan, Suncillin Sodium, Suproclone, Suprofen, suradista, suramin, Surfomer, Suricainide Maleate, Suritozole, Suronacrine Maleate, Suxemerid Sulfate, swainsonine, symakalim, Symclosene, Symetine Hydrochloride, synthetic glycosaminoglycans, Taciamine Hydrochloride, Tacrine Hydrochloride, Tacrolimus, Talampicillin Hydrochloride, Taleranol, Talisomycin, tallimustine, Talmetacin, Talniflumate, Talopram Hydrochloride, Talosalate, Tametraline Hydrochloride, Tamoxifen, Tampramine Fumarate, Tamsulosin Hydrochloride, Tandamine Hydrochloride, tandospirone, tapgen, taprostene, Tasosartan, tauromustine, Taxane, Taxoid, Tazadolene Succinate, tazanolast, tazarotene, Tazifylline Hydrochloride, Tazobactam, Tazofelone, Tazolol Hydrochloride, Tebufelone, Tebuquine, Technetium Tc 99 m Bicisate, Teclozan, Tecogalan Sodium, Teecleukin, Teflurane, Tegafur, Tegretol, Teicoplanin, telenzepine, tellurapyrylium, telmesteine, telmisartan, telomerase inhibitors, Teloxantrone Hydrochloride, Teludipine Hydrochloride, Temafloxacin Hydrochloride, Tematropium Methyl sulfate, Temazepam, Temelastine, temocapril, Temocillin, temoporfin, temozolomide, Tenidap, Teniposide, tenosal, tenoxicam, tepirindole, Tepoxalin, Teprotide, terazosin, Terbinafine, Terbutaline Sulfate, Terconazole, terfenadine, terflavoxate, terguride, Teriparatide Acetate, terlakiren, terlipressin, terodiline, Teroxalene Hydrochloride, Teroxirone, tertatolol, Tesicam, Tesimide, Testolactone, Testosterone, Tetracaine, tetrachlorodecaoxide, Tetracycline, Tetrahydrozoline Hydrochloride, Tetramisole Hydrochloride, Tetrazolast Meglumine, tetrazomine, Tetrofosmin, Tetroquinone, Tetroxoprim, Tetrydamine, thaliblastine, Thalidomide, Theofibrate, Theophylline, Thiabendazole, Thiamiprine, Thiamphenicol, Thiamylal, Thiazesim Hydrochloride, Thiazinamium Chloride, Thiethylperazine, Thimerfonate Sodium, Thimerosal, thiocoraline, thiofedrine, Thioguanine, thiomarinol, Thiopental Sodium, thioperamide, Thioridazine, Thiotepa, Thiothixene, Thiphenamil Hydrochloride, Thiphencillin Potassium, Thiram, Thozalinone, Threonine, Thrombin, thrombopoietin, thrombopoietin mimetic, thymalfasin, thymopoietin receptor agonist, thymotrinan, Thyromedan Hydrochloride, Thyroxine 1 125, Thyroxine 1 131, Tiacrilast, Tiacrilast Sodium, tiagabine, Tiamenidine, tianeptine, tiapafant, Tiapamil Hydrochloride, Tiaramide Hydrochloride, Tiazofurin, Tibenelast Sodium, Tibolone, Tibric Acid, Ticabesone Propionate, Ticarbodine, Ticarcillin Cresyl Sodium, Ticlatone, ticlopidine, Ticrynafen, tienoxolol, Tifurac Sodium, Tigemonam Dicholine, Tigestol, Tiletamine Hydrochloride, Tilidine Hydrochloride, tilisolol, tilnoprofen arbamel, Tilorone Hydrochloride, Tiludronate Disodium, tiludronic acid, Timefurone, Timobesone Acetate, Timolol, tin ethyl etiopurpurin, Tinabinol, Timidazole, Tinzaparin Sodium, Tioconazole, Tiodazosin, Tiodonium Chloride, Tioperidone Hydrochloride, Tiopinac, Tiospirone Hydrochloride, Tiotidine, tiotropium bromide, Tioxidazole, Tipentosin Hydrochloride, Tipredane, Tiprenolol Hydrochloride, Tiprinast Meglumine, Tipropidil Hydrochloride, Tiqueside, Tiquinamide Hydrochloride, tirandalydigin, Tirapazamine, tirilazad, tirofiban, tiropramide, titanocene dichloride, Tixanox, Tixocortol Pivalate, Tizanidine Hydrochloride, Tobramycin, Tocainide, Tocamphyl, Tofenacin Hydrochloride, Tolamolol, Tolazamide, Tolazoline Hydrochloride, Tolbutamide, Tolcapone, Tolciclate, Tolfamide, Tolgabide, lamotrigine, Tolimidone, Tolindate, Tolmetin, Tolnaftate, Tolpovidone 1 131, Tolpyrramide, Tolrestat, Tomelukast, Tomoxetine Hydrochloride, Tonazocine Mesylate, Topiramate, topotecan, Topotecan Hydrochloride, topsentin, Topterone, Toquizine, torasemide, toremifene, Torsemide, Tosifen, Tosufloxacin, totipotent stem cell factor, Tracazolate, trafermin, Tralonide, Tramadol Hydrochloride, Tramazoline Hydrochloride, trandolapril, Tranexamic Acid, Tranilast, Transcainide, translation inhibitors, traxanox, Trazodone Hydrochloride, Trazodone-HCL, Trebenzomine Hydrochloride, Trefentanil Hydrochloride, Treloxinate, Trepipam Maleate, Trestolone Acetate, tretinoin, Triacetin, triacetyluridine, Triafungin, Triamcinolone, Triampyzine Sulfate, Triamterene, Triazolam, Tribenoside, tricaprilin, Tricetamide, Trichlormethiazide, trichohyalin, triciribine, Tricitrates, Triclofenol piperazine, Triclofos Sodium, Triclonide, trientine, Trifenagrel, triflavin, Triflocin, Triflubazam, Triflumidate, Trifluoperazine Hydrochloride, Trifluperidol, Triflupromazine, Triflupromazine Hydrochloride, Trifluridine, Trihexyphenidyl Hydrochloride, Trilostane, Trimazosin Hydrochloride, trimegestone, Trimeprazine Tartrate, Trimethadione, Trimethaphan Camsylate, Trimethobenzamide Hydrochloride, Trimethoprim, Trimetozine, Trimetrexate, Trimipramine, Trimoprostil, Trimoxamine Hydrochloride, Triolein 1 125, Triolein 1 131, Trioxifene Mesylate, Tripamide, Tripelennamine Hydrochloride, Triprolidine Hydrochloride, Triptorelin, Trisulfapyrimidines, Troclosene Potassium, troglitazone, Trolamine, Troleandomycin, trombodipine, trometamol, Tropanserin Hydrochloride, Tropicamide, tropine ester, tropisetron, trospectomycin, trovafloxacin, trovirdine, Tryptophan, Tuberculin, Tubocurarine Chloride, Tubulozole Hydrochloride, tucarcsol, tulobuterol, turosteride, Tybamate, tylogenin, Tyropanoate Sodium, Tyrosine, Tyrothricin, tyrphostins, ubenimex, Uldazepam, Undecylenic Acid, Uracil Mustard, urapidil, Urea, Uredepa, uridine triphosphate, Urofollitropin, Urokinase, Ursodiol, valaciclovir, Valine, Valnoctamide, Valproate Sodium, Valproic Acid, valsartan, vamicamide, vanadeine, Vancomycin, vaninolol, Vapiprost Hydrochloride, Vapreotide, variolin B, Vasopressin, Vecuronium Bromide, velaresol, Velnacrine Maleate, venlafaxine, Veradoline Hydrochloride, veramine, Verapamil Hydrochloride, verdins, Verilopam Hydrochloride, Verlukast, Verofylline, veroxan, verteporfin, Vesnarinone, vexibinol, Vidarabine, vigabatrin, Viloxazine Hydrochloride, Vinblastine Sulfate, vinburnine citrate, Vincofos, vinconate, Vincristine Sulfate, Vindesine, Vindesine Sulfate, Vinepidine Sulfate, Vinglycinate Sulfate, Vinleurosine Sulfate, vinorelbine, vinpocetine, vintoperol, vinxaltine, Vinzolidine Sulfate, Viprostol, Virginiamycin, Viridofulvin, Viroxime, vitaxin, Volazocine, voriconazole, vorozole, voxergolide, Warfarin Sodium, Xamoterol, Xanomeline, Xanoxate Sodium, Xanthinol Niacinate, xemilofiban, Xenalipin, Xenbucin, Xilobam, ximoprofen, Xipamide, Xorphanol Mesylate, Xylamidine Tosylate, Xylazine Hydrochloride, Xylometazoline Hydrochloride, Xylose, yangambin, zabicipril, zacopride, zafirlukast, Zalcitabine, zaleplon, zalospirone, Zaltidine Hydrochloride, zaltoprofen, zanamivir, zankiren, zanoterone, Zantac, Zarirlukast, zatebradine, zatosetron, Zatosetron Maleate, zenarestat, Zenazocine Mesylate, Zeniplatin, Zeranol, Zidometacin, Zidovudine, zifrosilone, Zilantel, zilascorb, zileuton, Zimeldine Hydrochloride, Zinc Undecylenate, Zindotrine, Zinoconazole Hydrochloride, Zinostatin, Zinterol Hydrochloride, Zinviroxime, ziprasidone, Zobolt, Zofenopril Calcium, Zofenoprilat, Zolamine Hydrochloride, Zolazepam Hydrochloride, zoledronie acid, Zolertine Hydrochloride, zolmitriptan, zolpidem, Zomepirac Sodium, Zometapine, Zoniclezole Hydrochloride, Zonisamide, zopiclone, Zopolrestat, Zorbamyciin, Zorubicin Hydrochloride, zotepine, Zucapsaicin.

Further examples of low dose, antidiabetic active ingredients comprises of but not limited to JTT-501 (PNU-182716) (Reglitazar), AR-H039242, MCC-555 (Netoglitazone), AR-H049020 Tesaglitazar), CS-011 (CI-1037), GW-409544x, KRP-297, RG-12525, BM-15.2054, CLX-0940, CLX-0921, DRF-2189, GW-1929, GW-9820, LR-90, LY-510929, NIP-221, NIP-223, JTP-20993, LY 29311 Na, FK 614, BMS 298585, R 483, TAK 559, DRF 2725 (Ragaglitazar), L-686398, L-168049, L-805645, L-054852, Demethyl asteriquinone B1 (L-783281), L-363586, KRP-297, P32/98, CRE-16336 and EML-16257.

As indicated above the inner portion of the present invention may comprise auxiliary excipients such as for example diluents, binders, lubricants, surfactants, disintegrants, plasticisers, anti-tack agents, opacifying agents, pigments, and such like. As will be appreciated by those skilled in the art, the exact choice of excipient and their relative amounts will depend to some extent on the final oral dosage form.

Suitable diluents include for example pharmaceutically acceptable inert fillers such as microcrystalline cellulose, lactose, starch, dibasic calcium phosphate, saccharides, and/or mixtures of the foregoing. Examples of diluents include microcrystalline celluloses such as those sold under the Trade Mark Avicel PH 101, Avicel PH 102, Avicel PH 112, Avicel PH 200, Avicel PH301 and Avicel PH 302; lactose such as lactose monohydrate, lactose anhydrous and Pharmatose DCL21 (Pharmatose is a Trade Mark), including anhydrous, monohydrate and spray dried forms; dibasic calcium phosphate such as Emcompress (Emcompress is a Trade Mark); mannitol; Pearlitol SD 200 (Pearlitol SD 200 is a trade mark); starch; sorbitol; sucrose; and glucose.

Suitable binders include for example starch, povidone, hydroxypropylmethylcellulose, pregelatinised starch, hydroxypropylcellulose and/or mixtures of the foregoing. Suitable lubricants, including agents that act on the flowability of the powder to be compressed are, for example, colloidal slilcon dioxide such as Aerosil 200 (Aerosil is a Trade Mark); talc; stearic acid, magnesium stearate, calcium stearate and sodium stearyl fumarate.

Suitable disintegrants include for example lightly crosslinked polyvinyl pyrrolidone, corn starch, potato starch, maize starch and modified starches, croscarmellose sodium, cross-povidone, sodium starch glycolate and combinations and mixtures thereof.

The amount of release controlling agent(s) to be used in will be determined based on drug release rate etc.

The release controlling agents(s) are selected from alkyl celluloses, hydroxyalkyl celluloses, cellulose ethers, cellulose esters, nitro celluloses, polymers of acrylic and methacrylic acids and esters thereof, polyamides, polycarbonates, polyalkylenes, polyalkylene glycols, polyalkylene terephthalates, polyvinyl esters, polyvinylpyrrolidone, polyglycolides, polysiloxanes and polyurethanes and co-polymers thereof.

The high water soluble/permeable release controlling agents is suitably polyvinyl alcohol, polyvinylpyrrolidone, methylcellulose, hydroxypropylcellulose, hydroxypropylmethyl cellulose or polyethylene glycol, alginates, polyacrylic acids, xanthun gum or a mixture thereof.

The low water soluble/permeable release controlling agents is suitably ethylcellulose, cellulose acetate, cellulose propionate (lower, medium or higher molecular weight), cellulose acetate propionate, cellulose acetate butyrate, cellulose acetate phthalate, cellulose triacetate, poly(methyl methacrylate), poly(ethyl methacrylate), poly(butyl methacrylate), poly(isobutyl methacrylate), and poly (hexyl methacrylate). Poly(isodecyl methacrylate), poly (lauryl methacrylate), poly (phenyl methacrylate), poly (methyl acrylate), poly (isopropyl acrylate), poly (isobutyl actylate), poly (octadecyl acrylate), waxes such as beeswax, carnauba wax, microcrystalline wax, and ozokerite; fatty alcohols such as cetostearyl alcohol, stearyl alcohol; cetyl alcohol and myristyl alcohol; and fatty acid esters such as glyceryl monostearate, glyceryl distearate, glycerol monooleate, acetylated monoglycerides, tristearin, tripalmitin, cetyl esters wax, glyceryl palmitostearate, glyceryl behenate, and hydrogenated castor oil or a mixture thereof.

The non-biodegradable materials are selected from but are not limited to Ammonio methacrylate copolymers type A and B as described in USP, Polyacrylate dispersion 30% as described in Ph. Eur., Polyvinyl acetate dispersion, cellulose derivatives such as ethylcellulose, cellulose acetate waxes such as beeswax, carnauba wax, microcrystalline wax, and ozokerite; fatty alcohols such as cetostearyl alcohol, stearyl alcohol; cetyl alcohol and myristyl alcohol; and fatty acid esters such as glyceryl monostearate, glyceryl distearate, glycerol monooleate, acetylated monoglycerides, tristearin, tripalmitin, cetyl esters wax, glyceryl palmitostearate, glyceryl behenate, and hydrogenated castor oil.

The mucoadhesive release controlling agents are selected from but are not limited to carbopol, sodium carboxymethyl cellulose, hydroxypropyl cellulose, hydroxypropylmethyl cellulose, hydroxyethyl cellulose, methyl cellulose, sodium hyaluronate, gaur gum, sodium alginate, polycabophil, starch, dextran or chitosan.

The ammonio methacrylate co-polymers are preferably selected from the group consisting of poly(ethyl acrylate, methyl methacrylate, trimethylammonioethyl methacrylate chloride) 1:2:0.1; poly(ethyl acrylate, methyl methacrylate, trimethylamonioethyl methacrylate chloride) 1:2:0.2 and poly(ethyl acrylate, methyl methacrylate) 1:1.

Active ingredients especially the poorly soluble active ingredients mentioned above can be micronized to increase solubility and/or bioavialabiity.

(ii) Outer Portion: The outer portion comprises of a) Micro matrix particles containing high dose, high solubility active ingredient and one or more hydrophobic release controlling agent, b) Coating of Micro matrix particles with one or more hydrophobic release controlling agents. The outer portion may also include one or more commonly used excipients in oral pharmaceutical formulations. The release of the high dose, high solubility active ingredient is controlled through dual retard technique. The dual retard technique is a combination of matrix formulations and reservoir formulations. First the micro matrix particles of high dose, high solubility dose active ingredient and one or more hydrophobic release controlling agents are formed and then these are further coated with one or more release controlling agents. Thus the dual retard release technique presents the double barriers and effectively controls the diffusion of the high dose, high solubility active ingredients from the present invention in predictable manner and also significantly reduces the amount of release controlling agents which are otherwise required in very high quantity and make the dosage form very bulky and therefore pose difficulty in swallowing. The other advantages of the present invention are such as it reduces the chances of dose dumping, unnecessary burst effects and failure of the system, which are otherwise usually associated with simple matrix or reservoir systems.

Further advantages of present invention include the disintegration of inner portion is not hindered as nonswellable release controlling agents are used which do not swell and maintain the shape during operation and it effectively prevents the separation of the layers of the multilayered tablets which is normally associated with normal multilayered tablets.

The high dose, high solubility active ingredient can be present in the form of a free base or in the form of pharmaceutically acceptable salts. Pharmaceutically acceptable salts forming part of this invention are intended to define but not limited to salts of the carboxylic acid moiety such as alkali metal salts like Li, Na and K salts; alkaline earth metal salts like Ca and Mg salts; salts of organic bases such as lysine, arginine, guanidine, diethanolamine, choline, and the like; ammonium or substituted ammonium salts and aluminium salts. Salts may be acid addition salts which defines but not limited to sulfates, nitrates, phosphates, perchlorates, borates, hydrohalides, acetates, tartrates, maleates, citrates, succinates, palmoates, methanesulfonates, benzoates, salicylates, hydroxynaphthoates, benzensulfonates, ascorbates, glycerophosphates, ketoglutarates and the like. Further, the high dose, high solubility active ingredient, where applicable, may be present either in the form of one substantially optically pure enantiomer or as a mixture of enantiomers or polymorphs thereof.

The high dose, high solubility active ingredient is in the form of modified release and has dose from 500 mg to 1500 mg. The high dose, high solubility active ingredient comprises of the following therapeutic classes but not limited to adrenergic agent; adrenocortical steroid; adrenocortical suppressant; aldosterone antagonist; amino acid; anabolic; analeptic; analgesic; anesthetic; anorectic; anti-acne agent; anti-adrenergic; anti-allergic; anti-amebic; anti-anemic; anti-anginal; anti-arthritic; anti-asthmatic; anti-atherosclerotic; antibacterial; anticholinergic; anticoagulant; anticonvulsant; antidepressant; antidiabetic; antidiarrheal; antidiuretic; antiemetic; anti-epileptic; antifibrinolytic; antifungal; antihemorrhagic; antihistamine; antihyperlipidemia; antihypertensive; antihypotensive; anti-infective; anti-inflammatory; antimicrobial; antimigraine; antimitotic; antimycotic, antinauseant, antineoplastic, antineutropenic, antiparasitic; antiproliferative; antipsychotic; antirheumatic; antiseborrheic; antisecretory; antispasmodic; antithrombotic; anti-ulcerative; antiviral; appetite suppressant; blood glucose regulator; bone resorption inhibitor; bronchodilator; cardiovascular agent; cholinergic; depressant; diagnostic aid; diuretic; dopaminergic agent; estrogen receptor agonist; fibrinolytic; fluorescent agent; free oxygen radical scavenger; gastric acid supressant; gastrointestinal motility effector; glucocorticoid; hair growth stimulant; hemostatic; histamine H2 receptor antagonists; hormone; hypocholesterolemic; hypoglycemic; hypolipidemic; hypotensive; imaging agent; immunizing agent; immunomodulator; immunoregulator; immunostimulant; immunosuppressant; keratolytic; LHRH agonist; mood regulator; mucolytic; mydriatic; nasal decongestant; neuromuscular blocking agent; neuroprotective; NMDA antagonist; non-hormonal sterol derivative; plasminogen activator; platelet activating factor antagonist; platelet aggregation inhibitor; psychotropic; radioactive agent; scabicide; sclerosing agent; sedative; sedative-hypnotic; selective adenosine A1 antagonist; serotonin antagonist; serotonin inhibitor; serotonin receptor antagonist; steroid; thyroid hormone; thyroid inhibitor; thyromimetic; tranquilizer; amyotrophic lateral sclerosis agent; cerebral ischemia agent; Paget's disease agent; unstable angina agent; vasoconstrictor; vasodilator; wound healing agent; xanthine oxidase inhibitor.

Examples of high dose, high solubility active ingredients comprise of but not limited to potassium chloride, metformin hydrochloride, phenformin, buformin, clindamycin, hydroxyurea, eprosartan; erythromycin, lactobionate, vancomycin hydrochloride, balsalazide disodium, sodium valproate, niacin, aminocaproic acid, acetaminophen, Ciprofloxacin, quetiapine. Other drugs suitable for use and meeting the solubility and dose criteria described above will be apparent to those skilled in the art.

In the dosage form of the present invention, the outer portion may optionally contain more than one high dose high solubility active ingredient.

In the dosage form of the present invention, the outer portion may optionally contain more than one high dose high solubility antidiabetic active ingredient.

As indicated above the outer portion of the present invention may comprise auxiliary excipients such as for example lubricants, plasticisers, anti-tack agents, opacifying agents, pigments, and such like. As will be appreciated by those skilled in the art, the exact choice of excipient and their relative amounts will depend to some extent on the final oral dosage form.

Suitable lubricants, including agents that act on the flowability of the powder to be compressed are, for example, colloidal silicon dioxide such as Aerosil 200 (Aerosil is a Trade Mark); talc; stearic acid, magnesium stearate, calcium stearate and sodium stearyl fumarate.

In micro matrix particles, the active ingredient and one or more hydrophobic release controlling agents are preferably present in a ratio of from 100:1 to 100:75, more particularly from 100:2.5 to 100:50, still more preferably from 100:2.5 to 100:30 and most preferably from 100:2.5 to 100:20.

In outer portion, micro matrix particles and coating of one or more hydrophobic release controlling agents are preferably present in a ratio of from 100:0.5 to 100:75, more particularly from 100:2.5 to 100:50, still more preferably from 100:2.5 to 100:30 and most preferably from 100:2.5 to 100:20.

According to one embodiment the release controlling agents are pharmaceutically excipients, which are hydrophobic in nature.

The polymers that can be used to form the rate-controlling membrane or micromatrix are described in greater detail herein below.

The hydrophobic release controlling agents are selected from but are not limited to Ammonio methacrylate copolymers type A and B as described in USP, methacrylic acid copolymer type A, B and C as described in USP, Polyacrylate dispersion 30% as described in Ph. Eur., Polyvinyl acetate dispersion, ethylcellulose, cellulose acetate, cellulose propionate (lower, medium or higher molecular weight), cellulose acetate propionate, cellulose acetate butyrate, cellulose acetate phthalate, cellulose triacetate, poly(methyl methacrylate), poly(ethyl methacrylate), poly(butyl methacrylate), poly(isobutyl methacrylate), and poly (hexyl methacrylate). Poly(isodecyl methacrylate), poly (lauryl methacrylate), poly (phenyl methacrylate), poly (methyl acrylate), poly (isopropyl acrylate), poly (isobutyl actylate), poly (octadecyl acrylate), waxes such as beeswax, carnauba wax, microcrystalline wax, and ozokerite; fatty alcohols such as cetostearyl alcohol, stearyl alcohol; cetyl alcohol and myristyl alcohol; and fatty acid esters such as glyceryl monostearate, glycerol distearate; glycerol monooleate, acetylated monoglycerides, tristearin, tripalmitin, cetyl esters wax, glyceryl palmitostearate, glyceryl behenate, and hydrogenated castor oil.

According to an especially preferred embodiment the release controlling agents contains ammonio methacrylate co-polymers and fatty acid esters as hereinafter described. The suitable hydrophobic agents are polymers sold under the Trade Mark Eudragit RS (Ammonio Methacrylate Copolymer type B USP), (Eudragit NE 30D (Polyacrylate dispersion 30% Ph. Eur.), Eudragit RL (Ammonio Methacrylate Copolymer type A USP) and Kollicoat SR 30 D and fatty acid esters such as glyceryl behenate, glycerol distearate and hydrogenated castor oil. Eudragit polymers are polymeric lacquer substances based on acrylate and/or methacrylates.

The outer portion can also include one or more commonly used excipients in oral pharmaceutical formulations.

Representative commonly used excipients in oral pharmaceutical formulations include talc, fumed silica, glyceryl monostearate, magnesium stearate, calcium stearate, kaolin, colloidal silica, gypsum, Tween 80, Geleol pastiles (trade mark), micronised silica and magnesium trisilicate. The quantity of commonly used excipients in oral pharmaceutical formulations used is from about 0.5% to about 200% by weight, preferably from 2 to 100% more particularly 10 to 60% based on the total dry weight of the polymer.

The outer portion can also include a material that improves the processing of the release controlling agents. Such materials are generally referred to as "plasticisers" and include, for example, adipates, azelates, benzoates, citrates, isoebucaes, phthalates, sebacates, stearates, tartrates, polyhydric alcohols and glycols.

Representative plasticisers include acetylated monoglycerides; butyl phthalyl butyl gylcolate; dibutyl tartrate; diethyl phthalate; dimethyl phthalate,; ethyl phthalyl ethyl glycolate; glycerin; ethylene glycol, propylene glycol; Triethyl citrate; triacetin; tripropinoin; diacetin; dibutyl phthalate; acetyl monoglyceride; polyethylene glycols; castor oil; triethyl citrate; polyhydric alcohols, acetate esters, glycerol triacetate, acetyl triethyl citrate, dibenzyl phthalate, dihexyl phthalate, butyl octyl phthalate, diisononyl phthalate, butyl octyl phthalate, dioctyl azelate, epoxidised tallate, triisoctyl trimellitate, diethylexyl phthalate, di-n-octyl phthalate, di-I-octyl phthalate, di-I-decyl phthalate, di-n-undecyl phthalate, di-n-tridecyl phthalate, tri-2-ethylexyl trimellitate, di-2-ethylexyl adipate, di-2-ethylhexyl sebacate, di-2-ethylhexyl azelate, dibutyl sebacate, glyceryl monocaprylate, glycerol distearate and glyceryl monocaprate. The amount of plasticiser to be used is from about 1% to 50% based on the weight of the dry release controlling agent(s). The amount of release controlling agent(s) to be used in forming the outer portion will be determined based on various parameters such as the desired delivery properties, including the amount of active ingredient to be delivered, the active ingredient release rate desired, and the size of the micro matrix particles.

The novel dosage form of the present invention can be manufactured by the following procedure:

Inner Portion

The granules of the inner portion can be manufactured in accordance with usual techniques in which the active ingredient and other excipients are mixed and granulated by adding solution of binder in a low or high shear mixer or by fluidized bed granulation. The granulate is dried, preferably in a fluidized bed dryer. The dried granulate is sieved and mixed with lubricants and disintegrants. Alternatively the manufacture of granules of inner portion can be made by direct mixing of the directly compressible excipients or by roller compaction.

B) Outer Portion

The micro matrix particles of the outer portion can be manufactured in accordance with usual techniques in which the active ingredient and one or more hydrophobic release controlling agents are mixed and granulated by adding solvent in a low or high shear mixer or by fluidized bed granulator. The granulate is dried, preferably in a fluidized bed dryer. The dried granulate is sized. The sizing of the micromatrix particles can be done using oscillating granulator, comminuting mill or any other conventional method. The sieve used for the sizing can have openings from 0.25 mm to 5 mm. Alternatively the micro matrix particles can be made by extrusion, spheronization or by roller compaction. The micro matrix particles can be coated by a solution of one or more hydrophobic release controlling agents by any known method, including spray application. Spraying can be carried out using a fluidized bed coated (preferably Wurster coating), or in a pan coating system. Alternatively the coating of the micro matrix particles with one or more rate controlling agents can be done by hot melt process using a granulator or fluidized bed coated (preferably Wurster coating), or in a pan coating system.

Tablet Compression

The compression of tablets is carried out on usual press coaters (e.g. machines of the Manesty, Cadmach or Kilian) with slight modification. The device such as feed frame and hoppers making top layer are eliminated. The granules of the inner layer are charged in the hopper of the machine compressing first layer and the granules of the outer layer are charged in the hopper of the machine compressing the coating. On operation only the bottom layer of the coating (outer portion) is deposited into the die and the first layer is placed on it. The compression wheels then embed the first layer in the granules of the outer layer, displacing some of latter to form sides, and finally press the whole into the tablet. The resultant tablet has inner portion covered by the outer portion from all the sides except top surface that remains uncovered and the level of the inner portion and the outer portion is same. The tablets can be made of various sizes and shapes. The present invention uses round punch tooling with upper flat bottom punches and lower flat bottom beveled edges lower punches for the compression of inner portion and oblong shaped flat bottom beveled edges punches for the compression of the outer portion.

BRIEF DESCRIPTION OF THE DRAWINGS

FIG. 4 (a) is a cross section of coated micro matrix particles prepared by spheronization and coating for the purpose of illustration only.

FIG. 4 (b) is a cross section of coated micro matrix particles prepared by granulation and coating for the purpose of illustration only.

Referring to FIGS. 1 to 3, a dosage form 4 as described in the present invention having an inner portion 1 containing low dose active ingredient as immediate release and outer portion 2 containing high dose, high solubility active ingredient as modified release. FIG. 5 shows the release profile of a low dose active ingredient as immediate release 9 and the release profile of a high solubility active ingredient as modified release 10. FIGS. 6 and 7 shows release of high dose, high solubility active agent 11 & 12 and 15 & 16 as per example 1 & 2 respectively from a dosage form prepared using dual retard technique as described in the present invention and release of high dose, high solubility active agent 13 & 14 and 17 & 18 as per example 3 & 4 respectively from a dosage form prepared without using dual retard release technique. The total quantity of the hydrophobic release controlling agent is same in all the dosage forms inspite of that the figures clearly shows that dual retard technology significantly reduces the burst effect and effectively controls the release rate of the high dose, high solubility active ingredient for prolonged period.

DESCRIPTION OF THE PREFERRED EMBODIMENTS

Figure 1:
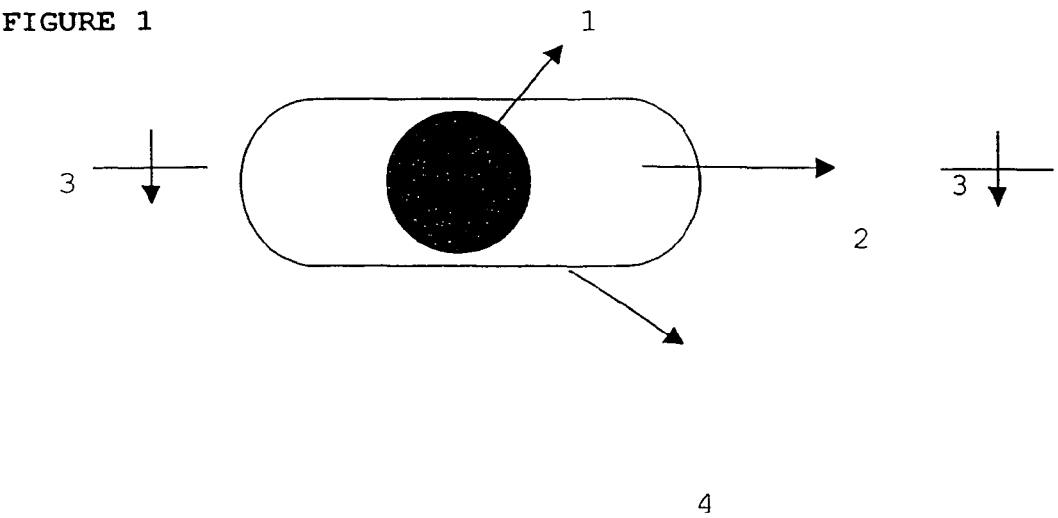
FIG. 1 is a plan view of the dosage form described in the present invention.
Figure 2:
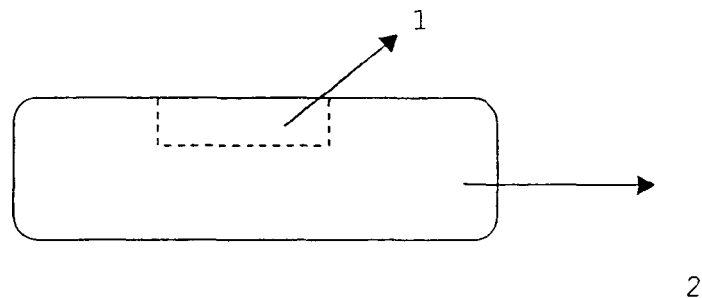
FIG. 2 is an edge view of the dosage form described in the present invention.
Figure 3:
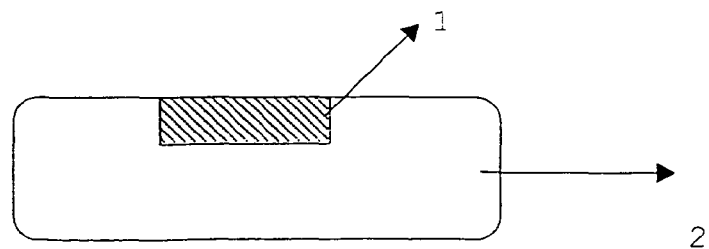
FIG. 3 is a transverse section view as seen along the line 3-3 of FIG. 1.
Figure 4A:
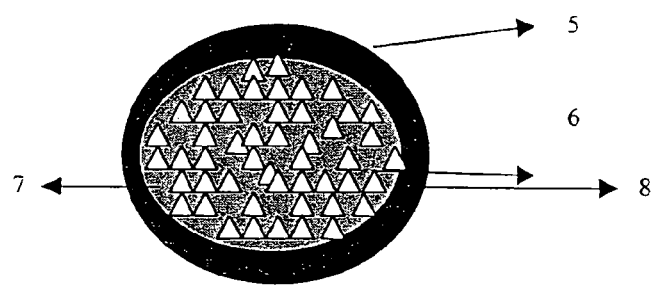
FIG. 4(a) & 4(b) shows the cross section of the coated micro matrix particles 5 and having 6 a high dose, high solubility active ingredient, 7 hydrophobic release controlling agent and 8 a coating of hydrophobic release controlling agent.
Figure 4B:
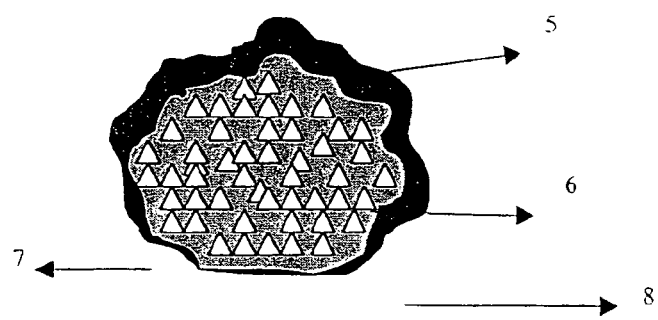
Figure 5:
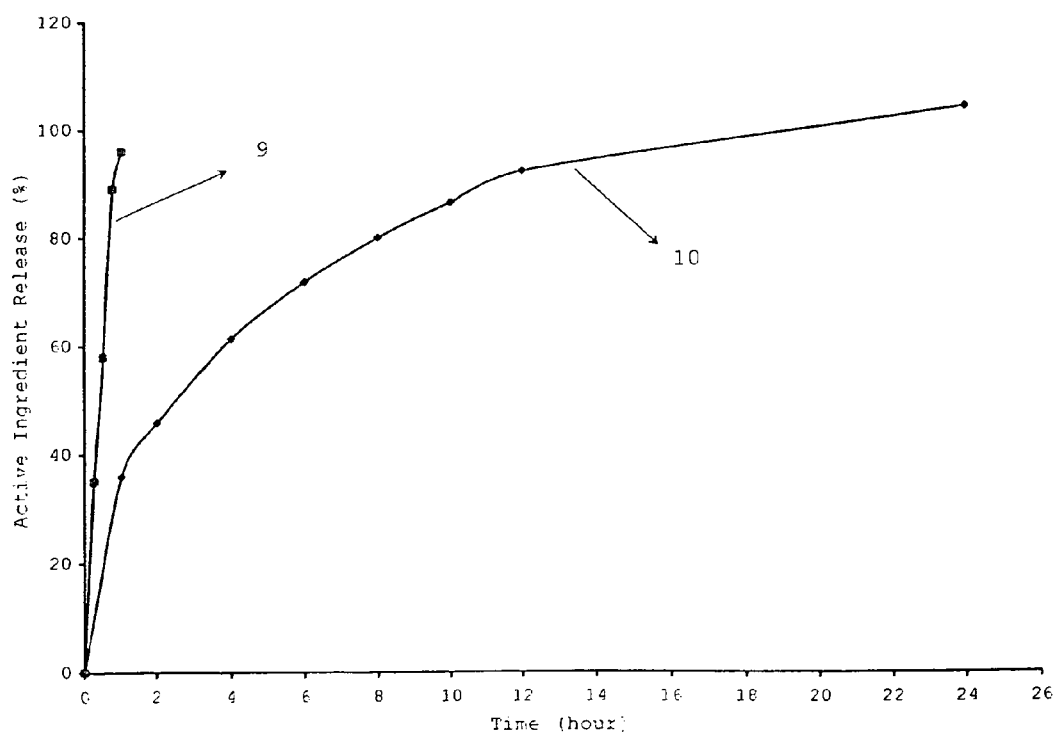
FIG. 5 is a plot of % active ingredient versus time for immediate release and modified release active agent.
Figure 6:
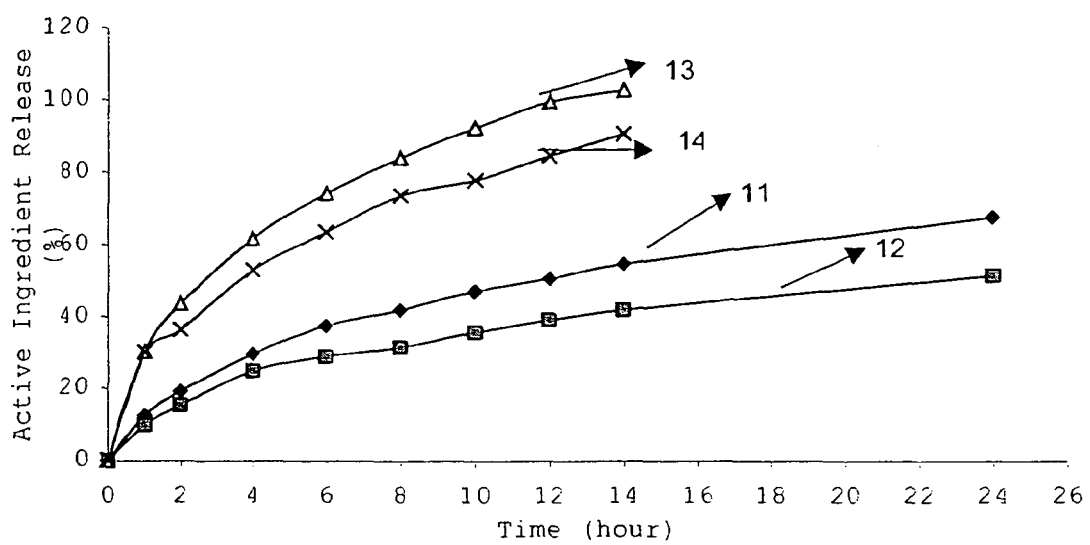
FIG. 6 is a plot of % active ingredient versus time for modified release active agent prepared using dual retard technique as described in the present invention and prepared without retard release technique as per examples 1 and 3.
Figure 7:
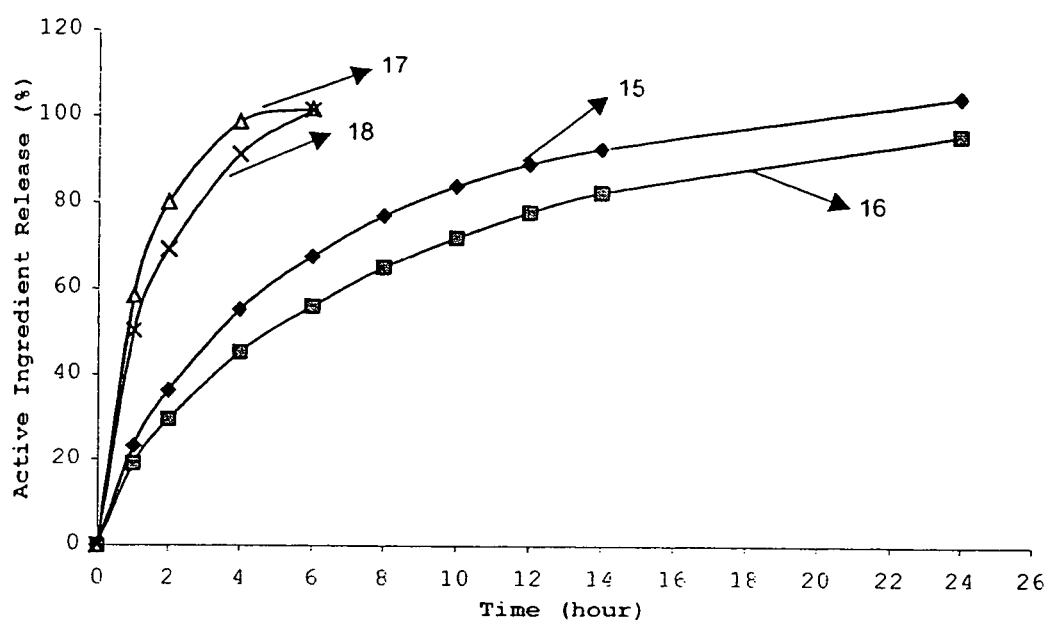
FIG. 7 is a plot of % active ingredient versus time for modified release active agent prepared using dual retard technique as described in the present invention and prepared without retard release technique as per examples 2 and 4.

The following examples further illustrate but by no means limit the present invention.

The dissolution of novel dosage form of the present invention was determined by following method.

| For sodium valproate- | |
|---|---|
| Instrument | Apparatus I, USP (basket) |
| Revolution | 60/min. |
| Temperature | 37 ± 0.5° C. |
| Dissolution medium | 1000 ml pH 6.8 buffer |
| For niacin- | |
| Instrument | Apparatus I, USP (Basket) |
| Revolution | 100/min. |
| Temperature | 37 ± 0.5° C. |
| Dissolution medium | 900 ml 0.1 N HCl |
| For lamotrigine- | |
| Instrument | Apparatus II, USP (Paddle) |
| Revolution | 100/min. |
| Temperature | 37 ± 0.5° C. |
| Dissolution medium | 1000 ml 0.001 N HCl |
| For pravastatin sodium- | |
| Instrument | Apparatus II, USP (Paddle) |
| Revolution | 100/min. |
| Temperature | 37 ± 0.5° C. |
| Dissolution medium | 900 ml pH 6.8 buffer |
| For metformin hydrochloride- | |
| Instrument | Apparatus II, USP (Paddle) |
| Revolution | 50/min. |
| Temperature | 37 ± 0.5° C. |
| Dissolution medium | 900 ml 0.1 N HCl |
| For rosiglitazone maleate- | |
| Instrument | Apparatus II, USP (Paddle) |
| Revolution | 100/min. |
| Temperature | 37 ± 0.5° C. |
| Dissolution medium | 500 ml 0.01 N HCl |
| For glimepiride- | |
| Instrument | Apparatus II, USP (Paddle) |
| Revolution | 75/min. |
| Temperature | 37 ± 0.5° C. |
| Dissolution medium | 500 ml 0.5% sodium lauryl sulfate in water |

The composition of outer portion in the dosage form comprising high dose high solubility antidiabetic active ingredient is as follows—

| Micro matrix particles- | |
|---|---|
| Metformin hydrochloride | 75% w/w to 99% w/w |
| Eudragit RS | 1% w/w to 25% w/w |
| Coated micro matrix particles | |
| Micro matrix particles | 70% w/w to 99% w/w |
| Hydrogenated castor oil | 1% w/w to 30% w/w |
| Magnesium stearate | 0% w/w to 2% w/w |

The dissolution of high dose high solubility ingredient of the formulation of the present invention is achieved not more than 45% in 1 hour and from 25 to 90% in six hours.

The dissolution of metformin hydrochloride is achieved not more than 50% in 1 hour, and from 30 to 90% is in four hours and not less than 65% in 12 hours.

After oral administration of a dosage form of the present invention the maximum plasma concentration can be achieved between 700 ng/ml and 2500 ng/ml, preferably from 900 ng/ml to 2400 ng/ml and more preferably from 1000 ng/ml to 2350 ng/ml. The in vivo mean dissolution time (MDT) of the dosage form of the present invention is 4 to 6 hours. The minimum plasma concentration (at 24 hours) of the said dosage form ranges between 0 to 450 ng/ml after oral administration.

EXAMPLES

Example 1

Production of Inner Portion 11.71% w/w of pravastatin sodium is mixed with 52.62% w/w of lactose monohydrate and 22.22% w/w starch and the mixture is granulated in a binder of 2.22 v povidone in water and then dried. The granules are sieved and mixed with 1.11% w/w magnesium stearate, 9.0 g sodium starch glycolate, 0.11% w/w lake of sunset yellow. This mixture is compressed to 90 mg weight tablets having a diameter of 6.35 mm.

2) Production of Outer Portion

A) Micro matrix particles-90.91% w/w of niacin is mixed with 9.09% w/w of Eudragit RSPO (Ammonio Methacrylate Copolymer type B USP) and the mixture is granulated with a solvent mixture of acetone and methylene chloride and then dried. The granules are sized.

B) Coating of Micro matrix particles—85.84% w/w of micro matrix particles is charged in fluidized bed processor. 13.61% w/w of hydrogenated castor oil is dissolved in acetone and this coating solution is sprayed to coat the micro matrix particles. The coated micro matrix particles are sieved and mixed with 0.86% w/w magnesium stearate.

3) Compression of Tablets

Tablet (A)—90 mg granules of inner portion are pressed to tablets (equal to 10 mg pravastatin) using 6.35 mm round punches and 643 mg granules of outer portion (equal to 500 mg niacin) are compressed using 14.95×8.35 mm oblong punches.

Tablet (B)—90 mg granules of inner portion are pressed to tablets (equal to 10 mg pravastatin) using 6.35 mm round punches and 1286 mg granules of outer portion (equal to 1000 mg niacin) are compressed using 20.3×9.8 mm oblong punches. The compression is done on press coater machine in such a manner that the resultant tablet has inner portion covered by the outer portion from all the sides except top surface that remains uncovered and the level of the inner portion and the outer portion is on the same surface.

The dissolution rate of the novel dosage form was determined (Table 1 and 2)

TABLE 1

Dissolution profile of tablet (A)

| Niacin | | Pravastatin sodium | |
|---|---|---|---|
| Time (hour) | % Released | Time (min) | % Released |
| 1 | 12.4 | 45 | 83.8 |
| 2 | 19.1 | 60 | 84.1 |
| 4 | 29.4 | | |
| 6 | 37.4 | | |
| 8 | 41.9 | | |
| 10 | 47.1 | | |
| 12 | 50.6 | | |
| 14 | 54.6 | | |
| 24 | 67.7 | | |

TABLE 2

Dissolution profile of tablet (B)

| Niacin | | Pravastatin sodium | |
|---|---|---|---|
| Time (hour) | % Released | Time (min) | % Released |
| 1 | 9.8 | 45 | 84.1 |
| 2 | 15.3 | 60 | 85.6 |
| 4 | 24.7 | | |
| 6 | 28.7 | | |
| 8 | 31.4 | | |
| 10 | 35.7 | | |
| 12 | 39.1 | | |
| 14 | 41.9 | | |
| 24 | 51.5 | | |

Example 2

1) Production of Inner Portion 38.47% w/w of lamotrigine is mixed with 2.71% w/w of crosspovidone and 0.18% w/w colloidal silicon dioxide and the mixture is granulated in a binder of 0.71% w/w povidone in water and then dried. The granules are sieved and mixed with 28.70% w/w of Mannitol (Pearlitol SD 200 R.T.M.), 12.31% w/w of crosspovidone, 2.31% w/w of magnesium stearate, 6.15% w/w aspartame, 2.31% w/w talc, 5.0% w/w flavour and 1.15% w/w of colloidal silicon dioxide. This mixture is compressed to 65 mg weight tablets having a diameter of 5.55 mm.

2) Production of Outer Portion

A) Micro matrix particles-90.91% w/w of sodium valproate is mixed with 9.09% w/w of Eudragit RSPO (Ammonio Methacrylate Copolymer type B USP) and the mixture is granulated with a solvent mixture of acetone and methylene chloride and then dried. The granules are sized.

B) Coating of Micro matrix particles—85.84% w/w of micro matrix particles is charged in fluidized bed processor. 13.61% w/w of hydrogenated castor oil is dissolved in acetone and this coating solution is sprayed to coat the micro matrix particles. The coated micro matrix particles are sieved and mixed with 0.86% w/w magnesium stearate.

Compression of Tablets

Tablet (A)—65 mg granules of inner portion are pressed to tablets (equal to 25 mg lamotrigine) using 5.55 mm round punches and 643 mg granules of outer portion (equal to 500 mg sodium valproate) are compressed using 14.95×8.35 mm oblong punches.

Tablet (B)—65 mg granules of inner portion are pressed to tablets (equal to 25 mg lamotrigine) using 5.55 mm round punches and 1286 mg granules of outer portion (equal to 1000 mg sodium valproate) are compressed using 20.3×9.8 mm oblong punches. The compression procedure is same as Example 1. The dissolution rate of the novel dosage form was determined (Table 3 and 4)

TABLE 3

Dissolution profile of tablet (A)

| Sodium valproate | | Lamotrigine | |
|---|---|---|---|
| Time (hour) | % Released | Time (min) | % Released |
| 1 | 23.3 | 15 | 83.5 |
| 2 | 36.3 | 30 | 88.6 |
| 4 | 55.1 | 45 | 91.6 |
| 6 | 67.5 | 60 | 92.8 |
| 8 | 77.0 | | |
| 10 | 83.8 | | |
| 12 | 88.9 | | |
| 14 | 92.5 | | |
| 24 | 104.6 | | |

TABLE 4

Dissolution profile of tablet (B)

| Sodium valproate | | Lamotrigine | |
|---|---|---|---|
| Time (hour) | % Released | Time (min) | % Released |
| 1 | 19.0 | 15 | 90.3 |
| 2 | 29.5 | 30 | 95.6 |
| 4 | 45.2 | 45 | 98.3 |
| 6 | 55.9 | | |
| 8 | 65.0 | | |
| 10 | 71.9 | | |
| 12 | 77.8 | | |
| 14 | 82.4 | | |
| 24 | 95.8 | | |

Dosage forms described in the examples 3 and 4 are prepared by not coating the micro matrix particles of the outer portion but the hydrophobic release controlling agent is mixed with the micro matrix particles. The sole purpose of these examples is to demonstrate the usefulness of the present invention as described earlier. The examples clearly show that the rate of release of the modified release active ingredient is significantly faster than the present invention.

Example 3

Production of Inner Portion

Same as for Example 1

Production of Outer Portion 77.76% w/w of niacin is mixed with 7.78% w/w of Eudragit RSPO (Ammonio Methacrylate Copolymer type B USP) and the mixture is granulated with a solvent mixture of acetone and methylene chloride and then dried. The granules are sized and mixed with 13.61% w/w of hydrogenated castor oil and 0.86% w/w of magnesium stearate.

Compression of Tablets

Tablet (A)—Same as for Example 1

Tablet (B)—Same as for Example 1

The dissolution rate of the novel dosage form was determined (Table 5 and 6)

TABLE 5

Dissolution profile of tablet (A)

| Niacin | | Pravastatin sodium | |
|---|---|---|---|
| Time (hour) | % Released | Time (min) | % Released |
| 1 | 30.1 | 45 | 75.9 |
| 2 | 43.6 | 60 | 80.9 |
| 4 | 61.6 | | |
| 6 | 74.1 | | |
| 8 | 83.9 | | |
| 10 | 92.1 | | |
| 12 | 99.4 | | |
| 24 | 102.6 | | |

TABLE 6

Dissolution profile of tablet (B)

| Niacin | | Pravastatin sodium | |
|---|---|---|---|
| Time (hour) | % Released | Time (min) | % Released |
| 1 | 29.9 | 45 | 89.6 |
| 2 | 36.3 | 60 | 90.0 |
| 4 | 52.8 | | |
| 6 | 63.4 | | |
| 8 | 73.5 | | |
| 10 | 77.8 | | |
| 12 | 84.5 | | |
| 24 | 90.5 | | |

Example 4

1) Production of Inner Portion

Same as for Example 2

2) Production of Outer Portion 77.76% w/w of sodium valproate is mixed with 7.78% w/w of Eudragit RSPO (Ammonio Methacrylate Copolymer type B USP) and the mixture is granulated with a solvent mixture of acetone and methylene chloride and then dried. The granules are sized and mixed with 13.61% w/w of hydrogenated castor oil and 0.86% w/w of magnesium stearate.

3) Compression of Tablets

Tablet (A)—Same as for Example 2

Tablet (B)—Same as for Example 2

The dissolution rate of the novel dosage form was determined (Table 7 and 8)

TABLE 7

Dissolution profile of tablet (A)

| Sodium valproate | | Lamotrigine | |
|---|---|---|---|
| Time (hour) | % Released | Time (min) | % Released |
| 1 | 58.3 | 15 | 81.8 |
| 2 | 79.9 | 30 | 89.8 |
| 4 | 98.5 | 45 | 91.7 |
| 6 | 101.6 | 60 | 97.4 |

TABLE 8

| Dissolution profile of tablet (B) | | | |
|---|---|---|---|
| Sodium valproate | | Lamotrigine | |
| Time (hour) | % Released | Time (min) | % Released |
| 1 | 50.2 | 15 | 86.1 |
| 2 | 69.1 | 30 | 87.3 |
| 4 | 91.0 | 45 | 92.6 |
| 6 | 101.3 | 60 | 98.3 |

Example 5

1) Production of Inner Portion 5.89% w/w of rosiglitazone maleate is mixed with 55.89% w/w of lactose monohydrate and 22.22% w/w starch and the mixture is granulated in a binder of 2.78% w/w povidone and 2.78% w/w starch in water and then dried. The granules are sieved and mixed with 0.28% w/w magnesium stearate, 10.00% w/w sodium starch glycolate, 0.17% w/w ferric oxide yellow. This mixture is compressed to 90 mg weight tablets having a diameter of 6.35 mm.

2) Production of Outer Portion

A) Micro matrix particles—90.91% w/w of metformin hydrochloride is mixed with 9.09% w/w of Eudragit RS (Ammonio Methacrylate Copolymer type B USP) and the mixture is granulated with a solvent mixture of acetone and methylene chloride and then dried. The granules are sized.

B) Coating of Micro matrix particles-85.54% w/w of micro matrix particles is charged in fluidized bed processor. 13.61% w/w of hydrogenated castor oil is dissolved in acetone and this coating solution is sprayed to coat the micro matrix particles. The coated micro matrix particles are sieved and mixed with 0.86% w/w magnesium stearate.

3) Compression of Tablets

Tablet (A)-90 mg granules of inner portion are pressed to tablets (equal to 4 mg rosiglitazone) using 6.35 mm round punches and 643 mg granules of outer portion (equal to 500 mg metformin hydrochloride) are compressed using 14.95×8.35 mm oblong punches.

Tablet (B)—90 mg granules of inner portion are pressed to tablets (equal to 4 mg rosiglitazone) using 6.35 mm round punches and 1286 mg granules of outer portion (equal to 1000 mg metformin hydrochloride) are compressed using 20.3×9.8 mm oblong punches.

The compression is done on press coater machine in such a manner that the resultant tablet has inner portion covered by the outer portion from all the sides except top surface that remains uncovered and the level of the inner portion and the outer portion is on the same surface.

The dissolution rate of the novel dosage form was determined (Table 9 and 10)

TABLE 9

| Dissolution profile of tablet (A) | | | |
|---|---|---|---|
| Metformin hydrochloride | | Rosiglitazone | |
| Time (hour) | % Released | Time (min) | % Released |
| 1 | 42.5 | 15 | 84.88 |
| 2 | 58.0 | 30 | 99.02 |
| 4 | 74.09 | 45 | 101.26 |
| 6 | 86.1 | 60 | 104.4 |
| 8 | 97.8 | | |
| 10 | 101.9 | | |
| 12 | 103.7 | | |

TABLE 10

| Dissolution profile of tablet (B) | | | |
|---|---|---|---|
| Metformin hydrochloride | | Rosiglitazone | |
| Time (hour) | % Released | Time (min) | % Released |
| 1 | 38.2 | 45 | 96.79 |
| 2 | 53.4 | 60 | 99.32 |
| 4 | 69.5 | | |
| 6 | 78.1 | | |
| 8 | 86.8 | | |
| 10 | 93.6 | | |
| 12 | 97.65 | | |

Example 6

Production of Inner Portion
Same as for Example 5
Production of Outer Portion

A) Micro matrix particles-86.96% w/w of metformin hydrochloride is mixed with 13.07% w/w of Eudragit RS (Ammonio Methacrylate Copolymer type B USP) and the mixture is granulated with a solvent mixture of acetone and methylene chloride and then dried. The granules are sized.

B) Coating of Micro matrix particles—86.40% w/w of micro matrix particles is charged in fluidized bed processor. 13.15% w/w of hydrogenated castor oil is dissolved in acetone and this coating solution is sprayed to coat the micro matrix particles. The coated micro matrix particles are sieved and mixed with 0.45% w/w magnesium stearate.

Compression of tablets 90 mg granule of inner portion are pressed to tablets (equivalent to 4 mg rosiglitazone) using 6.35 mm round punches and 1331 mg granules of outer portion (equivalent to 1000 mg metformin hydrochloride) are compressed using 20.3×9.8 mm oval punches. The compression procedure is same as Example 5.

The dissolution rate of the novel dosage form was determined (Table 11)

TABLE 11

| Dissolution profile | | | |
|---|---|---|---|
| Metformin Hydrochloride | | Rosiglitazone Maleate | |
| Time (hour) | % Released | Time (min) | % Released |
| 1 | 32.10 | 15 | 75.63 |
| 2 | 41.65 | 30 | 88.35 |
| 4 | 59.05 | 45 | 103.49 |
| 6 | 63.90 | 60 | 105.70 |
| 8 | 73.63 | | |
| 10 | 79.35 | | |
| 12 | 84.21 | | |
| 24 | 94.91 | | |

Example 7

Production of Inner Portion
Same as for Example 5
Production of Outer Portion
Micro Matrix Particles—
Same as for Example 5

B) Coating of Micro matrix particles-89.36% w/w of micro matrix particles is charged in fluidized bed processor.

10.15% w/w of glycerol distearate type 1 Ph. Eur. (Precirol ATO 5 R.T.M.) is dissolved in acetone and this coating solution is sprayed to coat the micro matrix particles. The coated micro matrix particles are sieved and mixed with 0.49% w/w magnesium stearate.

Compression of Tablets 90 mg granule of inner portion are pressed to tablets (equal to 4 mg rosiglitazone maleate) using 6.35 mm round punches and 1231 mg granules of outer portion (equal to 1000 mg metformin hydrochloride) are compressed using 20.3×9.8 mm oval punches. The compression procedure is same as Example 5. The dissolution rate of the novel dosage form was determined (Table 12)

TABLE 12

Dissolution profile

| Metformin Hydrochloride | | Rosiglitazone Maleate | |
| --- | --- | --- | --- |
| Time (hour) | % Released | Time (min) | % Released |
| 1 | 39.9 | 15 | 78.32 |
| 2 | 51.7 | 30 | 89.15 |
| 4 | 69.2 | 45 | 97.13 |
| 6 | 82.5 | 60 | 100.57 |
| 8 | 83.8 | | |
| 10 | 91.2 | | |
| 12 | 94.9 | | |
| 24 | 99.8 | | |

Example 8

Production of Inner Portion 2.94% w/w of rosiglitazone maleate is mixed with 87.80% w/w of Mannitol (Pearlitol SD 200 R.T.M.), 6.67% w/w of crosspovidone, 2.0% w/w of magnesium stearate, 0.56% w/w of colloidal silicon dioxide and 0.03% w/w ferric oxide red. This mixture is compressed to 90 mg weight tablets having a diameter of 6.35 mm.

Production of Outer Portion

Same as of Example 5.

Compression of tablets 90 mg granule of inner portion are pressed to tablets (equal to 2 mg rosiglitazone maleate) using 6.35 mm round punches and 1281 mg granule of outer portion (equal to 1000 mg metformin hydrochoride) are compressed using 20.3×9.8 mm oval punches. The compression procedure is same as Example 5.

The dissolution rate of the novel dosage form was determined

TABLE 13

Dissolution profile

| Metformin Hydrochloride | | Rosiglitazone Maleate | |
| --- | --- | --- | --- |
| Time (hour) | % Released | Time (min) | % Released |
| 1 | 38.29 | 15 | 80.2 |
| 2 | 53.40 | 30 | 96.1 |
| 4 | 69.51 | 45 | 103.4 |
| 6 | 78.11 | | |
| 8 | 86.86 | | |
| 10 | 93.60 | | |
| 12 | 97.65 | | |
| 24 | 100.17 | | |

Example 9

Production of Inner Portion 1.11% w/w of glimepiride is mixed with 63.28% w/w of lactose monohydrate and 22.22% w/w starch and the mixture is granulated in a binder of 2.22% w/w povidone in water and then dried. The granules are sieved and mixed with 1.11% w/w magnesium stearate, 10.0% w/w sodium starch glycolate, 0.06% w/w lake of brilliant blue. This mixture is compressed to 90 mg weight tablets having a diameter of 6.35 mm.

Production of Outer Portion

A) Micro matrix particle—83.33% w/w of metformin hydrochloride is mixed with 16.67% w/w of Eudragit RS (Ammonio Methacrylate Copolymer type B USP) and the mixture is granulated with a solvent mixture of acetone and methylene chloride and then dried. The granules are sized.

Coating of Micro matrix particles-86.46% w/w of micro matrix particles is charged in fluidized bed processor.

12.61% w/w of hydrogenated castor oil is dissolved in acetone and this coating solution is sprayed to coat the micro matrix particles. The coated micro matrix particles are sieved and mixed with 0.91% w/w magnesium stearate.

Compression of Tablets 90 mg granule of inner portion are pressed to tablets (equal to 1 mg glimepiride) using 6.35 mm round punches and 694 mg granules of outer portion (equal to 500 mg metformin hydrochloride) are compressed using 14.95×8.35 mm oblong punches. The compression procedure is same as Example 5.

The dissolution rate of the novel dosage form was determined

TABLE 14

Dissolution profile

| Metformin Hydrochloride | | Glimepiride | |
| --- | --- | --- | --- |
| Time (hour) | % Released | Time (min) | % Released |
| 1 | 28.0 | 15 | 69.4 |
| 2 | 40.5 | 30 | 91.87 |
| 4 | 57.8 | 45 | 99.64 |
| 6 | 65.8 | 60 | 103.87 |
| 8 | 73.2 | | |
| 10 | 80.3 | | |
| 12 | 85.0 | | |
| 24 | 101.8 | | |

Example 10

1) Production of Inner Portion
Same as for Example 5
2) Production of Outer Portion
Micro Matrix Particles—
Same as for Example 5
B) Coating of Micro matrix particles—91.21% w/w of micro matrix particles and 8.29% w/w of hydrogenated castor oil is mixed and charged in planetary mixer which is heated from outside to maintain the temperature approximately 80° C. with the help of a water bath. The above blend is mixed by running the planetary mixer for 1 hour to coat the micro matrix particles. The coated micro matrix particles are sieved and mixed with 0.50% w/w magnesium stearate.
3) Compression of Tablets
90 mg granule of inner portion are pressed to tablets (equal to 4 mg rosiglitazone maleate) using 6.35 mm round punches and 1206 mg granules of outer portion (equal to 1000 mg metformin hydrochloride) are compressed using 20.3×9.8 mm oval punches. The compression procedure is same as Example 5.

The dissolution rate of the novel dosage form was determined

TABLE 15

Dissolution profile

| Metformin Hydrochloride | | Rosiglitazone Maleate | |
|---|---|---|---|
| Time (hour) | % Released | Time (min) | % Released |
| 1 | 25.7 | 30 | 85.9 |
| 2 | 36.6 | 45 | 100.3 |
| 4 | 49.1 | 60 | 104.9 |
| 6 | 57.5 | | |
| 8 | 66.5 | | |
| 10 | 71.3 | | |
| 12 | 76.0 | | |
| 14 | 90.7 | | |

Dosage forms described in the example 11 are prepared by not coating the micro matrix particles of the outer portion but the hydrophobic release controlling agent is mixed with the micro matrix particles. The sole purpose of these examples is to demonstrate the usefulness of the present invention as described earlier. The examples clearly show that the rate of release of the modified release active ingredient is significantly faster than the present invention.

Example 11

1) Production of Inner Portion
   Same as for Example 5
2) Production of Outer Portion 77.76% w/w of metformin hydrochloride is mixed with 7.780% w/w of Eudragit RS (Ammonio Methacrylate Copolymer type B USP) and the mixture is granulated with a solvent mixture of acetone and methylene chloride and then dried. The granules are sized and mixed with 13.61% w/w of hydrogenated castor oil and 0.86% w/w of magnesium stearate.

3) Compression of Tablets
Tablet (A)—Same as for Example 5
Tablet (B)—Same as for Example 5

The dissolution rate of the novel dosage form was determined (Table 16 and 17)

TABLE 16

Dissolution profile of tablet (A)

| Metformin hydrochloride | | Rosiglitazone | |
|---|---|---|---|
| Time (hour) | % Released | Time (min) | % Released |
| 1 | 63.9 | 15 | 100.08 |
| 2 | 85.5 | 30 | 106.41 |
| 4 | 102.1 | 45 | 109.77 |

TABLE 17

Dissolution profile of tablet (B)

| Metformin hydrochloride | | Rosiglitazone | |
|---|---|---|---|
| Time (hour) | % Released | Time (min) | % Released |
| 1 | 50.3 | 15 | 99.22 |
| 2 | 70.5 | 30 | 105.26 |
| 4 | 88.0 | 45 | 107.53 |
| 6 | 100.9 | 60 | 107.53 |

Example 12

Production of Inner Portion
Same as for Example 7.
Production of Outer Portion
A) Micro matrix particles-93.02% w/w of metformin hydrochloride is mixed with 6.98% w/w of Eudragit RS (Ammonio Methacrylate Copolymer type B USP) and the mixture is granulated with a solvent mixutre of acetone and methylene chloride and then dried. The granules are sized.
B) Coating of Micro matrix particles—85.18% w/w of micro matrix particles is charged in fluidized bed processor. 13.87% w/w of hydrogenated castor oil is dissolved in acetone and this coating solution is sprayed to coat the micro matrix particles. The coated micro matrix particles are sieved and mixed with 0.95% w/w magnesium stearate.
3) Compression of Tablets 90 mg granule of inner portion are pressed to tablets (equal to 4 mg rosiglitazone) using 6.35 mm round punches and 1262 mg granules of outer portion (equal to 1000 mg metformin hydrochloride) are compressed using 20.3×9.8 mm oblong punches. The compression procedure is same as Example 5.

The dissolution rate of the novel dosage form was determined

TABLE 18

Dissolution profile

| Metformin Hydrochloride | | Rosiglitazone | |
|---|---|---|---|
| Time (hour) | % Released | Time (min) | % Released |
| 1 | 40.9 | 45 | 89.68 |
| 2 | 52.2 | 60 | 91.42 |
| 4 | 68.4 | | |
| 6 | 79.2 | | |
| 8 | 88.6 | | |
| 10 | 99.9 | | |
| 12 | 101.5 | | |

Example 13

Production of Inner Portion
Same as for Example 7.
Production of Outer Portion
A) Micro matrix particles—Same as for Example 12.
B) Coating of Micro matrix particles-88.70% w/w of micro matrix particles is charged in fluidized bed processor. 10.31% w/w of hydrogenated castor oil is dissolved in acetone and this coating solution is sprayed to coat the micro matrix particles. The coated micro matrix particles are sieved and mixed with 0.99% w/w magnesium stearate.

Compression of Tablets 90 mg granule of inner portion are pressed to tablets (equal to 4 mg rosiglitazone) using 6.35 mm round punches and 1212 mg granules of outer portion (equal to 1000 mg metformin hydrochloride) are compressed using 20.3×9.8 mm oblong punches. The compression procedure is same as Example 5.

The dissolution rate of the novel dosage form was determined (Table 19)

TABLE 19

Dissolution profile

| Metformin Hydrochloride | | Rosiglitazone | |
|---|---|---|---|
| Time (hour) | % Released | Time (min) | % Released |
| 1 | 44.50 | 15 | 79.9 |
| 2 | 58.90 | 30 | 89.9 |
| 4 | 76.90 | 45 | 95.8 |
| 6 | 91.40 | 60 | 100.6 |
| 8 | 102.40 | | |

Example 14

Production of Inner Portion
Same as for Example 11.
Production of Outer Portion
A) Micro matrix particles—Same as for Example 12.
B) Coating of Micro matrix particles-90.56% w/w of micro matrix particles is charged in fluidized bed processor. 8.42% w/w of hydrogenated castor oil is dissolved in acetone and this coating solution is sprayed to coat the micro matrix particles. The coated micro matrix particles are sieved and mixed with 1.01% w/w magnesium stearate.

Compression of Tablets 90 mg granule of inner portion are pressed to tablets (equal to 4 mg rosiglitazone) using 6.35 mm round punches and 1187 mg granules of outer portion (equal to 1000 mg metformin hydrochloride) are compressed using 20.3×9.8 mm oblong punches. The compression procedure is same as Example 5.

The dissolution rate of the novel dosage form was determined (Table 20)

TABLE 20

Dissolution profile

| Metformin Hydrochloride | | Rosiglitazone | |
|---|---|---|---|
| Time (hour) | % Released | Time (min) | % Released |
| 1 | 42.40 | 45 | 86.05 |
| 2 | 58.1 | 60 | 90.73 |
| 4 | 75.9 | | |
| 6 | 86.5 | | |
| 8 | 94.5 | | |
| 10 | 99.0 | | |

Example 15

Production of Inner Portion
Same as for Example 7.
Production of Outer Portion
A) Micro matrix particles-90.91% w/w of metformin hydrochloride is mixed with 4.55% w/w of Eudragit RS (Ammonio Methacrylate Copolymer type B USP) and 4.55% w/w of Eudragit RL (Ammonio Methacrylate Copolymer type A USP) and the mixture is granulated with a solvent mixture of acetone and methylene chloride and then dried. The granules are sized.

B) Coating of Micro matrix particles—85.47% w/w of micro matrix particles is charged in fluidized bed processor. 13.60% w/w of hydrogenated castor oil is dissolved in acetone and this coating solution is sprayed to coat the micro matrix particles. The coated micro matrix particles are sieved and mixed with 0.93% w/w magnesium stearate.

Compression of Tablets 90 mg granule of inner portion are pressed to tablets (equal to 4 mg rosiglitazone) using 6.35 mm round punches and 1287 mg granules of outer portion (equal to 1000 mg metformin hydrochloride) are compressed using 20.3×9.8 mm oblong punches. The compression procedure is same as Example 5.

The dissolution rate of the novel dosage form was determined (Table 21)

TABLE 21

Dissolution profile

| Metformin Hydrochloride | | Rosiglitazone | |
|---|---|---|---|
| Time (hour) | % Released | Time (min) | % Released |
| 1 | 34.8 | 45 | 92.65 |
| 2 | 48.3 | 60 | 97.02 |
| 4 | 66.2 | | |
| 6 | 79.3 | | |
| 8 | 85.9 | | |
| 10 | 92.6 | | |
| 12 | 97.6 | | |

Example 16

Production of Inner Portion
Same as for Example 7.
Production of Outer Portion
A) Micro matrix particles—Same as for Example 15.
B) Coating of Micro matrix particles-94.66% w/w of micro matrix particles is charged in fluidized bed processor. 4.30% w/w of hydrogenated castor oil is dissolved in acetone and this coating solution is sprayed to coat the micro matrix particles. The coated micro matrix particles are sieved and mixed with 1.03% w/w magnesium stearate.

Compression of Tablets 90 mg granule of inner portion are pressed to tablets (equal to 4 mg rosiglitazone) using 6.35 mm round punches and 1162 mg granules of outer portion (equal to 1000 mg metformin hydrochloride) are compressed using 20.3×9.8 mm oblong punches. The compression procedure is same as Example 5.

The dissolution rate of the novel dosage form was determined (Table 22)

TABLE 22

| Dissolution profile | | | |
|---|---|---|---|
| Metformin Hydrochloride | | Rosiglitazone | |
| Time (hour) | % Released | Time (min) | % Released |
| 1 | 47.56 | 45 | 92.94 |
| 2 | 61.93 | 60 | 96.70 |
| 4 | 82.42 | | |
| 6 | 96.0 | | |
| 8 | 100.0 | | |

Example 17

1) Production of Inner Portion
   Same as for Example 7.
2) Production of Outer Portion
A) Micro matrix particles—Same as for Example 5.
B) Coating of Micro matrix particles-88.92% w/w of micro matrix particles is charged in fluidized bed processor. 10.11% w/w of hydrogenated castor oil is dissolved in acetone and this coating solution is sprayed to coat the micro matrix particles. The coated micro matrix particles are sieved and mixed with 0.97% w/w magnesium stearate.
3) Compression of Tablets
90 mg granule of inner portion are pressed to tablets (equal to 4 mg rosiglitazone) using 6.35 mm round punches and 1237 mg granules of outer portion (equal to 1000 mg metformin hydrochloride) are compressed using 20.3×9.8 mm oblong punches. The compression procedure is same as Example 5.

The dissolution rate of the novel dosage form was determined (Table 23)

TABLE 23

| Dissolution profile | | | |
|---|---|---|---|
| Metformin Hydrochloride | | Rosiglitazone | |
| Time (hour) | % Released | Time (min) | % Released |
| 1 | 35.0 | 15 | 69.2 |
| 2 | 47.3 | 30 | 79.5 |
| 4 | 60.8 | 45 | 85.7 |
| 6 | 72.5 | 60 | 90.4 |
| 8 | 81.8 | | |
| 10 | 89.2 | | |
| 12 | 94.1 | | |
| 24 | 98.2 | | |

Example 18

1) Production of Inner Portion
   Same as for Example 7.
2) Production of Outer Portion
A) Micro matrix particles—Same as for Example 5.
B) Coating of Micro matrix particles-87.09% w/w of micro matrix particles is charged in fluidized bed processor. 11.88% w/w of hydrogenated castor oil is dissolved in acetone and this coating solution is sprayed to coat the micro matrix particles. The coated micro matrix particles are sieved and mixed with 1.03% w/w magnesium stearate.
3) Compression of Tablets
90 mg granule of inner portion are pressed to tablets (equal to 4 mg rosiglitazone) using 6.35 mm round punches and 1263 mg granules of outer portion (equal to 1000 mg metformin hydrochloride) are compressed using 20.3×9.8 mm oblong punches. The compression procedure is same as Example 5.

The dissolution rate of the novel dosage form was determined (Table 24)

TABLE 24

| Dissolution profile | | | |
|---|---|---|---|
| Metformin Hydrochloride | | Rosiglitazone | |
| Time (hour) | % Released | Time (min) | % Released |
| 1 | 38.7 | 30 | 78.66 |
| 2 | 52.9 | 45 | 83.47 |
| 4 | 71.6 | 60 | 88.06 |
| 6 | 82.3 | | |
| 8 | 91.3 | | |
| 10 | 97.3 | | |
| 12 | 101.1 | | |

Example 19

Production of Inner Portion
2.22% w/w of glimepiride is mixed with 62.17% w/w of lactose monohydrate and 22.22% w/w starch and the mixture is granulated in a binder of 2.22% w/w povidone in water and then dried. The granules are sieved and mixed with 0.56% w/w magnesium stearate, 10.0% w/w sodium starch glycolate, 0.06% w/w lake of erythrocine and 0.56% w/w colloidal silicon dioxide. This mixture is compressed to 90 mg weight tablets having a diameter of 6.35 mm. Production of outer portion—same as for example 18.

Compression of tablets
90 mg granule of inner portion are pressed to tablets (equal to 2 mg glimepiride) using 6.35 mm round punches and 1263 mg granules of outer portion (equal to 1000 mg metformin hydrochloride) are compressed using 20.3×9.8 mm oblong punches. The compression procedure is same as Example 5.

The dissolution rate of the novel dosage form was determined (Table 25)

TABLE 25

| Dissolution profile | | | |
|---|---|---|---|
| Metformin Hydrochloride | | Glimepiride | |
| Time (hour) | % Released | Time (min) | % Released |
| 1 | 38.79 | 45 | 100.7 |
| 2 | 54.12 | 60 | 102.2 |
| 4 | 69.54 | | |
| 6 | 82.04 | | |
| 8 | 89.78 | | |
| 10 | 95.06 | | |
| 12 | 100.48 | | |

Example 20

Determination of relative bioavailability of Metformin sustained release formulation with respect to metformin immediate release tablet.

The study was carried out to demonstrate the sustained release characteristic of metformin in the combination formulation and to evaluate the relative bioavailability of combination formulation of sustained release Metformin hydrochloride and Rosiglitazone maleate versus metformin immediate release tablet 2×500 mg (marketed as Glycomet? by USV Ltd.; India.) and rosiglitazone immediate release tablets 4 mg (marketed as Enselin? by Torrent pharma Ltd.; India.).

Methodology:

The biostudy had an open label, randomized two period, two treatment, two way single dose crossover study with 7 days washout period between treatment days.

Non-compartmental Pharmacokinetic assessment was based on the plasma levels of Metformin and Rosiglitazone measured by blood sampling. Blood samples were obtained before dosing and at the following times after administration of test and reference formulations;

Pre-dose, 0.5, 0.75, 1.0, 1.5, 2.0, 3.0, 3.5, 4.0, 5.0, 6.0, 8.0, 10.0, 12.0, 15.0, 18.0, and 24.0 hours.

Number of Subjects and Study Population:

Twelve (12) volunteers were enrolled and all of them completed the study. All 12 volunteers were included in the Pharmacokinetic and safety analyses.

Criteria for Inclusion:

Healthy male volunteers aged between 18 to 45 years.

Test Formulation, Dose and Mode of Administration:

Test Formulation: 4 mg/1000 mg Rosiglitazone/Metformin SR prepared as per the invention disclosed in the examples.

Volunteers received a single oral dose of above products with 200 ml of water following high calorie diet (~800 Kcal).

Reference Product, Dose and Mode of Administration:

Reference: Immediate release 4 mg Enselin[?] plus Glycomate[?] (2×500 mg)

Volunteers received a single oral dose of above products with 200 ml of water following high calorie diet (~800 Kcal).

Pharmacokinetics:

The following Pharmacokinetic parameters were calculated using non compartments methods: the area under the drug plasma concentration curve from time of dosing to the time of last sampling point ($AUC_{(0-t)}$); the area under the drug plasma concentration versus time curve extrapolated to infinity ($AUC_{(0-Inf.)}$); the maximum measured concentration of the drug in the plasma ($C_{max}$) and the time at which this concentration was measured ($t_{max}$); the concentration at 24 hours ($C_{24h}$); the time taken for drug plasma concentration to decrease by 50% ($t_{1/2}$); and the terminal first-order elimination rate constant ($K_{el}$).

Area Under the curve (AUC) is the integral part of drug blood level over time from zero to infinity and is a measure of quantity of drug absorbed and in the body.

AUC (0-t) represents area under the curve from zero to time t, where t represents the time at which last blood sample was taken.

AUC ($0-_{Inf}$) represents area under the curve from zero to infinity.

Elimination half life of a drug is the time in hours necessary to reduce the drug concentration in the blood, plasma or serum to ½ after equilibrium is reached.

$C_{max}$ is the peak plasma concentration achieved after the administration of the drug.

$T_{max}$ is the time to reach peak plasma concentration.

Statistical Methods:

Descriptive statistics of relevant Pharmacokinetic parameters were performed. An analysis of variance (ANOVA) was used to assess treatment differences.

Methods used for analysis of Metformin and Rosiglitazone in plasma samples:

Analysis of Metformin:

Estimation of Metformin in plasma samples was carried out by High Performance Liquid Chromatography and UV detection at 234 nm. Briefly 0.5 ml of plasma sample was precipitated with 2.0 ml acetonitrile. Samples were centrifuged and supernatant aliquot was washed with dichloromethane. After centrifugation, aqueous layer was injected on HPLC.

Analysis of Rosiglitazone:

Estimation of Rosiglitazone in plasma samples was carried out by LC-MS/MS. Briefly 0.1 ml of plasma sample was precipitated with 0.25 ml acetonitrile. Samples were centrifuged and supernatant aliquot was analyzed by LC-MS/MS.

Figure 8:
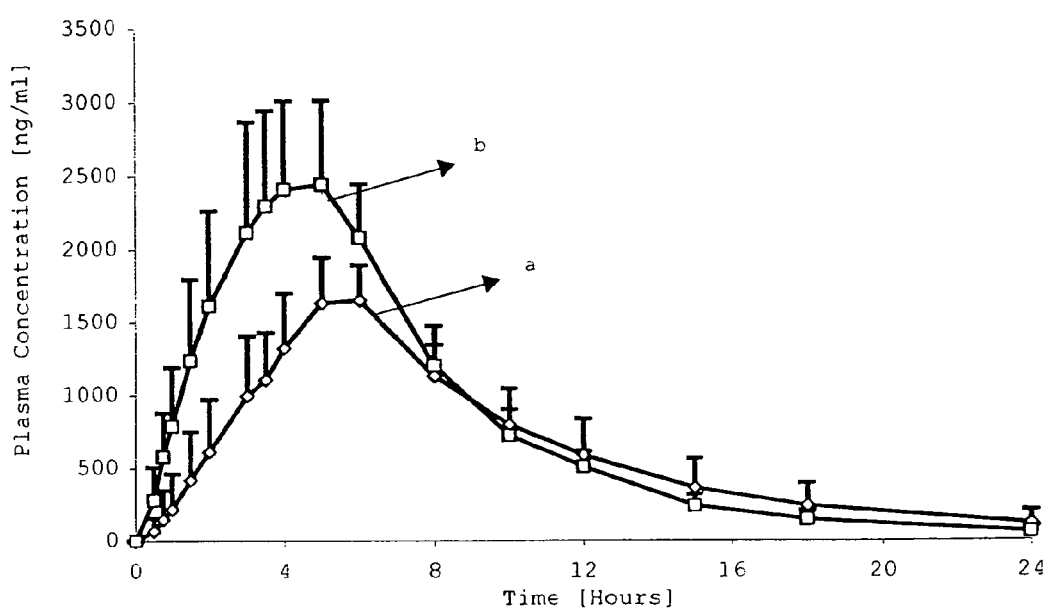
FIG. 8 is a plot of metformin plasma concentration versus time for test (a) and reference (b) formulation.
Figure 9:
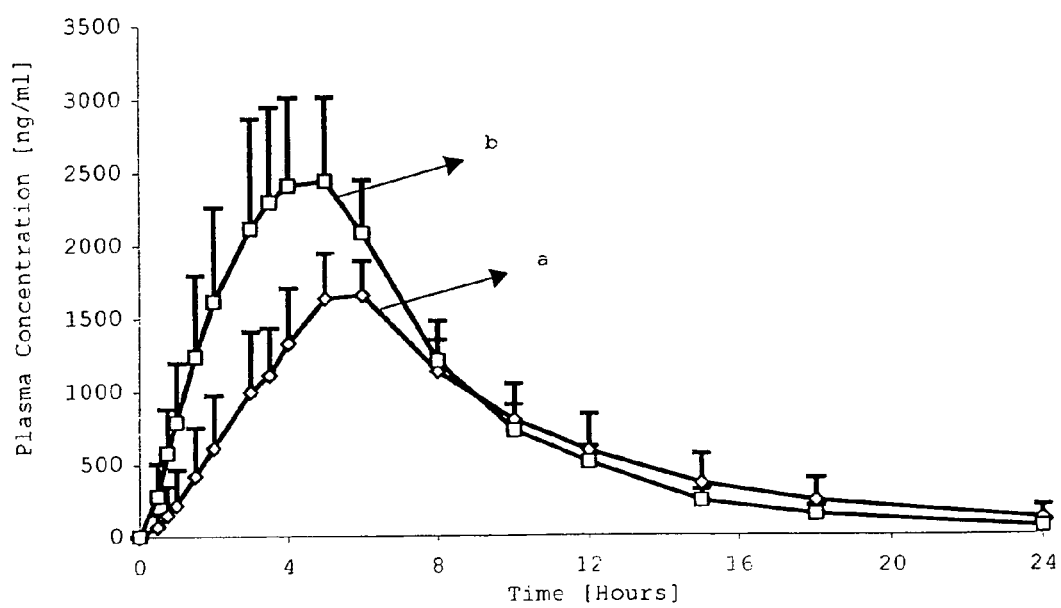
FIG. 9 is a plot of rosiglitazone plasma concentration versus time for test (a) and reference (b) formulation.

Pharmacokinetic Results:

The summary of the statistical analysis and confidence intervals of the Pharmacokinetic parameters is contained in Tables 26 & 27. The mean plasma concentration versus time curve is depicted in FIG. 8 (metformin) & FIG. 9 (rosiglitazone) wherein curve a represents Test Formulation and curve b represents Reference Formulation.

TABLE 26

Bioavailability Summary and Analysis - Metformin SR

| | | | |
|---|---|---|---|
| $AUC_{0-inf}$ | ng * hr | 15980 + 3456 | 19551 + 4265 |
| $AUC_{0-t}$ | ng * hr | 14983 + 2930 | 19091 + 4200 |
| $C_{max}$ | ng/ml | 1737.61 + 249.09 | 2558.37 + 623.05 |
| $C_{24h}$ | ng/ml | 113.87 + 91.05 | 56.44 + 37.94 |
| $T_{max}$ | hr | 5.42 + 0.68 | 4.42 + 0.88 |
| $T_{1/2}$ | hr | 4.71 + 1.36 | 4.26 + 1.14 |

TABLE 27

Bioavailability Summary and Analysis -

| | | | |
|---|---|---|---|
| $AUC_{0-inf}$ | ng * hr/ml | 1851 + 414 | 1730 + 465 |
| $AUC_{0-t}$ | ng * hr/ml | 1795 + 401 | 1676 + 438 |
| $C_{max}$ | ng/ml | 243.48 + 40.78 | 247.48 + 45.38 |
| $C_{24h}$ | ng/ml | 6.36 + 5.19 | 3.37 + 4.36 |
| $T_{max}$ | hr | 3.75 + 1.03 | 3.25 + 1.66 |
| $t_{1/2}$ | hr | 3.73 + 0.60 | 3.63 + 0.79 |

Conclusion:

Metformin in test formulation has shown sustained release characteristics with lower $C_{max}$ and prolonged $t_{max}$ (Figure 8). The relative bioavailability of both the components was studied.

Example 21

Determination of Relative Bioavailability of Two Formulations with Different Release Profiles:

A biostudy was carried out with the preliminary objective of comparing the relative bioavailability of the 1000 mg metformin sustained release formulations (A & B) relative to immediate release metformin tablets 2×500 mg (marketed as Glycomet[?] by USV Ltd.; India.). A secondary objective was to characterize the plasma concentration profile of metformin in the sustained release formulation relative to immediate release formulation i.e. Glycomet[?] 2×500 mg tablets.

Methodology:

The biostudy had an open label, randomized, three periods, three treatment, three way, single dose crossover design with 7 days washout period between treatment days.

Non-compartmental Pharmacokinetic assessment was based on the plasma levels of metformin measured by blood sampling. Blood samples were obtained before dosing and at the following times after administration of test and reference formulations;

Pre-dose, 0.5, 0.75, 1.0, 1.5, 2.0, 3.0, 3.5, 4.0, 5.0, 6.0, 8.0, 10.0, 12.0, 15.0, and 24.0 hours.

Number of Subjects and Study Population:

Twelve (12) volunteers were enrolled and 11 of them completed the study. All 12 volunteers were included in the Pharmacokinetic and safety analyses.

Criteria for Inclusion:

Healthy male volunteers aged between 18 to 45 years.

Test product, Dose and Mode of Administration:

Formulation A: 4 mg/1000 mg Rosiglitazone/Metformin dosage form prepared as per the invention disclosed in the examples. Formulation B: 4 mg/1000 mg Rosiglitazone/Metformin SR dosage form prepared as per the invention disclosed in the examples.

In the morning, volunteers received a single oral dose of above products with 200 ml of water following high calorie diet (~800 Kcal).

Reference Product, Dose and Mode of Administration:

Formulation C: Immediate release 4 mg Enselin? plus Glycomate? (2×500 mg)

In the morning, volunteers received a single oral dose of above products with 200 ml of water following high calorie diet (~800 Kcal)

Pharmacokinetics:

Same as for example 20.

Statistical Methods:

Same as for example 20.

Methods used for analysis of Metformin and Rosiglitazone in plasma samples:

Same as for example 20.

Pharmacokinetic Results:

The summary of the statistical analysis and confidence intervals of the Pharmacokinetic parameters is contained in

TABLE 28

Figure 10:
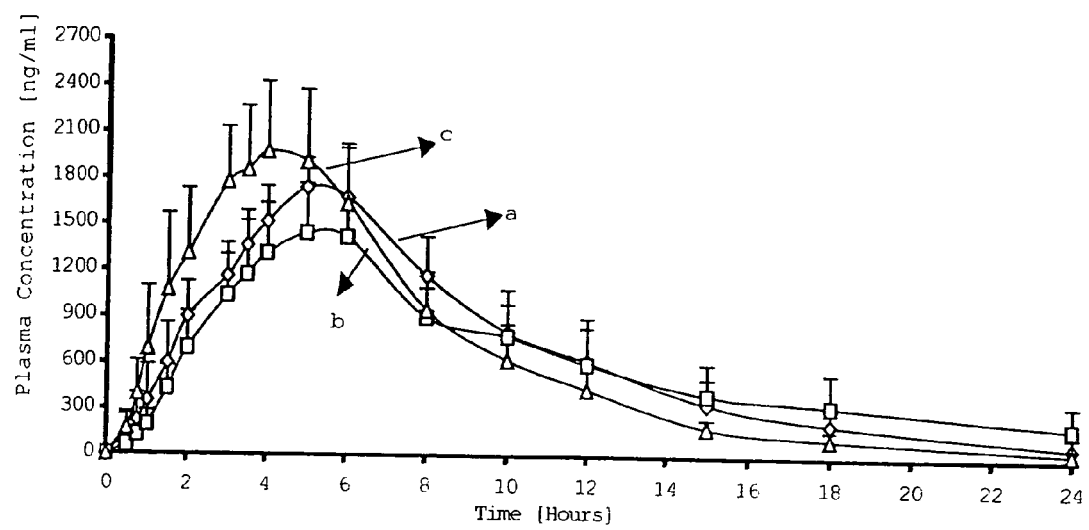
FIG. 10 is a plot of metformin plasma concentration versus time for test (a and b) and reference (c) formulation.

The mean plasma concentration versus time curve is depicted in FIG. 10. wherein curve a represents Formulation A, curve b represents Formulation B and curve c represents the Formulation C.

| | | | | |
|---|---|---|---|---|
| $AUC_{0-inf}$ | ng * hr/m | 16508+ | 17762+ | 15985+ |
| $AUC_{0-t}$ | ng * hr/m | 15899+ | 14989+ | 15558+ |
| $C_{max}$ | ng/ml | 1801.72+ | 1551.01+ | 2121.96+ |
| $C_{24h}$ | ng/ml | 79.58+ | 204.96+ | 45.48+ |
| $T_{max}$ | Hr | 5.36 + 0.51 | 5.46 + 0.78 | 4.00 + 0.74 |
| $T_{1/2}$ | Hr | 4.08 + 1.32 | 7.23 + 3.45 | 4.61 + 1.54 |

Conclusion:

Both the formulations according to the invention tested had reduced $C_{max}$ compared to that of the reference product (Glycomet? tablets), with Formulation B being significantly reduced. The $t_{max}$ of both the formulations according to invention were prolonged relative to that of Glycomet? tablets. The concentration at 24 hours ($C_{24h}$) of Formulation B was almost 4.5 times higher than Glycomet? tablets and almost 2.6 times higher than Formulation A.

Example 22

Determination of Relative Bioavailability of Metformin Sustained Release Formulations The study was carried out to assess the effect of night time administration and to evaluate the relative bioavailability of combination formulation of sustained release Metformin and Rosiglitazone (prepared as per the invention disclosed in the examples) versus metformin sustained release tablet (marketed as Glucophage XR? by Bristol Myers Squibb; USA.) and rosiglitazone immediate release tablet (marketed as Avandia? by Glaxo Smithkline; United Kingdom.).

Methodology:

The biostudy had an open label, randomized two period, two treatment, two way single dose crossover study with 7 days washout period between treatment days.

Non-compartmental Pharmacokinetic assessment was based on the plasma levels of Metformin and Rosiglitazone measured by blood sampling. Blood samples were obtained before dosing and at the following times after administration of test and reference formulations;

Pre-dose, 0.5, 0.75, 1.0, 1.5, 2.0, 3.0, 3.5, 4.0, 5.0, 6.0, 8.0, 10.0, 12.0, 15.0, 18.0, and 24.0 hours.

Number of Subjects and Study Population:

Sixteen (16) volunteers were enrolled and 15 of them completed the study. All 15 volunteers were included in the Pharmacokinetic and safety analyses.

Criteria for Inclusion:

Healthy male volunteers aged between 18 to 45 years.

Test Product, Dose and Mode of Administration:

Test Formulation: 4 mg/1000 mg Rosiglitazone/Metformin sustained release dosage form prepared as per the invention disclosed in the examples. Volunteers received a single oral dose of above products with 200 ml of water following high calorie dinner (~1400 KCal).

Reference Product, Dose and Mode of Administration:

Reference: 4 mg Avandia? plus Glucophage XR? (2×500 mg) Volunteers received a single oral dose of above products with 200 ml of water following high calorie dinner (~1400 Kcal).

Pharmacokinetics:

Same as for example 20.

Statistical Methods:

Descriptive statistics of relevant Pharmacokinetic parameters were performed. An analysis of variance (ANOVA) was used to assess treatment differences.

Westlake's 90% confidence interval for the ratio of two formulations for log transformed data were calculated, and to test that the difference between two formulations are within the (80 to 125%) limits.

Methods used for analysis of Metformin and Rosiglitazone in plasma samples:

Same as for example 20.

Figure 11:
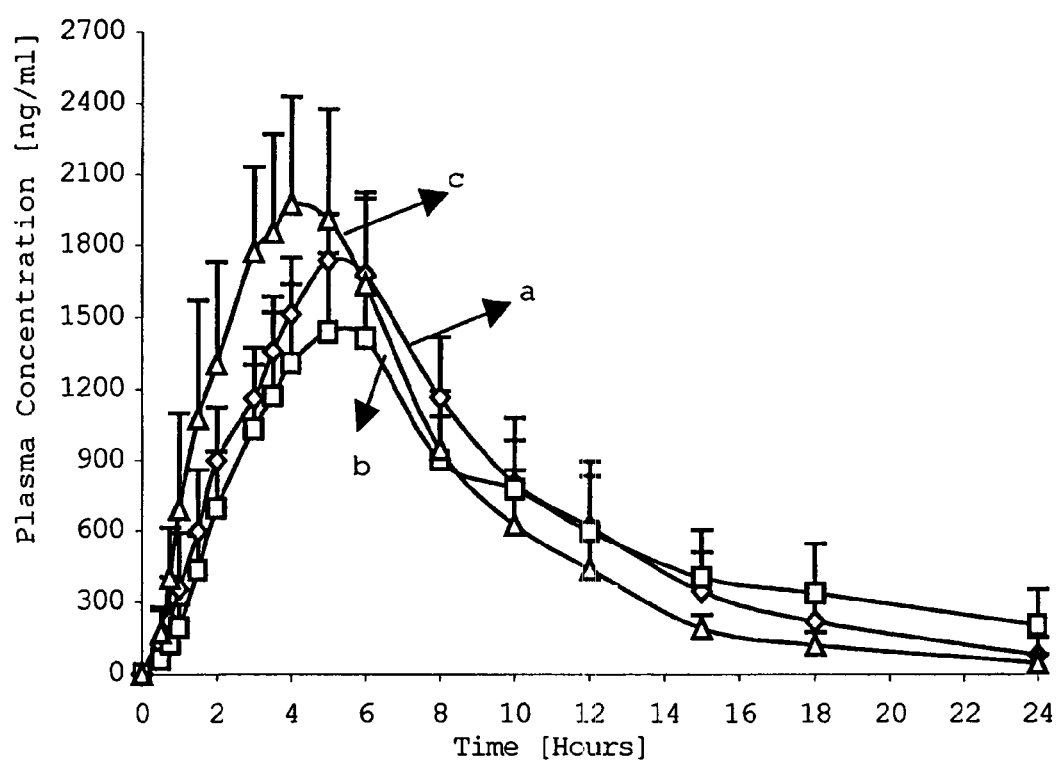
FIG. 11 is a plot of metformin plasma concentration versus time for test (a) and reference (b) formulation.

Pharmacokinetic Results:

The summary of the statistical analysis and confidence intervals of the Pharmacokinetic parameters is contained in Table 29 & 30. The mean plasma concentration versus time curve is depicted in FIG. 11 (Metformin) & 12 (Rosiglitazone) wherein curve a represents Test Formulation and curve b represents Reference Formulation.

TABLE 29

Bioavailability Summary and Analysis - Metformin SR

| | | | | | |
|---|---|---|---|---|---|
| $AUC_{0-inf}$ | ng*hr/m | 16939+ | 16396+ | 83.84 | 116.16 |
| $AUC_{0-t}$ | ng*hr/m | 16107+ | 15951+ | 87.33 | 112.67 |
| $C_{max}$ | ng/ml | 1515.29+ | 1558.78+ | 90.89 | 109.11 |
| $C_{24h}$ | ng/ml | 120.10+ | 79.63+ | — | — |
| $T_{max}$ | hr | 7.64+ | 8.86+ | — | — |
| $T_{1/2}$ | hr | 4.12+ | 3.36+ | — | — |

TABLE 30

Bioavailability Summary and Analysis - Rosiglitazone (4 mg)

| | | | | | |
|---|---|---|---|---|---|
| $AUC_{0-inf}$ | ng*hr/m | 1308+ | 1258 + 331 | 85.73 | 114.27 |
| $AUC_{0-t}$ | ng*hr/m | 1266+ | 1234 + 324 | 86.61 | 113.39 |
| $C_{max}$ | ng/ml | 145.70+ | 161.83+ | 80.88 | 119.12 |
| $C_{24h}$ | ng/ml | 6.07+ | 1.80 + 3.11 | — | — |
| $T_{max}$ | hr | 5.07+ | 4.13 + 1.91 | — | — |
| $T_{1/2}$ | hr | 3.59+ | 3.32 + 0.59 | — | — |

Figure 12:
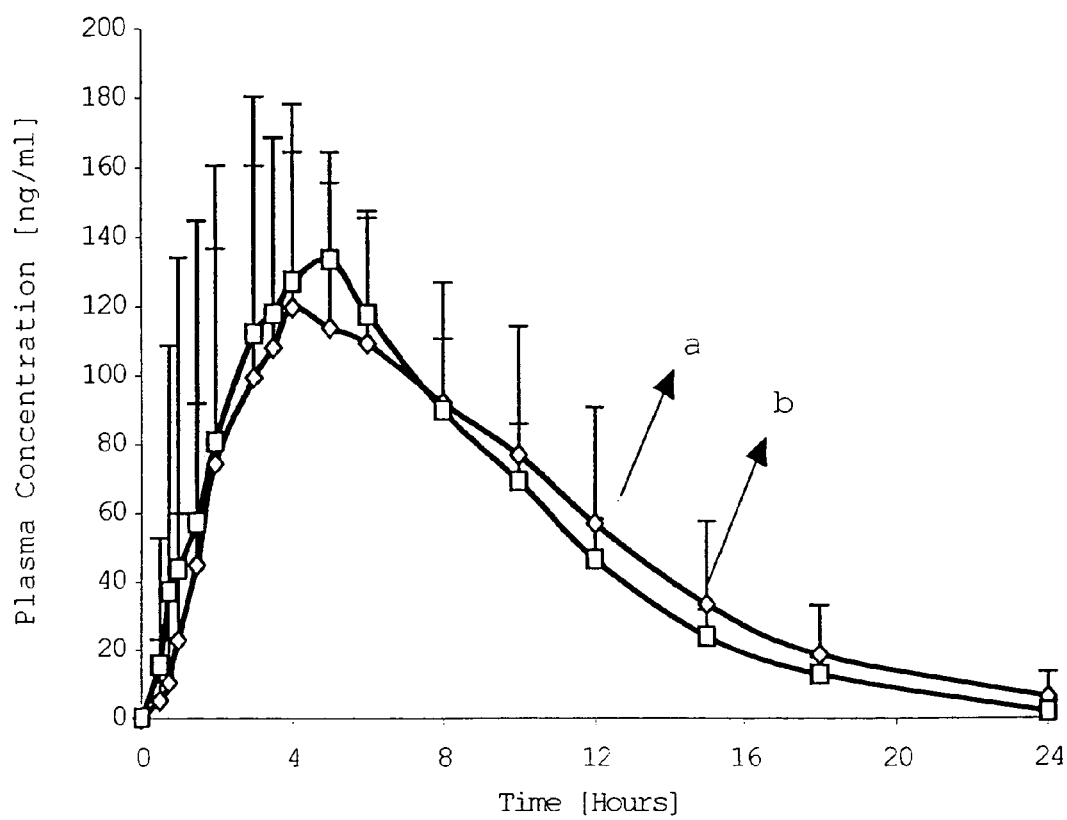
FIG. 12 is a plot of rosiglitazone plasma concentration versus time for test (a) and reference (b) formulation.

Conclusion:

The relative bioavailability study shown that bioequivalance was achieved between the 4 mg/1000 mg combination formulation and the respective components, for both AUC and $C_{max}$ parameters (Table 29 & 30). Moreover, in the test formulation, the concentration of Metformin at 24 hrs was almost 1.5 times more than Glucophage $XR^?$ (FIG. 11) wherein curve a represents Test formulation and b represents Reference formulation (Table 29). Similarly Rosiglitazone component of the test formulation also shown higher concentration at 24 hrs as that of $Avandia^?$ (FIG. 12; wherein curve a represents Test Formulation and curve b represents Reference Formulation and Table 30).

Example 23

1) Production of Inner Portion 69.61% w/w of Aspirin coated granules (Aspirin 96% w/w, 2.0% w/w hydrogenated castor oil & 2.0% w/w citric acid anhydrous coated) mixed with the mixture of 11.56% w/w of microcrystalline cellulose (PH112, dried), 7.17% w/w sodium starch Glycolate (dried), 2.24% w/w citric acid anhydrous, 4.48% w/w talc, 1.79% w/w colloidal silicon dioxide, 1.79% w/w stearic acid and 1.35% w/w hydrogenated vegetable oil.

Production of Outer Portion
A) Micro matrix particles—93.02% w/w of nicotinic acid is mixed with 6.98% w/w of Eudragit RS PO (Ammonio Methacrylate Copolymer type B USP) and the mixture is granulated with a solvent mixture of acetone and methylene chloride and then dried. The granules are sized through 11.0 mm screen.
B) Coating of Micro matrix particles-92.67% w/w of micro matrix particles is charged in fluidized bed processor. 6.47% w/w of hydrogenated castor oil is dissolved in acetone and this coating solution is sprayed to coat the micro matrix particles. The coated micro matrix particles are sieved and mixed with 0.86% w/w magnesium stearate.

Compression of Tablets
Tablet (A)—483.17 mg granules of inner portion are pressed to tablets (equal to 325.0 mg aspirin) using 15.0×6.35 mm plain, capsule shape punches with one side break line and 1160 mg granules of outer portion (equal to 1000 mg nicotinic acid) are compressed using 20.3×9.8 mm plain, capsule shape punches.
Tablet (B)—223.0 mg granules of inner portion are pressed to tablets (equal to 150.0 mg aspirin) using 13.5×6.35 mm plain, capsule shape punches with one side break line and 1160 mg granules of outer portion (equal to 1000 mg nicotinic acid) are compressed using 20.3×9.8 mm plain, capsule shape punches. The compression is done on press coater machine in such a manner that the resultant tablet has inner portion covered by the outer portion from all the sides except top surface that remains uncovered and the level of the inner portion and the outer portion is on the same surface.

What is claimed is:

1. A dosage form of combination of high dose high solubility active ingredient, as modified release and low dose active ingredient as immediate release suitable for swallowing; comprising an inner portion having a low dose active ingredient as immediate release and an outer portion having a high dose, high solubility active ingredient as modified release, wherein said inner portion is covered by the outer portion from all the sides except a top surface that remains uncovered; wherein the outer portion prepared by using dual retard technique to control the release of high dose, high solubility active ingredient, wherein the dual retard technique is a combination of matrix formulation and reservoir formulation comprises
   (a) micro matrix particles consisting of a high dose, high solubility active ingredient and one or more hydrophobic release controlling agents wherein the ratio of high dose, high solubility active ingredient and hydrphobic release controlling agent is in the range of 100:2.5 to 100:30 and
   (b) coating of one or more hydrophobic release controlling agents on said micro matrix particles, wherein the ratio of micro matrix particles and hydrophobic release controlling agent is in the range of 100:2.5 to 100:30 wherein the weight ratio of the immediate release low dose active ingredient and high dose, high solubility modified release active ingredient is from 1:1 to 1:15000 wherein the claimed dosage form does not provide burst release.

2. A dosage form according to claim 1, wherein the hydrophobic release controlling agents are selected from the group consisting of poly(ethyl acrylate, methyl methacrylate, trimethylammonioethyl methacrylate chloride) 1:2:0.1; poly (ethyl acrylate, methyl methacrylate, trimethylamonioethyl methacrylate chloride) 1:2:0.2 and poly(ethyl acrylate, methyl methacrylate) 1:1; polyvinyl acetate dispersion, ethylcellulose, cellulose acetate, cellulose propionate (lower, medium or higher molecular weight), cellulose acetate propionate, cellulose acetate butyrate, cellulose acetate phthalate, cellulose triacetate, poly(methyl methacrylate), poly (ethyl methacrylate), poly(butyl methacrylate), poly(isobutyl methacrylate), poly (hexyl methacrylate), poly(isodecyl methacrylate), poly (lauryl methacrylate), poly(phenyl methacrylate), poly (methyl acrylate), poly (isopropyl acrylate), poly (isobutyl actylate), poly (octadecyl acrylate), waxes selected from the group consisting of beeswax, carnauba wax, selected from the group consisting of cetostearyl alcohol, stearyl alcohol; cetyl alcohol and myristyl alcohol; and fatty acid esters glyceryl monostearate, glycerol distearate, glycerol monooleate, acetylated monoglycerides, tristearin, tripalmitin, cetyl esters wax, glyceryl palmitostearate, glyceryl behenate and hydrogenated castor oil.

3. A dosage form according to claim 2, wherein the hydrophobic release controlling agent(s) is selected from the group consisting of poly(ethyl acrylate, methyl methacrylate, trimethylammonioethyl methacrylate chloride) 1:2:0.1; poly (ethyl acrylate, methyl methacrylate, trimethylamonioethyl methacrylate chloride) 1:2:0.2 and poly(ethyl acrylate, methyl methacrylate) 1:1.

4. A dosage form according to claim 3, wherein the hydrophobic release controlling agent is poly(ethyl acrylate, methyl methacrylate, trimethylammonioethyl methacrylate chloride) 1:2:0.1.

5. A dosage form according to claim 1, wherein in micro matrix particles, the active ingredient and one or more hydrophobic release controlling agents are present in a ratio of from 100:2.5 to 100:20.

6. A dosage form according to claim 3, wherein the hydrophobic release controlling agents are selected from the group consisting of poly(ethyl acrylate, methyl methacrylate, trimethylammonioethyl methacrylate chloride) 1:2:0.1; poly (ethyl acrylate, methyl methacrylate, trimethylamonioethyl methacrylate chloride) 1:2:0.2 and poly(ethyl acrylate, methyl methacrylate) 1:1; polyvinyl acetate dispersion, ethylcellulose, cellulose acetate, cellulose propionate (lower, medium or higher molecular weight), cellulose acetate propionate, cellulose acetate butyrate, cellulose acetate phthalate, cellulose triacetate, poly(methyl methacrylate), poly (ethyl methacrylate), poly(butyl methacrylate), poly(isobutyl methacrylate), poly (hexyl methacrylate), poly(isodecyl methacrylate), poly (lauryl methacrylate), poly(phenyl methacrylate), poly (methyl acrylate), poly (isopropyl acrylate), poly (isobutyl actylate), poly (octadecyl acrylate), waxes selected from the group consisting of beeswax, carnauba wax, microcrystalline wax, and ozokerite; fatty alcohols selected from the group consisting of cetostearyl alcohol, stearyl alcohol; cetyl alcohol and myristyl alcohol; and fatty acid esters selected from the group consisting of glyceryl monostearate, glycerol distearate, glycerol monooleate, acetylated monoglycerides, tristearin, tripalmitin, cetyl esters wax, glyceryl palmitostearate, glyceryl behenate glycerol distearate, and hydrogenated castor oil.

7. A dosage form according to claim 6, wherein the hydrophobic release controlling agent(s) is selected from fatty acids selected from the group consisting of glyceryl monostearate, glycerol distearate, glycerol monoleate, acetylated monoglycerides, tristearin, tripalmitin, cetyl esters wax, glyercyl palmitostearate, glyceryl behenate, glycerol distearate, and hydrogenated castor oil.

8. A dosage form according to claim 7, wherein the hydrophobic release controlling agents is selected from the group consisting of hydrogenated castor oil and glycerol distearate.

9. A dosage form according to claim 1, wherein the low dose active ingredient comprises dose less than or equal to 500 mg.

10. A dosage form according to claim 1, wherein the low dose active ingredient is selected from the group consisting of adrenergic agent; adrenocortical steroid; adrenocortical suppressant; aldosterone antagonist; amino acid; anabolic; analeptic; analgesic; anesthetic; anorectic; anti-acne agent; anti-adrenergic; anti-allergic; anti-amebic; anti-anemic; anti-anginal; anti-arthritic; anti-asthmatic; anti-atherosclerotic; antibacterial; anticholinergic; anticoagulant; anticonvulsant; antidepressant; antidiabetic; antidiarrheal; antidiuretic; antiemetic; anti-epileptic; antifibrinolytic; antifungal; antihemorrhagic; antihistamine; antihyperlipidemia; antihypertensive; antihypotensive; anti-infective; anti-inflammatory; antimicrobial; antimigraine; antimitotic; antimycotic, antinauseant, antineoplastic, antineutropenic, antiparasitic; antiproliferative; antpsychotic; antirheumatic; antiseborrheic; antisecretory; antispasmodic; antithrombotic; anti-ulcerative; antiviral; appetite suppressant; blood glucose regulator; bone resorption inhibitor; bronchodilator; cardiovascular agent; cholinergic; depressant; diagnostic aid; diuretic; dopaminergic agent; estrogen receptor agonist; fibrinolytic; fluorescent agent; free oxygen radical scavenger; gastric acid supressant; gastrointestinal motility effector; glucocorticoid; hair growth stimulant; hemostatic; histamine H2 receptor antagonists; hormone; hypocholesterolemic; hypoglycemic; hypolipidemic; hypotensive; imaging agent; immunizing agent; immunomodulator; immunoregulator; immunostimulant; immunosuppressant; keratolytic; LHRH agonist; mood regulator; mucolytic; mydriatic; nasal decongestant; neuromuscular blocking agent; neuroprotective; NMDA antagonist; non-hormonal sterol derivative; plasminogen activator; platelet activating factor antagonist; platelet aggregation inhibitor; psychotropic; radioactive agent; scabicide; sclerosing agent; sedative; sedative-hypnotic; selective adenosine A1 antagonist; serotonin antagonist; serotonin inhibitor; serotonin receptor antagonist; steroid; thyroid hormone; thyroid inhibitor; thyromimetic; tranquilizer; amyotrophic lateral sclerosis agent; cerebral ischemia agent; Paget's disease agent; unstable angina agent; vasoconstrictor; vasodilator; wound healing agent; and xanthine oxidase inhibitor.

11. A dosage form according to claim 10, wherein the low dose active ingredient is selected from the group consisting of 16-alpha fluorocstradiol, 16-alpha-gitoxin, 16-epiestriol, 17 alpha dihydroequilenin, 17 alpha estradiol, 17 beta estradiol, 17 hydroxy progesterone, 1alpha-hydroxyvitamin D2, 1-dodecpyrrolidinone, 20-epi-1,25 dihydroxyvitamin D3, 22-oxacalcitriol, 2'-nor-cGMP, 3-isobutyl GABA, 5-ethynyluracil, 6-FUDCA, 7-methoxytacrine, Abamectin, abanoquil, abecarnil, abiraterone, Ablukast, Ablukast Sodium, Acadesine, acamprosate, Acarbose, Acebutolol, Acecainide Hydrochloride, Aceclidine, aceclofenac, Acedapsone, Aceglutamide Aluminum, Acemannan, Acetaminophen, Acetazolamide, Acetohexamide, Acetohydroxamic Acid, acetomepregenol, Acetophenazine Maleate, Acetosulfone Sodium, Acetylcholine Chloride, Acetylcysteine, acetyl-L-carnitine, acetylmethadol, Acifran, acipimox, acitemate, Acitretin, Acivicin, Aclarubicin, aclatonium, Acodazole Hydrochloride, aconiazide, Acrisorcin, Acrivastine, Acronize, Actisomide, Actodigin, Acyclovir, acylfulvene, adafenoxate, adapalene, Adapalene, adatanserin, Adatanserin Hydrochloride, adecypenol, adecypenol, Adefovir, adelmidrol, ademetionine, Adenosine, Adinazolam, Adiphenine Hydrochloride, adiposin, Adozelesin, adrafinil, Adrenalone, arbutamine, alacepril, Alamycin Alaproclate, alaptide, Albendazole, albolabrin, Albuterol, Albutoin, Alclofenac, Alclometasone Dipropionate, Alcloxa, aldecalmycin, Aldesleukin, Aldioxa, Alendronate Sodium, alendronic acid, alentemol, Alentemol Hydrobromide, Aletamine Hydrochloride, Aleuronium Chloride, Alexidine, alfacalcidol, Alfentanil Hydrochloride, alfuzosin, Algestone Acetonide, alglucerase, Aliflurane, alinastine, Alipamide, Allantoin, Allobarbital, Allopurinol, ALL-TK antagonists, Alonimid, alosetron, Alosetron Hydrochloride, Alovudine, Alpertan, Alpha Amylase, alpha idosone, Alpidem, Alprazolam, Alprenolol Hydrochloride, Alprenoxime Hydrochloride, Alprostadil, Alrestatin Sodium, Altanserin Tartrate, Alteplase, Althiazide, Altretamine, altromycin B, Alverine Citrate, Alvircept Sudotox, Amadinone Acetate, Amantadine Hydrochloride, ambamustine, Ambomycin, Ambruticin, Ambuphylline, Ambuside, Amcinafal, Amcinonide, Amdinocillin, Amdinocillin Pivoxil, Amedalin Hydrochloride, amelometasone, Ameltolide, Amesergide, Ametantrone Acetate, amezinium methylsulfate, amfebutamone, Amfenac Sodium, Amflutizole, Amicycline, Amidephrine Mesylate, amidox, Amifloxacin, amifostine, Amikacin, Amiloride Hydrochloride, Aminacrine Hydrochloride, Aminobenzoate Potassium, Aminobenzoate Sodium, Aminocaproic Acid, Aminoglutethimide, Aminohippurate Sodium, aminolevulinic acid, Aminophylline, A minorex, Aminosalicylate sodium, Aminosalicylic acid, Amiodarone, Amiprilose Hydrochloride, Amiquinsin Hydrochloride, amisulpride, Amitraz, Amitriptyline Hydrochloride, Amlexanox, amlodipine, Amobarbital Sodium, Amodiaquin, Amodiaquin Hydrochloride, Amorolfine, Amoxapine, Amoxicillin, Amphecloral, Amphetamine Sulfate, Amphomycin, Amphotericin B, Ampicillin, ampiroxicam, Ampyzine Sulfate, Amquinate, Amrinone, amrinone, amrubicin, Amsacrine, amylin, amythiamicin, Anagestone Acetate, anagrelide, Anakinra, ananain, anaritide, Anaritide Acetate, Anastrozole, Anazolene Sodium, Ancrod, andrographolide, Androstenedione, angiogenesis inhibitors, Angiotensin Amide, Anidoxime, Anileridine, Anilopam Hydrochloride, Aniracetam, Anirolac, Anisotropine Methylbromide, Anistreplase, Anitrazafen, anordrin, antagonist D, antagonist G, antarelix, Antazoline Phosphate, Anthelmycin, Anthralin, Anthramycin, antiandrogen, Acedapsone, Felbamate, antiestrogen, antineoplaston, Antipyrine, antisense oligonucleotides, apadoline, apafant, Apalcillin Sodium, apaxifylline, Apazone, aphidicolin glycinate, Apixifylline, Apomorphine Hydrochloride, apraclonidine, Apraclonidine Hydrochloride, Apramycin, Aprindine, Aprindine Hydrochloride, aprosulate sodium, Aprotinin, Aptazapine Maleate, aptiganel, apurinic acid, aranidipine, Aranotin, Arbaprostil, arbekacin, arbidol, Arbutamine Hydrochloride, Arclofenin, Ardeparin Sodium, argatroban, Arginine, Argipressin Tannate, Arildone, aripiprazole, arotinolol, Arprinocid, Arteflene, Artilide Fumarate, asimadoline, aspalatone, Asparaginase, Aspartic Acid, Aspartocin, asperfuran, Aspirin, aspoxicillin, Asprelin, Astemizole, Astromicin Sulfate, asulacrine, atamestane, Atenolol, atevirdine, Atipamezole, Atiprosin Maleate, Atolide, Atorvastatin Calcium, Atosiban, Atovaquone, atpenin B, Atracurium Besylate, atrimustine, atrinositol, Atropine, Auranofin, aureobasidin A, Aurothioglucose, Avilamycin, Avoparcin, Avridine, axinastatin 1, axinastatin 2, axinastatin 3, Azabon, Azacitidinie, Azaclorzine Hydrochloride, Azaconazole, azadirachtin, Azalanstat Dihydrochloride, Azaloxan Fumarate, Azanator Maleate, Azanidazole, Azaperone, Azaribine, Azaserine, azasetron, Azatadine Maleate, Azathioprine, Azathioprine Sodium, azatoxin, azatyrosine, azelaic acid, azelastine, azelnidipine, Azepindole, Azetepa, azimilide, Azithromycin, Azlocillin, Azolitmin, Azosemide, Azomycin Aztreonam, Azulene Sodium, Bacampicillin Hydrochloride, baccalin III, Bacitracin, Baclofen, bacoside A, bacoside B, bactobolamine, balanol, balazipone, balhimycin, balofloxacin, balsalazide, Bambermycins, bambuterol, Bamethan Sulfate, Bamifylline Hydrochloride, Bamidazole, baohuoside 1, Barmastine, barnidipine, Basifungin, Batanopride Hydrochloride, batebulast, Batelapine Maleate, Batimastat, beauvericin, Becanthone Hydrochloride, becaplermin, becliconazole, Beclomethasone Dipropionate, befloxatone, Benserazide, Belfosdil, Belladonna, Beloxamide, Bemesetron, Bemitradine, Bemoradan, Benapryzine Hydrochloride, Benazepril Hydrochloride, Benazeprilat, Bendacalol Mesylate, Bendazac, Bendroflumethiazide, benflumetol, benidipine, Benorterone, Benoxaprofen, Benoxaprofen, Benoxinate Hydrochloride, Benperidol, Bentazepam, Bentiromide, Benurestat, Benzbromarone, Benzethonium Chloride, Benzetimide Hydrochloride, Benzilonium Bromide, Benzindopyrine Hydrochloride, benzisoxazole, Benzocaine, benzochlorins, Benzoctamine Hydrochloride, Benzodepa, benzoidazoxan, Benzonatate, Benzoyl Peroxide, Benzoylpas Calcium, benzoylstaurosporine, Benzquinamide, Benzthiazide, benztropine, Benztropine Mesylate, Benzydamine Hydrochloride, Benzylpenicilloyl Polylysine, bepridil, Bepridil Hydrochloride, Beractant, Beraprost, Berefrine, berlafenone, bertosamil, Berythromycin, besipirdine, beta-alanine, betaclamycin B, Betamethasone, betamipron, betaxolol, Betaxolol Hydrochloride, Bethanechol Chloride, Bethanidine Sulfate, betulinic acid, bevantolol, Bevantolol Hydrochloride, Bezafibrate, bFGF inhibitor, Bialamicol Hydrochloride, Biapenem, Bicalutamide, Bicifadine Hydrochloride, Biclodil Hydrochloride, Bidisomide, bifemelane, Bifonazole, bimakalim, bimethyl, Bindarit, Biniramycin, binospirone, bioxalomycin alpha2, Bipenamol Hydrochloride, Biperiden, Biphenamine Hydrochloride, biriperone, bisantrene, bisaramil, bisaziridinylspermine, bis-benzimidazole A, bis-benzimidazole B, bisnafide, Bisobrin Lactate, Bisoprolol, Bispyrithione Magsulfex, bistramide D, bistramide K, bistratene A, Bithionolate Sodium, Bitolterol Mesylate, Bivalirudin, Bizelesin, Bleomycin Sulfate, Bolandiol Dipropionate, Bolasterone, Boldenone Undecylenate, boldine, Bolenol, Bolmantalate, bopindolol, Bosentan, Boxidine, brefeldin, breflate, Brequinar Sodium, Bretazenil, Bretylium Tosylate, Brifentanil Hydrochloride, brimonidine, Brinolase, Brocresine, Brocrinat, Brofoxine, Bromadiolone Maleate, Bromazepam, Bromchlorenone, Bromelains, bromfenac, Bromindione, Bromocriptine, Bromodiphenhydramine Hydrochloride, Bromoxamide, Bromperidol, Bromperidol Decanoate, Brompheniramine Maleate, Broperamole, Bropirimine, Brotizolam, Bucainide Maleate, bucindolol, Buclizine Hydrochloride, Bucromarone, Budesonide, budipine, budotitane, Buformin, Bumetanide, Bunaprolast, bunazosin, Bunolol Hydrochloride, Bupicomide, Bupivacaine Hydrochloride, Buprenorphine Hydrochloride, Bupropion Hydrochloride, Buramate, Buserelin Acetate, Buspirone Hydrochloride, Busulfan, Butabarbital, Butacetin, Butaclamol Hydrochloride, Butalbital, Butamben, Butamirate Citrate, Butaperazine, Butaprost, Butedronate Tetrasodium, butenafine, Buterazine, buthionine sulfoximine, Butikacin, Butilfenin, Butirosin Sulfate, Butixirate, butixocort propionate, Butoconazole Nitrate, Butonate, Butopamine, Butoprozine Hydrochloride, Butorphanol, Butoxamine Hydrochloride, Butriptyline Hydrochloride, Cactinomycin, Cadexomer Iodine, Caffeine, calanolide A, Calcifediol, Calcipotriene, calcipotriol, Calcitonin, Calcitriol, Calcium Undecylenate, calphostin C, Calusterone, Cambendazole, camonagrel, camptothecin derivatives, canarypox IL-2, candesartan, Candicidin, candoxatril, candoxatrilat, Caniglibose, Canrenoate Potassium, Canrenone, capecitabine, Capobenate Sodium, Capobenic Acid, Capreomycin Sulfate, capromab, capsaicin, Captopril, Capuride, Caracemide, Carbachol, Carbadox, Carbamazepine, Carbamide Peroxide, Carbantel Lauryl Sulfate, Carbaspirin Calcium, Carbazeran, carbazomycin C, Carbenicillin Potassium, Carbenoxolone Sodium, Carbetimer, carbetocin, Carbidopa, Carbidopa-Levodopa, Carbinoxamine Maleate, Carbiphene Hydrochloride, Carbocloral, Carbocysteine, Carbol-Fuchsin, Carboplatin, Carboprost, carbovir, carboxamide-aminotriazo-le, carboxyamidotriazole, carboxymethylated beta-1, 3-glucan, Carbuterol Hydrochloride, Carfentanil Citrate, Carisoprodol, Carmantadine, Carmustine, Camidazole, Caroxazone, carperitide, Carphenazine Maleate, Carprofen, Carsatrin Succinate, Cartazolate, carteolol, Carteolol Hydrochloride, cartilag derived inhibitor, Carubicin Hydrochloride, Carumonam Sodium, carvedilol, carvotroline, Carvotroline Hydrochloride, carzelesin, casein kinase inhibitors, castanospermine, carumonam, cebaracetam, cecropins, Cedefingol, Cefaclor, Cefadroxil, Cefamandole, Cefaparole, Cefatrizine, Cefazaflur Sodium, Cefazolin, Cefbuperazone, cefcapene pivoxil, cefdaloxime pentexil tosilate, Cefdinir, cefditoren pivoxil, Cefepime, cefetamet, Cefetecol, cefixime, cefluprenam, Cefinenoxime Hydrochloride, Cefmetazole, fminox, cefodizime, Cefonicid Sodium, Cefoperazone Sodium, Ceforanide, cefoselis, Cefotaxime Sodium, Cefotetan, cefotiam, Cefoxitin, cefozopran, cefpimizole, Cefpiramide, cefpirome, cefpodoxime proxetil, cefprozil, Cefroxadine, cefsulodin, Ceftazidime, cefteram, ceftibuten, Ceftizoxime Sodium, ceftriaxone, Cefuroxime, celastrol, celikalim, celiprolol, cepacidine A, Cephacetrile Sodium, Cephalexin, Cephaloglycin, Cephaloridine, Cephalothin Sodium, Cephapirin Sodium, Cephradine, cericlamine, cerivastatin, Ceronapril, certoparin sodium, Ceruletide, Cetabon Sodium, Cetalkonium Chloride, Cetamolol Hydrochloride, cetiedil, cetirizine, Cetophenicol, Cetraxate Hydrochloride, cetrorelix, Cetylpyridinium Chloride, Chenodiol, Chlophedianol Hydrochloride, Chloral Betaine, Chlorambucil, Chloramphenicol, Chlordantoin, Chlordiazepoxide, Chlorhexidine Gluconate, chlorine, Chlormadinone Acetate, chloroorienticin A, Chloroprocaine Hydrochloride, Chloropropamide, Chloroquine, chloroquinoxaline sulfonamide, Chlorothiazide, Chlorotrianisene, Chloroxine, Chloroxylenol, Chlorphenesin Carbamate, chlorpheniramine Maleate, Chlorpromazine, Chlorpropamide, Chlorprothixene, Chlortetracycline Bisulfate, Chlorthalidone, Chlorzoxazone, Cholestyramine Resin, Chromonar Hydrochloride, cibenzoline, cicaprost, Ciclafrine Hydrochloride, Ciclazindol, ciclesonide, cicletanine, Ciclopirox, Ciclopofen, cicloprolol, Cidofovir, Cidoxepin Hydrochloride, Cifenline, Ciglitazone, Ciladopa Hydrochloride, cilansetron, Cilastatin Sodium, Cilazapril, cilnidipine, Cilobamine Mesylate, cilobradine, Cilofungin, cilostazol, Cimaterol, Cimetidine, cimetropium bromide, Cinalukast, Cinanserin Hydrochloride, Cinepazet Maleate, Cinflumide, Cingestol, cinitapride, Cinnamedrine, Cinnarizine, cinolazepam, Cinoxacin, Cinperene, Cinromide, Cintazone, Cintriamide, Cioteronel, Cipamfylline, Ciprefadol Succinate, Ciprocinonide, Ciprofibrate, Ciprofloxacin, ciprostene, Ciramadol, Cirolemycin, cisapride, cisatracurium besylate, Cisconazole, Cisplatin, cis-porphyrin, cistinexine, citalopram, Citenamide, citicoline, citreamicin alpha, cladribine, Clamoxyquin Hydrochloride, Clarithromycin, clausenamide, Clavulanate Potassium, Clazolam, Clazolimine, clebopride, Clemastine, Clentiazem Maleate, Clidinium Bromide, clinafloxacin, Clindamycin, Clioquinol, Clioxanide, Ciprofen, clobazam, Clobetasol Propionate, Clobetasone Butyrate, Clocortolone Acetate, Clodanolene, Clodazon Hydrochloride, clodronic acid, Clofazimine, Clofibrate, Clofilium Phosphate, Clogestone Acetate, Clomacran Phosphate, Clomegestone Acetate, Clometherone, clomethiazole, clomifene analogues, Clominorex, Clomiphene, Clomipramine Hydrochloride, Clonazepam, Clonidine, Clonitrate, Clonixeril, Clonixin, Clopamide, Clopenthixol, Cloperidone Hydrochloride, clopidogrel, Clopimozide, Clopipazan Mesylate, Clopirac, Cloprednol, Cloprostenol Sodium, Clorazepate Dipotassium, Clorethate, Clorexolone, Cloroperone Hydrochloride, Clorprenaline Hydrochloride, Clorsulon, Clortermine Hydrochloride, Closantel, Closiramine Aceturate, Clothiapine, Clothixamide Maleate Cloticasone Propionate, Clotrimazole, Cloxacillin Benzathine, Cloxyquin, Clozapine, Cocaine, Coccidioidin, Codeine, Codoxime, Colchicine, colestimide, Colestipol Hydrochloride, Colestolone, Colforsin, Colfosceril Palmitate, Colistimethate Sodium, Colistin Sulfate, collismycin A, collismycin B, Colterol Mesylate, combretastatin A4, combretastatin analogue, complestatin, conagenin, Conorphone Hydrochloride, contignasterol, contortrostatin, Cormethasone Acetate, Corticorelin Ovine Triflutate, Corticotropin, Cortisone Acetate, Cortivazol, Cortodoxone, cosalane, costatolide, Cosyntropin, cotinine, Coumadin, Coumermycin, crambescidin 816, Crilvastatin, crisnatol, Cromitrile Sodium, Cromolyn Sodium, Crotamiton, cryptophycin 8, cucumariosid, Cuprimyxin, curacin A, curdlan sulfate, curiosin, Cyclacillin, Cyclazocine, cyclazocin, cyclic HPMPC, Cyclindole, Cycliramine Maleate, Cyclizine, Cyclobendazole, cyclobenzaprine, cyclobut A, cyclobut G, cyclocapron, Cycloguanil Pamoate, Cycloheximide, cyclopentanthraquinones, Cyclopenthiazide, Cyclopentolate Hydrochloride, Cyclophenazine Hydrochloride, Cyclophosphamide, cycloplatin, Cyclopropane, Cycloserine, cycloson, Cyclosporin, cyclothialidine, Cyclothiazide, cyclothiazomycin, Cyheptamide, cypemycin, Cypenamine Hydrochloride, Cyprazepam, Cyproheptadine Hydrochloride, Cyprolidol Hydrochloride, cyproterone, Cyproximide, Cysteamine, Cysteine Hydrochloride, Cystine, Cytarabine, Cytarabine Hydrochloride, cytarabine Ocfosfate, cytochalasin B, cytolytic factor, cytostatin, Dacarbazine, dacliximab, dactimicin, Dactinomycin, daidzein, Daledalin Tosylate, dalfopristin, Dalteparin Sodium, Daltroban, Dalvastatin, danaparoid, Danazol, Dantrolene, daphlnodorin A, dapipramide, dapitant, Dapoxetine Hydrochloride, Dapsone, Daptomycin, Darglitazone Sodium, darifenacin, darlucin A, Darodipine, darsidomine, Daunorubicin Hydrochloride, Dazadrol Maleate, Dazepinil Hydrochloride, Dazmegrel, Dazopride Fumarate, Dazoxiben Hydrochloride, Debrisoquin Sulfate, Decitabine, deferiprone, deflazacort, Dehydrocholic Acid, dehydrodidemnin B, Dehydroepiandrosterone, delapril, Delapril Hydrochloride, Delavirdine Mesylate, delequamine, delfaprazine, Delmadinone Acetate, delmopinol, delphinidin, Demecarium Bromide, Demeclocycline, Demecycline, Demoxepam, Denofungin, deoxypyridinoline, Depakote, deprodone, Deprostil, depsidomycin, deramciclane, dermatan sulfate, Desciclovir, Descinolone Acetonide, Desflurane, Desipramine Hydrochloride, desirudin, Deslanoside, deslorelin, desmopressin, desogestrel, Desonide, Desoximetasone, desoxoamiodarone, Desoxycorticosterone Acetate, detajmium bitartrate, Deterenol Hydrochloride, Detirelix Acetate, Devazepide, Dexamethasone, Dexamisole, Dexbrompheniramine Maleate, Dexchlorpheniramine Maleate, Dexclamol Hydrochloride, Dexetimide, Dexfenfluramine Hydrochloride, dexifosfamide, Deximafen, Dexivacaine, dexketoprofen, dexloxiglumide, Dexmedetomidine, Dexormaplatin, Dexoxadrol Hydrochloride, Dexpanthenol, Dexpemedolac, Dexpropranolol Hydrochloride, Dexrazoxane, dexsotalol, dextrin 2-sulphate, Dextroamphetamine, Dextromethorphan, Dextrorphan Hydrochloride, Dextrothyroxine Sodium, dexverapamil, Dezaguanine, dezinamide, dezocine, Diacetolol Hydrochloride, Diamocaine Cyclamate, Diapamide, Diatrizoate Meglumine, Diatrizoic Acid, Diaveridine, Diazepam, Diaziquone, Diazoxide, Dibenzepin Hydrochloride, Dibenzothiophene, Dibucaine, Dichlorvos, Dichloralphenazone, Dichlorphenamide, Dicirenone, Diclofenac Sodium, Dicloxacillin, dicranin, Dicumarol, Dicyclomine Hydrochloride, Didanosine, didemnin B, didoc, Dienestrol, dienogest, Diethylcarbamazine Citrate, diethylhomospermine, diethylnorspermine, Diethylpropion Hydrochloride, Diethylstilbestrol, Difenoximide Hydrochloride, Difenoxin, Diflorasone Diacetate, Difloxacin Hydrochloride, Difluanine Hydrochloride, Diflucortolone, Diflumidone Sodium, Diflunisal, Difluprednate, Diftalone, Digitalis, Digitoxin, Digoxin, Dihexyverine Hydrochloride, dihydrexidine, dihydro-5-azacytidine, Dihydrocodeine Bitartrate, Dihydroergotamine Mesylate, Dihydroestosterone, Dihydrostreptomycin Sulfate, Dihydrotachysterol, dihydrotaxol, Dilantin, Dilevalol Hydrochloride, Diltiazem Hydrochloride, Dimefadane, Dimefline Hydrochloride, Dimenhydrinate, Dimercaprol, Dimethadione, Dimethindene Maleate, Dimethisterone, dimethyl prostaglandin Al, Dimethyl Sulfoxide, dimethylhomospermine, dimiracetam, Dimoxamine Hydrochloride, Dinoprost, Dinoprostone, Dioxadrol Hydrochloride, dioxamycin, Diphenhydramine Citrate, Diphenidol, Diphenoxylate Hydrochloride, diphenyl spiromustine, Dipivefrin Hydrochloride, Dipivefrin, dipliencyprone, diprafenone, dipropylnorspermine, Dipyridamole, Dipyrithione, Dipyrone, dirithromycin, discodermolide, Disobutamide, Disofenin, Disopyramide, Disoxaril, disulfiram, Ditekiren, Divalproex Sodium, Dizocilpine Maleate, Dobutamine, docarpamine, Docebenone, Docetaxel, Doconazole, docosanol, dofetilide, dolasetron, Ebastine, ebiratide, ebrotidine, ebselen, ecabapide, ecabet, ecadotril, ecdysterone, echicetin, echistatin, Echothiophate Iodide, Eclanamine Maleate, Eclazolast, ecomustine, Econazole, ecteinascidin 722, edaravone, Edatrexate, edelfosine, Edifolone Acetate, edobacomab, Edoxudine, edrecolomab, Edrophonium Chloride, edroxyprogesteone Acetate, efegatran, eflornithine, efonidipine, egualcen, Elantrine, eleatonin, elemene, eletriptan, elgodipine, eliprodil, Elsamitrucin, eltenac, Elucaine, emalkalim, emedastine, Emetine Hydrochloride, emiglitate, Emilium Tosylate, emitefur, emoctakin, Enadoline Hydrochloride, enalapril, Enalaprilat, Enalkiren, enazadrem, Encyprate, Endralazine Mesylate, Endrysone, Enflurane, englitazone, Enilconazole, Enisoprost, Enlimomab, Enloplatin, Enofelast, Enolicam Sodium, Enoxacin, enoxacin, enoxaparin sodium, Enoxaparin Sodium, Enoximone, Enpiroline Phosphate, Enprofylline, Enpromate, entacapone, enterostatin, Enviradene, Enviroxime, Ephedrine, Epicillin, Epimestrol, Epinephrine, Epinephryl Borate, Epipropidine, Epirizole, epirubicin, Epitetracycline Hydrochloride, Epithiazide, Epoetin Alfa, Epoetin Beta, Epoprostenol, Epoprostenol Sodium, epoxymexrenone, epristeride, Eprosartan, eptastigmine, equilenin, Equilin, Erbulozole, erdosteine, Ergoloid Mesylates, Ergonovine Maleate, Ergotamine Tartrate, ersentilide, Ersofermin, erythritol, Erythrityl Tetranitrate, Erythromycin, Esmolol Hydrochloride, Esorubicin Hydrochloride, Esproquin Hydrochloride, Estazolam, Estradiol, Estramustine, estramustine analogue, Estrazinol Hydrobromide, Estriol, Estrofurate, estrogen agonists, estrogen antagonists, Estrogens, Conjugated Estrogens, Esterified Estrone, Estropipate, esuprone, Etafedrine Hydrochloride, Etanidazole, etanterol, Etarotene, Etazolate Hydrochloride, Eterobarb, ethacizin, Ethacrynate Sodium, Ethacrynic Acid, Ethambutol Hydrochloride, Ethamivan, Ethanolamine Oleate, Ethehlorvynol, Ether, Ethinyl estradiol, Ethiodized Oil, Ethionamide, Ethonam Nitrate, Ethopropazine Hydrochloride, Ethosuximide, Ethotoin, Ethoxazene Hydrochloride, Ethybenztropine, Ethyl Chloride, Ethyl Dibunate, Ethylestrenol, Ethynodiol, Ethynerone, Ethynodiol Diacetate, Etibendazole, Etidocaine, Etidronate Disodium, Etidronic Acid, Etifenin, Etintidine Hydrochloride, etizolam, Etodolac, Etofenamate, Etoformin Hydrochloride, Etomidate, Etonogestrel, Etoperidone Hydrochloride, Etoposide, Etoprine, Etoxadrol Hydrochloride, Etozolin, etrabamine, Etretinate, Etryptamine Acetate, Eucatropine Hydrochloride, Eugenol, Euprotin Hydrochloride, eveminomicin, Exametazime, examolin, Exaprolol Hydrochloride, exemestane, fadrozole, faeriefungin, Famciclovir, Famotidine, Fampridine, fantofarone, Fantridone Hydrochloride, faropenem, fasidotril, fasudil, fazarabine, fedotozine, felbamate, Felbinac, Felodipine, Felypressin, Fenalamide, Fenarole, Fenbendazole, Fenbufen, Fencibutirol, Fenclofenac, Fenclonine, Fenclor, Fendosal, Fenestrel, Fenethylline Hydrochloride, Fenfluramine Hydrochloride, Fengabine, Fenimide, Fenisorex, Fenmetozole Hydrochloride, Fenmetramide, Fenobam, Fenoctimine Sulfate, fenofibrate, fenoldopam, Fenoprofen, Fenoterol, Fenpipalone, Fenprinast Hydrochloride, Fenprostalene, Fenquizone, fenretinide, fenspiride, Fentanyl Citrate, Fentiazac, Fenticlor, fenticonazole, Fenyripol Hydrochloride, fepradinol, ferpifosate sodium, ferristene, ferrixan, Ferrous Sulfate, Dried, Ferumoxides, ferumoxsil, Fetoxylate Hydrochloride, fexofenadine, Fezolamine Fumarate, Fiacitabine, Fialuridine, Fibrinogen/125, filgrastim, Filipin, finasteride, Flavodilol Maleate, flavopiridol, Flavoxate Hydrochloride, Flazalone, flecainide, flerobuterol, Fleroxacin, flesinoxan, Flestolol Sulfate, Fletazepam, flezelastine, flobufen, Floctafenine, flomoxef, Flordipine, florfenicol, florifenine, flosatidil, Flosequinan, Floxacillin, Floxuridine, fluasterone, Fluazacort, Flubanilate Hydrochloride, Flubendazole, Flucindole, Flucloronide, Fluconazole, Flucytosine, Fludalanine, Fludarabine Phosphate, Fludazonium Chloride, Fludeoxyglucose F 18, Fludorex, Fludrocortisone Acetate, Flufenamic Acid, Flufenisal, Flumazenil, flumecinol, Flumequine, Flumeridone, Flumethasone, Flumetramide, Flumezapine, Fluminorex, Flumizole, Flumoxonide, flunarizine, Flunidazole, Flunisolide, Flunitrazepam, Flunixin, fluocalcitriol, Fluocinolone Acetonide, Fluocinonide, Fluocortin Butyl, Fluocortolone, Fluorescein, fluorodaunorunicin hydrochloride, Fluorodopa F 18, Fluorometholone, Fluorouracil, Fluotracer Hydrochloride, Fluoxetine, Fluoxymesterone, fluparoxan, Fluperamide, Fluperolone Acetate, Fluphenazine Decanoate, flupirtine, Fluprednisolone, Fluproquazone, Fluprostenol Sodium, Fluquazone, Fluradoline Hydrochloride, Flurandrenolide, Flurazepam Hydrochloride, Flurbiprofen, Fluretofen, flurithromycin, Flurocitabine, Flurofamide, Flurogestone Acetate, Flurothyl, Fluroxene, Fluspiperone, Fluspirilene, Fluticasone Propionate, flutrimazole, Flutroline, fluvastatin, Fluvastatin Sodium, fluvoxamine, Fluzinamide, Folic Acid, Follicle regulatory protein, Folliculostatin, Fomepizole, Fonazine Mesylate, forasartan, forfenimex, forfenirmex, formestane, Formocortal, formoterol, Fosarilate, Fosazepam, Foscarnet Sodium, fosfomycin, Fosfonet Sodium, fosinopril, Fosinoprilat, fosphenytoin, Fosquidone, Fostedil, fostriecin, fotemustine, Fuchsin, Basic, Fumoxicillin, Fungimycin, Furaprofen, Furazolidone, Furazolium Chloride, Furegrelate Sodium, Furobufen, Furodazole, Furosemide, Fusidate Sodium, Fusidic Acid, gabapentin, Gadobenate Dimeglumine, gadobenic acid, gadobutrol, Gadodiamide, gadolinium texaphyrin, Gadopentetate Dimegiumine, gadoteric acid, Gadoteridol, Gadoversetamide, galantamine, galdansetron, Galdansetron Hydrochloride, Gallamine Triethiodide, gallium nitrate, gallopamil, galocitabine, Gamfexine, gamolenic acid, Ganciclovir, ganirelix, gelatinase inhibitors, Gemcadiol, Gemcitabine, Gemeprost, Gemfibrozil, Gentamicin Sulfate, Gentian Violet, gepirone, Gestaclone, Gestodene, Gestonorone Caproate, Gestrinone, Gevotroline Hydrochloride, girisopam, glaspimod, glaucocalyxin A, Glemanserin, Gliamilide, Glibornuride, Glicetanile Sodium, Gliflumide, Glimepiride, Glipizide, Gloximonam, Glucagon, glutapyrone, glutathione inhibitors, Glutethimide, Glyburide, glycophene, glycopril, Glycopyrrolate, Glyhexamide, Glymidine Sodium, Glyoctamide, Glyparamide, Gold Au 198, Gonadoctrinins, Gonadorelin, Gonadotropins, Goserelin, Gramicidin, Granisetron, grepafloxacin, Griseofulvin, Guaiapate, Guaithylline, Guanabenz, Guanabenz Acetate, Guanadrel Sulfate, Guancydine, Guanethidine Monosulfate, Guanfacine Hydrochloride, Guanisoquin Sulfate, Guanoclor Sulfate, Guanoctine Hydrochloride, Guanoxabenz, Guanoxan Sulfate, Guanoxyfen Sulfate, Gusperimus Trihydrochloride, Halazepam, Halcinonide, halichondrin B, Halobetasol Propionate, halofantrine, Halofantrine Hydrochloride, Halofenate, Halofuginone Hydrobromide, halomonth, Halopemide, Haloperidol, halopredone, Haloprogesterone, Haloprogin, Halothane, Halquinols, Hamycin, Han memopausal gonadotropins, hatomamicin, hatomarubigin A, hatomarubigin B, hatomarubigin C, hatomarubigin D, Heparin Sodium, hepsulfam, heregulin, Hetacillin, Heteronium Bromide, Hexachlorophene:Hydrogen Peroxide, Hexafluorenium Bromide, hexamethylene bisacetamide, Hexedine, Hexobendine, Hexoprenaline Sulfate, Hexylresorcinol, Histamine Phosphate, Histidine, Histoplasmin, Histrelin, Homatropine Hydrobromide, Hoquizil Hydrochloride, Human chorionic gonadotropin, Hycanthone, Hydralazine Hydrochloride, Hydralazine Polistirex, Hydrochlorothiazide, Hydrocodone Bitartrate, Hydrocortisone, Hydroflumethiazide, Hydromorphone Hydrochloride, Hydroxyamphetamine Hydrobromide, Hydroxychloroquine Sulfate, Hydroxyphenamate, Hydroxyprogesterone Caproate, Hydroxyurea, Hydroxyzine Hydrochloride, Hymecromone, Hyoscyamine, hypericin, Ibafloxacin, ibandronic acid, ibogaine, Ibopamine, ibudilast, Ibufenac, Ibuprofen, Ibutilide Fumarate, Icatibant Acetate, Ichthammol, Icotidine, idarubicin, idoxifene, Idoxuridine, idramantone, Iomefloxacin, Iesopitron, Ifetroban, Ifosfamide, Ilepeimide, ilimaquinone, ilmofosine, ilomastat, Ilonidap, iloperidone, iloprost, Imafen Hydrochloride, Imazodan Hydrochloride, imidapril, imidazenil, imidazoacridones, Imidecyl Iodine, Imidocarb Hydrochloride, Imidoline Hydrochloride, Imidurea, Imiloxan Hydrochloride, Imipenem, Imipramine Hydrochloride, imiquimod, immunostimulant peptides, Impromidine Hydrochloride, Indacrinone, Indapamide, Indecainide Hydrochloride, Indeloxazine Hydrochloride, Indigotindisulfonate Sodium, indinavir, Indocyanine Green, Indolapril Hydrochloride, Indolidan, indometacin, Indomethacin Sodium, Indoprofen, indoramin, Indorenate Hydrochloride, Indoxole, Indriline Hydrochloride, inocoterone, inogatran, inolimomab, Inositol Niacinate, Insulin, interferons, interleukins, Intrazone, Intriptyline Hydrochloride, iobenguane, Iobenzamic Acid, iobitridol, Iocarmate Meglumine, Iocarmic Acid, Iocetamic Acid, Iodamide, Iodine, Iodipamide Meglumine, Iodixanol, iodoamiloride, Iodoantipyrine I 131, Iodocholesterol I 131, iododoxorubicin, Iodohippurate Sodium I 131, Iodopyracet I 125, Iodoquinol, Iodoxamate Meglumine, Iodoxamic Acid, Ioglicic Acid, Iofetamine Hydrochloride I 123, iofratol, Ioglucol, Ioglucomide, Ioglycamic Acid, Iogulamide, Iohexol, iomeprol, Iomethin I Iopronic Acid, iopromide, Iopronic Acid, Iopydol, Iopydone, iopydol, Iosefamic Acid, Ioseric Acid, Iosulamide Meglumine, Iosumetic Acid, Iotasul, Iotetric Acid, Iothalamate Sodium, Iothalamic Acid, iotriside, Iotrolan, Iotroxic Acid, Iotyrosine 1 131, Ioversol, Ioxagiate Sodium, Ioxaglate Meglumine, Ioxaglic Acid, ioxilan, Ioxotrizoic Acid, ipazilide, ipenoxazone, ipidacrine, Ipodate Calcium, ipomeanol, 4-, Ipratropium Bromide, ipriflavone, Iprindole, Iprofenin, Ipronidazole, Iproplatin, Iproxamine Hydrochloride, ipsapirone, irbesartan, irinotecan, irloxacin, iroplact, irsogladine, Irtemazole, isalsteine, Isamoxole, isbogrel, Isepamicin, isobengazole, Isobutamben, Isocarboxazid, Isoconazole, Isoetharine, isofloxythepin, Isoflupredone Acetate, Isoflurane, Isoflurophate, isohomohalicondrin B, Isoleucine, Isomazole Hydrochloride, Isomylamine Hydrochloride, Isoniazid, Isopropamide Iodide, Isopropyl Alcohol, isopropyl unoprostone, Isoproterenol Hydrochloride, Isosorbide, Isosorbide Mononitrate, Isotiquimide, Isotretinoin, Isoxepac, Isoxicam, Isoxsuprine Hydrochloride, isradipine, itameline, itasetron, Itazigrel, itopride, Itraconazole, Ivermectin, jasplakinolide, Josamycin, kahalalide F, Kalafungin, Kanamycin Sulfate, Ketamine Hydrochloride, Ketanserin, Ketazocine, Ketazolam, Kethoxal, Ketipramine Fumarate, Ketoconazole, Ketoprofen, Ketorfanol, ketorolac, Ketotifen Fumarate, Kitasamycin, Labetalol Hydrochloride, Lacidipine, lacidipine, lactitol, lactivicin, laennec, lafutidine, lamellarin-N triacetate, lamifiban, Lamivudine, Lamotrigine, lanoconazole, Lanoxin, lanperisone, lanreotide, Lansoprazole, latanoprost, lateritin, laurocapram, Lauryl Isoquinolinium Bromide, Lavoltidine Succinate, lazabemide, Lecimibide, lenamycin, lemildipine, leminoprazole, lenercept, Leniquinsin, lenograstim, Lenperone, lentinan sulfate, leptin, leptolstatin, lercanidipine, Lergotrile, lerisetron, Letimide Hydrochloride, letrazuril, letrozole, Leucine, leucomycin, Leuprolide Acetate, leuprolide+estrogen+progesterone, leuprorelin, Levamfetamine Succinate, levamisole, Levdobutamine Lactobionate, Leveromakalim, levetiracetam, Levocycloserine, levobetaxolol, levobunolol, levobupivacaine, levocabastine, levocarnitine, Levodopa, levodropropizine, levofloxacin, Levofuraltadone, Levoleucovorin Calcium, Levomethadyl Acetate, Levomethadyl Acetate Hydrochloride, levomoprolol, Levonantradol Hydrochloride, Levonordefrin, Levonorgestrel, Levopropoxyphene Napsylate, Levopropylcillin Potassium, levormeloxifene, Levorphanol Tartrate, levosimendan, levosulpiride, Levothyroxine Sodium, Levoxadrol Hydrochloride, Lexipafant, Lexithromycin, liarozole, Libenzapril, Lidamidine Hydrochloride, Lidocaine, Lidofenin, Lidoflazine, Lifarizine, Lifibrate, Lifibrol, Linarotene, Lincomycin, linear polyamine analogue, Linogliride, Linopirdine, linotroban, linsidomine, lintitript, lintopride, Liothyronine I 125, liothyronine sodium, Liotrix, lirexapride, lisinopril, lissoclinamide 7, Lixazinone Sulfate, lobaplatin, Lobenzarit Sodium, Lobucavir, Lodelaben, Lodoxamide, Lofemizole Hydrochloride, Lofentanil Oxalate, Lofepramine Hydrochloride, Lofexidine Hydrochloride, lombricine, Lomefloxacin, lomerizine, Lometraline Hydrochloride, lometrexol, Lomofungin, Lomoxicam, Lomustine, Lonapalene, lonazolac, lonidamine, Loperamide Hydrochloride, loracarbef, Lorajmine Hydrochloride, loratadine, Lorazepam, Lorbamate, Lorcainide Hydrochloride, Loreclezole, Loreinadol, lorglumide, Lormetazepam, Lornoxicam, lornoxicam, Lortalamine, Lorzafone, losartan, losigamone, losoxantrone, Losulazine Hydrochloride, loteprednol, lovastatin, loviride, Loxapine, Loxoribine, lubeluzole, Lucanthone Hydrochloride, Lufironil, Lurosetron Mesylate, lurtotecan, luteinizing hormone, lutetium, Lutrelin Acetate, luzindole, Lyapolate Sodium, Lycetamine, lydicamycin, Lydimycin, Lynestrenol, Lypressin, Lysine, lysofylline, lysostaphin, lytic peptides, Maduramicin, Mafenide, magainin 2 amide, Magnesium Salicylate, Magnesium Sulfate, magnolol, maitansine, Malethamer, mallotochromene, mallotojaponin, Malotilate, malotilate, mangafodipir, manidipine, maniwamycin A, Mannitol, mannostatin A, manumycin E, manumycin F, mapinastine, Maprotiline, marimastat, Martek 8708, Martek 92211, Masoprocol, maspin, massetolide, matrilysin inhibitors, Maytansine, Mazapertine Succiniate, Mazindol, Mebendazole, Mebeverine Hydrochloride, Mebrofenin, Mebutamate, Mecamylamine Hydrochloride, Mechlorethamine Hydrochloride, Meclocycline, Meclofenamate Sodium, Mecloqualone, Meclorisone Dibutyrate, Medazepam Hydrochloride, Medorinone, Medrogestone, Medroxalol, Medroxyprogesterone, Medrysone, Meclizine Hydrochloride, Mefenamic Acid, Mefenidil, Mefenorex Hydrochloride, Mefexamide, Mefloquine Hydrochloride, Mefruside, Megalocin Potassium Phosphate, Megestrol Acetate, Meglumine, Meglutol, Melengestrol Acetate, Melitracen Hydrochloride, Melphalan, Memotine Hydrochloride, Menabitan Hydrochloride, Menoctone, menogaril, Menotropins, Meobentine Sulfate, Mepartricin, Mepenzolate Bromide, Meperidine Hydrochloride, Mephentermine Sulfate, Mephenyloin, Mephobarbital, Mepivacaine Hydrochloride, Meprobamate, Meptazinol Hydrochloride, Mequidox, Meralein Sodium, merbarone, Mercaptopurine, Mercufenol Chloride, Mercury, Ammoniated, Merisoprol Hg 197, Meropenem, Mesalamine, Meseclazone, Mesoridazine, Mesterolone, Mestranol, Mesuprine Hydrochloride, Metalon Hydrochloride, Metaproterenol Polistirex, Metaraminol Bitartrate, Metaxalone, Meteneprost, meterelin, Metformin, Methacholine Chloride, Methacycline, Methadone Hydrochloride, Methadyl Acetate, Methalthiazide, Methamphetamine Hydrochloride, Methaqualone, Methazolamide, Methdilazine, Methenamine, Methenolone Acetate, Methetoin, Methicillin Sodium, Methimazole, methioninase, Methionine, Methisazone, Methixene Hydrochloride, Methocarbamol, Methohexital Sodium, Methopholine, Methotrexate, Methotrimeprazine, methoxadone, Methoxyflurane, Methsuximide, Methyclothiazide, Methyl 10 Palmoxirate, Methylatropine Nitrate, Methylbenzethonium Chloride, Methyldopa, Methyldopate Hydrochloride, Methylene Blue, Methylergonovine Maleate, methylhistamine, R-alpha, methylinosine monophosphate, Methylphenidate Hydrochloride, Methylprednisolone, Methyltestosterone, Ethynodiol Diacetate, Methysergide, Methysergide Maleate, Metiamide, Metiapine, Metioprim, metipamide, Metipranolol, Metizoline Hydrochloride, Metkephamid Acetate, metoclopramide, Metocurine Iodide, Metogest, Metolazone, Metopimazine, Metoprin, Metoprolol, Metoquinone, metrifonate, Metrizamide, Metrizoate Sodium, Metronidazole, Meturedepa, Metyrapone, Metyrosine, Mexiletine Hydrochloride, Mexrenoate Potassium, Mezlocillin, amfonelic Acid, Mianserin Hydrochloride, mibefradil, Mibefradil Dihydrochloride, Mibolerone, michellamine B, Miconazole, microcolin A, Midaflur, Midazolam Hydrochloride, midodrine, mifepristone, Mifobate, miglitol, milacemide, milameline, mildronate, Milenperone, Milipertine, milnacipran, Milrinone, miltefosine, Mimbane Hydrochloride, minaprine, Minaxolone, Minocromil, Minocycline, Minoxidil, Mioflazine Hydrochloride, miokamycin, mipragoside, mirfentanil, mirimostim, Mirincamycin Hydrochloride, Mirisetron Maleate, Mirtazapine, mismatched double stranded RNA, Misonidazole, Misoprostol, Mitindomide, Mitocarcin, Mitocromin, Mitogillin, mitoguazone, mitolactol, Mitomalcin, Mitomycin, mitonafide, Mitosper, Mitotane, mitoxantrone, mivacurium chloride, mivazerol, mixanpril, Mixidine, mizolastine, mizoribine, Moclobemide, modafinil, Modalina Sulfate, Modecainide, moexipril, mofarotene, Mofegiline Hydrochloride, mofezolac, molgramostim, Molinazone, Molindone Hydrochloride, Molsidomine, mometasone, Monatepil Maleate, Monensin, Monoctanoin, Montelukast Sodium, montirelin, mopidamol, moracizine, Morantel Tartrate, Moricizine, Morniflumate, Morphine Sulfate, Morrhuate Sodium, mosapramine, mosapride, motilide, Motretinide, Moxalactam Disodium, Moxazocine, moxiraprine, Moxnidazole, moxonidine, Mumps Skin Test Antigen, mustard anticancer agent, Muzolimine, mycaperoxide B, Mycophenolic Acid, myriaporone, Nabazenil, Nabilone, Nabitan Hydrochloride, Naboctate Hydrochloride, Nabumetone, N-acetyldinaline, Nadide, nadifloxacin, Nadolol, nadroparin calcium, nafadotride, nafamostat, nafarelin, Nafcillin Sodium, Nafenopin, Nafimidone Hydrochloride, Naflocort, Nafomine Maleate, Nafoxidine Hydrochloride, Nafronyl Oxalate, Naftifine Hydrochloride, naftopidil, naglivan, nagrestip, Nalbuphine Hydrochloride, Nalidixate Sodium, Nalidixic Acid, nalmefene, Nalmexone Hydrochloride, naloxone+pentazocine, Naltrexone, Namoxyrate, Nandrolone Phenpropionate, Nantradol Hydrochloride, Napactadine Hydrochloride, napadisilate, Napamezole Hydrochloride, napavin, Naphazoline Hydrochloride, naphterpin, Naproxen, Naproxol, napsagatran, Naranol Hydrochloride, Narasin, naratriptan, nartograstim, nasaruplase, Natamycin, nateplase, Naxagolide Hydrochloride, Nebivolol, Nebramycin, nedaplatin, Nedocromil, Nefazodone Hydrochloride, Neflumozide Hydrochloride, Nefopam Hydrochloride, Nelezaprine Maleate, Nemazoline Hydrochloride, nemorubicin, Neomycin Palmitate, Neostigmine Bromide, neridronic acid, Netilmicin Sulfate, neutral endopeptidase, Neutramycin, Nevirapine, Nexeridine Hydrochloride, Niacin, Nibroxane, Nicardipine Hydrochloride, Nicergoline, Niclosamide, Nicorandil, Nicotinyl Alcohol, Nifedipine, Nifirmerone, Nifluridide, Nifuradene, Nifuraldezone, Nifuratel, Nifuratrone, Nifurdazil, Nifurimide, Nifurpirinol, Nifurquinazol, Nifurthiazole, nilutamide, Nilvadipine, Nimazone, Nimodipine, niperotidine, niravoline, Niridazole, nisamycin, Nisbuterol Mesylate, nisin, Nisobamate, Nisoldipine, Nisoxetine, Nisterime Acetate, Nitarsone, nitazoxanide, nitecapone, Nitrafudam Hydrochloride, Nitralamine Hydrochloride, Nitramisole Hydrochloride, Nitrazepam, Nitrendipine, Nitrocycline, Nitrodan, Nitrofurantoin, Nitrofurazone, Nitroglycerin, Nitromersol, Nitromide, Nitromifene Citrate, Nitrous Oxide, nitroxide antioxidant, nitrullyn, Nivazol, Nivimedone Sodium, Nizatidine, Noberastine, Nocodazole, Nogalamycin, Nolinium Bromide, Nomifensine Maleate, Noracymethadol Hydrochloride, Norbolethone, Norepinephrine Bitartrate, Norethindrone, Norethynodrel, Norfloxacin, Norflurane, Norgestimate, Norgestomet, Norgestrel, Nortriptyline Hydrochloride, Noscapine, Novobiocin Sodium, N-substituted benzaimides, Nufenoxole, Nylestriol, Nystatin, O6-benzylguanine, Obidoxime Chloride, Ocaperidone, Ocfentanil Hydrochloride, Ocinaplon, Octanoic Acid, Octazamide, Octenidine Hydrochloride, Octodrine, Octreotide, Octriptyline Phosphate, Ofloxacin, Oformine, okicenone, Olanzapine, oligonucleotides, olopatadine, olprinone, olsalazine, Olsalazine Sodium, Olvanil, omeprazole, onapristone, ondansetron, Ontazolast, Oocyte maturation inhibitor, Opipramol Hydrochloride, oracin, Orconazole Nitrate, Orgotein, Orlislat, Ormaplatin, Ormetoprim, Ornidazole, Orpanoxin, Orphenadrine Citrate, osaterone, otenzepad, Oxacillin Sodium, Oxagrelate, oxaliplatin, Oxamarin Hydrochloride, oxamisole, Oxamniquine, oxandrolone, Oxantel Pamoate, Oxaprotiline Hydrochloride, Oxaprozin, Oxarbazole, Oxatomide, oxaunomycin, Oxazepam, oxcarbazepine, Oxendolone, Oxethazaine, Oxetorone Fumarate, Oxfendazole, Oxfenicine, Oxibendazole, oxiconazole, Oxidopamine, Oxidronic Acid, Oxifungin Hydrochloride, Oxilorphan, Oximonam, Oximonam Sodium, Oxiperomide, oxiracetam, Oxiramide, Oxisuran, Oxmetidine Hydrochloride, oxodipine, Oxogestone Phenpropionate, Oxolinic Acid, Oxprenolol Hydrochloride, Oxtriphylline, Oxybutynin Chloride, Oxychlorosene, Oxycodone, Oxymetazoline Hydrochloride, Oxymetholone, Oxymorphone Hydrochloride, Oxypertine, Oxyphenbutazone, Oxypurinol, Oxytetracycline, Oxytocin, ozagrel, Ozolinone, Paclitaxel, palauamine, Paldimycin, palinavir, palmitoylrhizoxin, Palmoxirate Sodium, pamaqueside, Pamatolol Sulfate, pamicogrel, Pamidronate Disodium, pamidronic acid, Panadiplon, panamesine, panaxytriol, Pancopride, Pancuronium Bromide, panipenem, pannorin, panomifene, pantethine, pantoprazole, Papaverine Hydrochloride, parabactin, Parachlorophenol, Paraldehyde, Paramethasone Acetate, Paranyline Hydrochloride, Parapenzolate Bromide, Pararosaniline Pamoate, Parbendazole, Parconazole Hydrochloride, Paregorico, Pareptide Sulfate, Pargyline Hydrochloride, parnaparin sodium, Paromomycin Sulfate, Paroxetine, parthenolide, Partricin, Paucimycin, pazelliptine, Pazinaclone, Pazoxide, pazufloxacin, pefloxacin, pegaspargase, Pegorgotein, Pelanserin Hydrochloride, peldesine, Peliomycin, Pelretin, Pelrinone Hydrochloride, Pemedolac, Pemerid Nitrate, pemirolast, Pemoline, Penamecillin, Penbutolol Sulfate, Penciclovir, Penfluridol, Penicillin G Benzathine, Penicillin G Potassium, Penicillin G Procaine, Penicillin G Sodium, Penicillin V, Penicillin V Benzathine, Penicillin V Hydrabamine, Penicillin V Potassium, Pentabamate, Pentaerythritol Tetranitrate, pentafuside, pentamidine, pentamorphone, Pentamustine, Pentapiperium Methylsulfate, Pentazocine, Pentetic Acid, Pentiapine Maleate, pentigetide, Pentisomicin, Pentizidone Sodium, Pentobarbital, Pentomone, Pentopril, pentosan, pentostatin, Pentoxifylline, Pentrinitrol, pentrozole, Peplomycin Sulfate, Pepstatin, perflubron, perfosfamide, Perfosfamide, pergolide, Perhexiline Maleate, perillyl alcohol, Perindopril, perindoprilat, Perlapine, Permethrin, perospirone, Perphenazine, Phenacemide, phenaridine, phenazinomycin, Phenazopyridine Hydrochloride, Phenbutazone Sodium Glycerate, Phencarbamide, Phencyclidine Hydrochloride, Phendimetrazine Tartrate, Phenelzine Sulfate, Phenmetrazine Hydrochloride, Phenobarbital, Phenoxybenzamine Hydrochloride, Phenprocoumon, phenserine, phensuccinal, Phensuximide, Phentermine, Phentermine Hydrochloride, phentolamine mesylate, Phentoxifylline, Phenyl Aminosalicylate, phenylacetate, Phenylalanine, phenylalanyl ketoconazole, Phenylbutazone, Phenylephrine Hydrochloride, Phenylpropanolamine Hydrochloride, Phenylpropanolamine Polistirex, Phenyramidol Hydrochloride, Phenytoin, phosphatase inhibitors, Physostigmine, picenadol, picibanil, Picotrin Diolamine, picroliv, picumeterol, pidotimod, Pifarnine, ilocarpine, pilsicainide, pimagedine, Pimetine Hydrochloride, pimilprost, Pimobendan, Pimozide, Pinacidil, Pinadoline, Pindolol, pinnenol, pinocebrin, Pinoxepin Hydrochloride, pioglitazone, Pipamperone, Pipazethate, pipecuronium bromide, Piperacetazine, Piperacillin Sodium, Piperamide Maleate, piperazine, Pipobroman, Piposulfan, Pipotiazine Palmitate, Pipoxolan Hydrochloride, Piprozolin, Piquindone Hydrochloride, Piquizil Hydrochloride, Piracetam, Pirandamine Hydrochloride, pirarubicin, Pirazmonam Sodium, Pirazolac, Pirbenicillin Sodium, Pirbuterol Acetate, Pirenperone, Pirenzepine Hydrochloride, piretanide, Pirfenidone, Piridicillin Sodium, Piridronate Sodium, Piriprost, piritrexim, Pirlimycin Hydrochloride, pirlindole, pirmagrel, Pirmenol Hydrochloride, Pirnabine, Piroctone, Pirodavir, pirodomast, Pirogliride Tartrate, Pirolate, Pirolazamide, Piroxantrone Hydrochloride, Piroxicam, Piroximone, Pirprofen, Pirquinozol, Pirsidomine, Prenylamine, Pituitary, Posterior, Pivampicillin Hydrochloride, Pivopril, Pizotyline, placetin A, platinum compounds, platinum-triamine complex, Plicamycin, Plomestane, Pobilukast Edamine, Podofilox, Poisonoak Extract, Poldine Methylsulfate, Poliglusam, Polignate Sodium, Polymyxin B Sulfate, Polythiazide, Ponalrestat, Porfimer Sodium, Porfiromycin, Potassium Chloride, Potassium Iodide, Potassium Permanganate, Povidone-Iodine, Practolol, Pralidoxime Chloride, Pramiracetam Hydrochloride, Pramoxine Hydrochloride, Pranolium Chloride, Pravadoline Maleate, Pravastatin (Pravachol), Prazepam, Prazosin, Prazosin Hydrochloride, Prednazate, Prednicarbate, Prednimustine, Prednisolone, Prednisone, Prednival, Pregnanolone Succiniate, Prenalterol Hydrochloride, Pridefine Hydrochloride, Prifelone, Prilocaine Hydrochloride, Prilosec, Primaquine Phosphate, Primidolol, Primidone, Prinivil, prinomide Tromethamine, Prinoxodan, Prizidilol Hydrochloride, Proadifen Hydrochloride, Probenecid, Probicromil Calcium, Probucol, Procainamide Hydrochloride, Procaine Hydrochloride, Procarbazine Hydrochloride, Procaterol Hydrochloride, Prochlorperazine, Procinonide, Proclonol, Procyclidine Hydrochloride, Prodilidine Hydrochloride, Prodolic Acid, Profadol Hydrochloride, Progabide, Progesterone, Proglumide, Proinsulin Human, Proline, Prolintane Hydrochloride, Promazine Hydrochloride, Promethazine Hydrochloride, Propafenone Hydrochloride, propagermanium, Propanidid, Propantheline Bromide, Proparacaine Hydrochloride, Propatyl Nitrate, propentofylline, Propenzolate Hydrochloride, Propikacin, Propiomazine, Propionic Acid, propionylcarnitine, L-, propiram, propiram+paracetamol, propiverine, Propofol, Propoxycaine Hydrochloride, Propoxyphene Hydrochloride, Propranolol Hydrochloride, Propulsid, propyl bis-acridone, Propylhexedrine, Propyliodone, Propylthiouracil, Proquazone, Prorenoate Potassium, Proroxan Hydrochloride, Proscillaridin, Prostalene, prostratin, Protamine Sulfate, protegrin, Protirelin, protosufloxacin, Protriptyline Hydrochloride, Proxazole, Proxazole Citrate, Proxicromil, Proxorphan Tartrate, prulifloxacin, Pseudoephedrine Hydrochloride, Puromycin, purpurin, Pyrabrom, Pyrantel, Pamoate, Pyrazinamide, Pyrazofurin, pyrazoloacridine, Pyridostigmine Bromide, Pyrilamine Maleate, Pyrimethamine, Pyrinoline, Pyrithione Sodium, Pyrithione Zinc, Pyrovalerone Hydrochloride, Pyroxamine Maleate, Pyrrocaine, Pyrroliphene Hydrochloride, Pyrrolnitrin, Pyrvinium Pamoate, Quadazocine Mesylate, Quazepam, Quazinone, Quazodine, Quazolast, quetiapine, quiflapon, quinagolide, Quinaldine Blue, quinapril, Quinaprilat, Quinazoline Hydrochloride, Quinbolone, Quinctolate, Quindecamine Acetate, Quindonium Bromide, Quinelorane Hydrochloride, Quinestrol, Quinfamide, Quingestanol Acetate, Quingestrone, Quinidine Gluconate, Quinelorane Hydrochloride, Quinine Sulfate, Quinpirole Hydrochloride, Quinterenol Sulfate, Quinuclium Bromide, Quinupristin, Quipazine Maleate, Rabeprazole Sodium, Racephenicol, Racepinephrine, raf antagonists, Rafoxanide, Ralitoline, raloxifene, raltitrexed, ramatroban, Ramipril, Ramoplanin, ramosetron, ranelic acid, Ranimycin, Ranitidine, ranolazine, Rauwolfia Serpentina, recainam, Recainam Hydrochloride, Reclazepam, regavirumab, Regramostim, Relaxin, Relomycin, Remacemide Hydrochloride, Remifentanil Hydrochloride, Remiprostol, Remoxipride, Repirinast, Repromicin, Reproterol Hydrochloride, Reserpine, resinferatoxin, Resorcinol, retelliptine demethylated, reticulin, reviparin sodium, revizinone, rhenium Re 186 etidronate, rhizoxin, Ribaminol, Ribavirin, Riboprine, ribozymes, ricasetron, Ridogrel, Rifabutin, Rifamastene, Rifamexil, Rifamide, Rifampin, Rifapentine, Rifaximin, R 11 retinamide, rilopirox, Riluzole, rimantadine, Rimazole Hydrochloride, Rimexolone, Rimiterol Hydrobromide, rimoprogin, riodipine, Rioprostil, Ripazepam, ripisartan, Risedronate Sodium, risedronic acid, Risocaine, Risotilide Hydrochloride, rispenzepine, Risperdal, Risperidone, Ritanserin, ritipenem, Ritodrine, Ritolukast, ritonavir, rizatriptan benzoate, Rocastine Hydrochloride, Rocuronium Bromide, Rodocaine, Roflurane, Rogletimide, rohitukine, rokitamycin, Roletamde, Rolgamidine, Rolicyprine, Rolipram, Rolitetracycline, Rolodine, Romazarit, romurtide, Ronidazole, ropinirole, Ropitoin Hydrochloride, ropivacaine, Ropizine, roquinimex, Rosaramicin, Rosoxacin, Rotoxamine, roxatidine, Roxarsone, roxindole, roxithromycin, rubiginone Bi, ruboxyl, rufloxacin, rupatadine, Rutamycin, ruzadolane, Sabeluzole, safingol, safironil, saintopin, salbutamol, Salcolex, Salethamide Maleate, Salicyl Alcohol, Salicylamide, Salicylate Meglumine, Salicylic Acid, Salmeterol, Salnacedin, Salsalate, sameridine, sampatrilat, Sancycline, sanfetrinem, Sanguinarium Chloride, Saperconazole, saprisartan, sapropterin, saquinavir, Sarafloxacin Hydrochloride, Saralasin Acetate, SarCNU, sarcophytol A, sargramostim, Sarmoxicillin, Sarpicillin, sarpogrelate, saruplase, saterinone, satigrel, satumomab pendetide, Schick Test Control, Scopafungin, Scopolamine Hydrobromide, Serazapine Hydrochloride, Sdi 1 mimetics, Secalciferol, Secobarbital, Seelzone, Seglitide Acetate, selegiline, Selegiline Hydrochloride, Selenium Sulfide, Selenomethionine Se 75, Selfotel, sematilide, semduramicin, semotiadil, semustine, sense oligonucleotides, Sepazonium Chloride, Seperidol Hydrochloride, Seprilose, Seproxetine Hydrochloride, Seractide Acetate, Sergolexole Maleate, Serine, Sermetacin, Sermorelin Acetate, sertaconazole, sertindole, sertraline, setiptiline, Setoperone, sevirumab, sevoflurane, sezolamide, Sibopirdine, Sibutramine Hydrochloride, signal transduction inhibitors, Silandrone, silipide, silteplase, Silver Nitrate, simendan, Simtrazene, Simvastatin, Sincalide, Sinefungin, sinitrodil, sinnabidol, sipatrigine, sirolimus, Sisomicin, Sitogluside, sizofiran, sobuzoxane, Sodium Amylosulfate, Sodium Iodide I 123, Sodium Nitroprusside, Sodium Oxybate, sodium phenylacetate, Sodium Salicylate, solverol, Solypertine Tartrate, Somalapor, Somantadine Hydrochloride, somatomedin B, somatomedin C, somatrem, somatropin, Somenopor, Somidobove, sonermin, Sorbinil, Sorivudine, sotalol, Soterenol Hydrochloride, Sparfloxacin, Sparfosate Sodium, sparfosic acid, Sparsomycin, Sparteine Sulfate, Spectinomycin Hydrochloride, spicamycin, Spiperone, Spiradoline Mesylate, Spiramycin, Spirapril Hydrochloride, Spiraprilat, Spirogermanium Hydrochloride, Spiromustine, Spironolactone, Spiropitan, Spiroxasone, splenopentin, spongistatin 1, Sprodiamide, squalamine, Stallimycin Hydrochloride, Stannous Pyrophosphate, Stannous Sulfur Colloid, Stanozolol, Statolon, staurosporine, stavudine, Steffimycin, Stenbolone Acetate, stepronin, Stilbazium Iodide, Stilonium Iodide, stipiamide, Stiripentol, stobadine, Streptomycin Sulfate, Streptonicozid, Streptonigrin, Streptozocin, stromelysin inhibitors, Strontium Chloride Sr 89, succibun, Succimer, Succinylcholine Chloride, Sucralfate, Sucrosofate Potassium, Sudoxicam, Sufentanil, Sufotidine, Sulazepam, Sulbactam Pivoxil, Sulconazole Nitrate, Sulfabenz, Sulfabenzamide, Sulfacetamide, Sulfacytine, Sulfadiazine, Sulfadoxine, Sulfalene, Sulfamerazine, Sulfameter, Sulfamethazine, Sulfamethizole, Sulfamethoxazole, Sulfamonomethoxine, Sulfamoxole, Sulfanilate Zinc, Sulfanitran, sulfasalazine, Sulfasomizole, Sulfazamet, Sulfinalol Hydrochloride, sulfinosine, Sulfinpyrazone, Sulfisoxazole, Sulfomyxin, Sulfonterol Hydrochloride, sulfoxamine, Sulindac, Sulmarin, Sulnidazole, Suloctidil, Sulofenur, sulopenem, Suloxifen Oxalate, Sulpiride, Sulprostone, sultamicillin, Sulthiame, sultopride, sulukast, Sumarotene, sumatriptan, Suncillin Sodium, Suproclone, Suprofen, suradista, suramin, Surfomer, Suricainide Maleate, Suritozole, Suronacrine Maleate, Suxemerid Sulfate, swainsonine, symakalim, Symclosene, Symetine Hydrochloride, synthetic glycosaminoglycans, Taciamine Hydrochloride, Tacrine Hydrochloride, Tacrolimus, Talampicillin Hydrochloride, Taleranol, Talisomycin, tallimustine, Talmetacin, Talniflumate, Talopram Hydrochloride, Talosalate, Tametraline Hydrochloride, Tamoxifen, Tampramine Fumarate, Tamsulosin Hydrochloride, Tandamine Hydrochloride, tandospirone, tapgen, taprostene, Tasosartan, tauromustine, Taxane, Taxol, Tazadolene Succinate, tazanolast, tazarotene, Tazifylline Hydrochloride, Tazobactam, Tazofelone, Tazolol Hydrochloride, Tebufelone, Tebuquine, Technetium Tc 99 m Bicisate, Teclozan, Tecogalan Sodium, Teecleukin, Teflurane, Tegafur, Tegretol, Teicoplanin, telenzepine, tellurapyrylium, telmesteine, telmisartan, telomerase inhibitors, Teloxantrone Hydrochloride, Teludipine Hydrochloride, Temafloxacin Hydrochloride, Tematropium Methyl sulfate, Temazepam, Temelastine, temocapril, Temocillin, temoporfin, temozolomide, Tenidap, Teniposide, tenosal, tenoxicam, tepirindole, Tepoxalin, Teprotide, terazosin, Terbinafine, Terbutaline Sulfate, Terconazole, terfenadine, terflavoxate, terguride, Teriparatide Acetate, terlakiren, terlipressin, terodiline, Teroxalene Hydrochloride, Teroxirone, tertatolol, Tesical, Tesimide, Testolactone, Testosterone, Tetracaine, tetrachlorodecaoxide, Tetracycline, Tetrahydrozoline Hydrochloride, Tetramisole Hydrochloride, Tetrazolast Meglumine, tetrazomine, Tetrofosmin, Tetroquinone, Tetroxoprim, Tetrydamine, thaliblastine, Thalidomide, Theofibrate, Theophylline, Thiabendazole, Thiamiprine, Thiamphenicol, Thiamylal, Thiazesim Hydrochloride, Thiazinamium Chloride, Thiethylperazine, Thimerfonate Sodium, Thimerosal, thiocoraline, thiofedrine, Thioguanine, thiomarinol, Thiopental Sodium, thioperamide, Thioridazine, Thiotepa, Thiothixene, Thiphenamil Hydrochloride, Thiphencillin Potassium, Thiram, Thozalinone, Threonine, Thrombin, thrombopoietin, thrombopoietin mimetic, thymalfasin, thymopoietin receptor agonist, thymotrinan, Thyromedan Hydrochloride, Thyroxine 1 125, Thyroxine 1 131, Tiacrilast, Tiacrilast Sodium, tiagabine, Tiamenidine, tianeptine, tiapafant, Tiapamil Hydrochloride, Tiaramide Hydrochloride, Tiazofurin, Tibenelast Sodium, Tibolone, Tibric Acid, Ticabesone Propionate, Ticarbodine, Ticarcillin Cresyl Sodium, Ticlatone, ticlopidine, Ticrynafen, tienoxolol, Tifurac Sodium, Tigemonam Dicholine, Tigestol, Tiletamine Hydrochloride, Tilidine Hydrochloride, tilisolol, tilnoprofen arbamel, Tilorone Hydrochloride, Tiludronate Disodium, tiludronic acid, Timefurone, Timobesone Acetate, Timolol, tin ethyl etiopurpurin, Tinabinol, Tinidazole, Tinzaparin Sodium, Tioconazole, Tiodazosin, Tiodonium Chloride, Tioperidone Hydrochloride, Tiopinac, Tiospirone Hydrochloride, Tiotidine, tiotropium bromide, Tioxidazole, Tipentosin Hydrochloride, Tipredane, Tiprenolol Hydrochloride, Tiprinast Meglumine, Tipropidil Hydrochloride, Tiqueside, Tiquinamide Hydrochloride, tirandalydigin, Tirapazamine, tirilazad, tirofiban, tiropramide, titanocene dichloride, Tixanox, Tixocortol Pivalate, Tizanidine Hydrochloride, Tobramycin, Tocainide, Tocamphyl, Tofenacin Hydrochloride, Tolamolol, Tolazamide, Tolazoline Hydrochloride, Tolbutamide, Tolcapone, Tolciclate, Tolfamide, Tolgabide, lamotrigine, Tolimidone, Tolindate, Tolmetin, Tolnaftate, Tolpovidone 1 131, Tolpyrramide, Tolrestat, Tomelukast, Tomoxetine Hydrochloride, Tonazocine Mesylate, Topiramate, topotecan, Topotecan Hydrochloride, topsentin, Topterone, Toquilone, torasemide, toremifene, Torsemide, Tosifan, Tosufloxacin, totipotent stem cell factor, Tracazolate, trafermin, Tralonide, Tramadol Hydrochloride, Tramazoline Hydrochloride, trandolapril, Tranexamic Acid, Tranilast, Transcainide, translation inhibitors, traxanox, Trazodone Hydrochloride, Trazodone-HCL, Trebenzomine Hydrochloride, Trefentanil Hydrochloride, Treloxinate, Trepidam Maleate, Trestolone Acetate, tretinoin, Triacetin, triacetyluridine, Triafungin, Triamcinolone, Triampyzine Sulfate, Triamterene, Triazolam, Tribenoside, tricaprilin, Tricetamide, Trichlormethiazide, trichohyalin, triciribine, Tricitrates, Triclofenol piperazine, Triclofos Sodium, Triclonide, trientine, Trifenagrel, triflavin, Triflocin, Triflubazam, Triflumidate, Trifluoperazine Hydrochloride, Trifluperidol, Triflupromazine, Triflupromazine Hydrochloride, Trifluridine, Trihexyphenidyl Hydrochloride, Trilostane, Trimazosin Hydrochloride, trimegestone, Trimeprazine Tartrate, Trimethadione, Trimethaphan Camsylate, Trimethobenzamide Hydrochloride, Trimethoprim, Trimetozine, Trimetrexate, Trimipramine, Trimoprostil, Trimoxamine Hydrochloride, Triolein 1 125, Triolein 1 131, Trioxifene Mesylate, Tripamide, Tripelennamine Hydrochloride, Triprolidine Hydrochloride, Triptorelin, Trisulfapyrimidines, Troclosene Potassium, troglitazone, Trolamine, Troleandomycin, trombodipine, trometamol, Tropanserin Hydrochloride, Tropicamide, tropine ester, tropisetron, trospectomycin, trovafloxacin, trovirdine, Tryptophan, Tuberculin, Tubocurarine Chloride, Tubulozole Hydrochloride, tucaresol, tulobuterol, turosteride, Tybamate, tylogenin, Tyropanoate Sodium, Tyrosine, Tyrothricin, tyrphostins, ubenimex, Uldazepam, Undecylenic Acid, Uracil Mustard, urapidil, Urea, Uredepa, uridine triphosphate, Urofollitropin, Urokinase, Ursodiol, valaciclovir, Valine, Valnoctamide, Valproate Sodium, Valproic Acid, valsartan, vamicamide, vanadeine, Vancomycin, vaminolol, Vapiprost Hydrochloride, Vapreotide, variotin, Vasopressin, Vecuronium Bromide, velaresol, Velnacrine Maleate, venlafaxine, veradol Hydrochloride, veramina, Verapamil Hydrochloride, verdins, Verilopam Hydrochloride, Verlukast, Verofylline, veroxan, verteporfin, Vesnarinone, vexibinol, Vidarabine, vigabatrin, Viloxazine Hydrochloride, Vinblastine Sulfate, vinburnine citrate, Vincofos, vinconate, Vincristine Sulfate, Vindesine, Vindesine Sulfate, Vinepidine Sulfate, Vinglycinate Sulfate, Vinleurosine Sulfate, vinorelbine, vinpocetine, vintoperol, vinxaltine, Vinzolidine Sulfate, Viprostol, Virginiamycin, Viridofulvin, Viroxime, vitacin, Volazocine, voriconazole, vorozole, voxergolide, Warfarin Sodium, Xamoterol, Xanomeline, Xanoxate Sodium, Xanthinol Niacinate, xemilofiban, Xenalipin, Xenbucin, Xilobam, ximoprofen, Xipamide, Xorphanol Mesylate, Xylamidine Tosylate, Xylazine Hydrochloride, Xylometazoline Hydrochloride, Xylose, yangambin,zabicipril, zacopride, zafirlukast, Zalcitabine, zaleplon, zalospirone, Zaltidine Hydrochloride, zaltoprofen, zanamivir, zankiren, zanoterone, Zantac, Zafirlukast, zatebradine, zatosetron, Zatosetron Maleate, zenarestat, Zenazocine Mesylate, Zeniplatin, Zeranol, Zidometacin, Zidovudine, zifrosilone, Zilantel, zilascorb, zileuton, Zimeldine Hydrochloride, Zinc Undecylenate, Zindotrine, Zinoconazole Hydrochloride, Zinostatin, Zinterol Hydrochloride, Zinviroxime, ziprasidone, Zobolt, Zofenopril Calcium, Zofenoprilat, Zolamine Hydrochloride, Zolazepam Hydrochloride, zoledronic acid, Zolertine Hydrochloride, zolmitriptan, zolpidem, Zomepirac Sodium, Zometapine, Zoniclezone Hydrochloride, Zonisamide, zopiclone, Zopolrestat, Zorbamyciin, Zorubicin Hydrochloride, zotepine, Zucapsaicin, JTT-501 (PNU-182716) (Reglitazar), AR-H039242, MCC-555 (Netoglitazone), AR-H049020, Tesaglitazar), CS-011 (CI-1037), GW-409544X, KRP-297, RG-12525, BM-15.2054, CLX-0940, CLX-0921, DRF-2189, GW-1929, GW-9820, LR-90, LY-510929, NIP-221, NIP-223, JTP-20993, LY 29311 Na, FK 614, BMS 298585, R 483, TAK 559, DRF 2725 (Ragaglitazar), L-686398, L-168049, L-805645, L-054852, Demethyl asteriquinone B1 (L-783281), L-363586, KRP-297, P32/98, CRE-16336 and EML-16257 and pharmaceutically acceptable salts therof.

12. A dosage form according to claim 1, wherein the high dose, high solubility active ingredient comprises dose from 500 mg to 1500 mg.

13. A dosage form according to claim 1, wherein the high dose, high solubility active ingredient is selected from the group consisting of adrenergic agent; adrenocortical steroid; adrenocortical suppressant; aldosterone antagonist; amino acid; anabolic; analeptic; analgesic; anesthetic; anorectic; anti-acne agent; anti-adrenergic; anti-allergic; anti-amebic; anti-anemic; anti-anginal; anti-arthritic; anti-asthmatic; antiatherosclerotic; antibacterial; anticholinergic; anticoagulant; anticonvulsant; antidepressant; antidiabetic; antidiarrheal; antidiuretic; anti-emetic; anti-epileptic; antifibrinolytic; antifungal; antihemorrhagic; antihistamine; antihyperlipidemia; antihypertensive; antihypotensive; anti-infective; anti-inflammatory; antimicrobial; antimigraine; antimitotic; antimycotic, antinauseant, antineoplastic, antineutropenic, antiparasitic; antiproliferative; antipsychotic; antirheumatic; antiseborrheic; antisecretory; antispasmodic; antithrombotic; anti-ulcerative; antiviral; appetite suppressant; blood glucose regulator; bone resorption inhibitor; bronchodilator; cardiovascular agent; cholinergic; depressant; diagnostic aid; diuretic; dopaminergic agent; estrogen receptor agonist; fibrinolytic; fluorescent agent; free oxygen radical scavenger; gastric acid supressant; gastrointestinal motility effector; glucocorticoid; hair growth stimulant; hemostatic; histamine H2 receptor antagonists; hormone; hypocholesterolemic; hypoglycemic; hypolipidemic; hypotensive; imaging agent; immunizing agent; immunomodulator; immunoregulator; immunostimulant; immunosuppressant; keratolytic; LHRH agonist; mood regulator; mucolytic; mydriatic; nasal decongestant; neuromuscular blocking agent; neuroprotective; NMDA antagonist; non-hormonal sterol derivative; plasminogen activator; platelet activating factor antagonist; platelet aggregation inhibitor; psychotropic; radioactive agent; scabicide; sclerosing agent; sedative; sedative-hypnotic; selective adenosine A1 antagonist; serotonin antagonist; serotonin inhibitor; serotonin receptor antagonist; steroid; thyroid hormone; thyroid inhibitor; thyromimetic; tranquilizer; amyotrophic lateral sclerosis agent; cerebral ischemia agent; Paget's disease agent; unstable angina agent; vasoconstrictor; vasodilator; wound healing agent; and xanthine oxidase inhibitor.

14. A dosage form according to claim 1, wherein the high dose, high solubility active ingredient is selected from the group consisting of metformin hydrochloride, phenformin, buformin, potassium chloride, clindamycin, hydroxyurea, eprosartan, erythromycin, lactobionate, vancomycin hydrochloride, balsalazide disodium, sodium valproate, niacin, aminocaproic acid, acetaminophen ciprofloxacin, quetiapine and pharmaceutically acceptable salts thereof.

15. A dosage form according to claim 1, wherein inner portion may optionally contain more than one low dose active ingredients.

16. A process for the preparation of a dosage form as claimed in claim 1, comprising a) preparation of inner portion and b) preparation of outer portion.

17. A process for the preparation of a dosage form as claimed in claim 16, wherein preparation of outer portion comprising a) preparing a micro matrix particles consisting of high dose, high solubility active ingredient and one or more hydrophobic release controlling agent and b) coating the said micro matrix particles containing high solubility active ingredient and one or more hydrophobic release controlling agent.

18. A dosage form of combination of high dose high solubility hypolipidemic active ingredient as modified release and low dose hypolipidemic or antithrombotic active ingredient as immediate release, suitable for swallowing; comprising an inner portion having a low dose hypolipidemic or antithrombotic active ingredient as immediate release and an outer portion having a high dose high solubility hypolipidemic active ingredient as modified release,wherein said inner portion is covered by the outer portion from all the sides except a top surface that remains uncovered; wherein said outer portion prepared by using dual retard technique to control the release of high dose high solubility is a combination of matrix formulation and reservoir formulation comprises:
  (a) micro matrix particles consisting of a high dose high solubility hypolipidemic active ingredient and one or more hydrophobic release controlling agents wherein the ratio of high dose high solubility hypolipidemic active ingredients and hydrophobic release controlling agents is in the range of 100-2.5 to 100:30 and
  (b) a coating of one or more hyrophobic release controlling agents on said micro matrix particles, wherein the ratio of micro matrix particles and hydrophobic release controlling agent is in the range of 100:2.5 to 100:30 wherein the weight ratio of immediate release hypolipidemic or antithrombotic active ingredient and modified release hypolipidemic active ingredient is from 1:1 to 1:15000wherein the claimed dosage form does not provide burst release.

19. A dosage form according to claim 18, wherein the hydrophobic release controlling agents are selected from the group consisting of poly(ethyl acrylate, methyl methacrylate, trimethylammonioethyl methacrylate chloride) 1:2:0.1; poly (ethyl acrylate, methyl methacrylate, trimethylamonioethyl methacrylate chloride) 1:2:0.2 and poly(ethyl acrylate, methyl methacrylate) 1:1 polyvinyl acetate dispersion, ethylcellulose, cellulose acetate, cellulose propionate (lower, medium or higher molecular weight), cellulose acetate propionate, cellulose acetate butyrate, cellulose acetate phthalate, cellulose triacetate, poly(methyl methacrylate), poly (ethyl methacrylate), poly(butyl methacrylate), poly(isobutyl methacrylate), poly (hexyl methacrylate), poly(isodecyl methacrylate), poly (lauryl methacrylate), poly(phenyl methacrylate), poly (methyl acrylate), poly (isopropyl acrylate), poly (isobutyl actylate), poly (octadecylacrylate), waxes selected from the group consisting of beeswax, carnauba wax, microcrystalline wax, and ozokerite; fatty alcohols selected from the group consisting of cetostearyl alcohol, stearyl alcohol; cetyl alcohol and myristyl alcohol; and fatty acid esters selected from the group consisting of glyceryl monostearate; glycerol monooleate, acetylated monoglycerides, tristearin, tripalmitin, cetyl esters wax, glyceryl palmitostearate, glyceryl behenate, glycerol distearate and hydrogenated castor oil.

20. A dosage form according to claim 19, wherein the hydrophobic release controlling agent(s) is selected from the group consisting of poly(ethyl acrylate, methyl methacrylate, trimethylammonioethyl methacrylate chloride) 1:2:0.1; poly (ethyl acrylate, methyl methacrylate, trimethylamonioethyl methacrylate chloride) 1:2:0.2 and poly(ethyl acrylate, methyl methacrylate) 1:1.

21. A dosage form according to claim 20, wherein the ammonio methacrylate co-polymers are selected from the group consisting of poly(ethyl acrylate, methyl methacrylate, trimethylammonioethyl methacrylate chloride) 1:2:0.1; poly (ethyl acrylate, methyl methacrylate, trimethylamonioethyl methacrylate chloride) 1:2:0.2 and poly(ethyl acrylate, methyl methacrylate) 1:1.

22. A dosage form according to claim 6, wherein the hydrophobic release controlling agents is selected from fatty acid esters selected from the group consisting of glyceryl monostearate, glycerol distearate, glycerol monoleate, acetylated monoglycerides, tristearin, tripalmitin, cetyl esters wax, glyercyl palmitostearate, glyceryl behenate, glycerol distearate, and hydrogenated castor oil.

23. A dosage form according to claim 22, wherein the hydrophobic release controlling agents are selected from the group consisting of hydrogenated castor oil and glycerol distearate.

24. A dosage form according to claim 18, wherein the low dose hypolipidemic or antithrombotic active ingredient comprises dose less than or equal to 500 mg.

25. A dosage form according to claim 18, wherein the high dose high solubility hypolipidemic is niacin or its pharmaceutically acceptable salts.

26. A dosage form according to claim 18, wherein the high dose high solubility hypolipidemic active ingredient comprises dose from 500 mg to 1500 mg.

27. A dosage form according to claim 18, wherein the low dose antithrombotic active agent is aspirin.

28. A dosage form according to claim 18, wherein the low dose hypolipidemic active ingredient is selected from the group consisting of statin compounds.

29. A process for the preparation of a dosage form as claimed in claim 18, comprising a) preparation of inner portion and b) preparation of outer portion.

30. A process for the preparation of a dosage form as claimed in claim 29, wherein preparation of outer portion comprising a) preparing a micro matrix particles consisting of high dose, hypolipidemic active ingredient and one or more hydrophobic release controlling agent and b) coating the said micro matrix particles consisting of high dose hypolipidemic active ingredient and one or more hydrophobic release controlling agent.

* * * * *